US010696664B2

(12) United States Patent
Heil et al.

(10) Patent No.: US 10,696,664 B2
(45) Date of Patent: *Jun. 30, 2020

(54) PHENOXAZINE DERIVATIVES FOR ORGANIC ELECTROLUMINESCENT DEVICES

(71) Applicant: Merck Patent GmbH, Darmstadt (DE)

(72) Inventors: Holger Heil, Frankfurt am Main (DE); Beate Burkhart, Darmstadt (DE); Lara-Isabel Rodriguez, Darmstadt (DE); Sebastian Meyer, Aschaffenburg (DE); Rouven Linge, Darmstadt (DE); Amandine Darsy, Frankfurt am Main (DE)

(73) Assignee: MERCK PATENT GMBH (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/752,660

(22) PCT Filed: Jul. 15, 2016

(86) PCT No.: PCT/EP2016/001241
§ 371 (c)(1),
(2) Date: Jun. 4, 2018

(87) PCT Pub. No.: WO2017/028940
PCT Pub. Date: Feb. 23, 2017

(65) Prior Publication Data
US 2018/0258082 A1 Sep. 13, 2018

(30) Foreign Application Priority Data
Aug. 14, 2015 (EP) ..................................... 15181178

(51) Int. Cl.
| H01L 51/00 | (2006.01) |
| C07D 413/14 | (2006.01) |
| C07D 265/38 | (2006.01) |
| H01L 51/50 | (2006.01) |

(52) U.S. Cl.
CPC ......... *C07D 413/14* (2013.01); *C07D 265/38* (2013.01); *H01L 51/0035* (2013.01); *H01L 51/0071* (2013.01); *H01L 51/5012* (2013.01); *H01L 51/5056* (2013.01); *H01L 51/5096* (2013.01)

(58) Field of Classification Search
CPC . C07D 265/38; C07D 413/14; H01L 51/0035; H01L 51/0071; H01L 51/5012; H01L 51/5056; H01L 51/5096
See application file for complete search history.

(56) References Cited

U.S. PATENT DOCUMENTS

| 2003/0168970 | A1* | 9/2003 | Tominaga | C07C 15/28 313/504 |
| 2004/0054152 | A1* | 3/2004 | Meerholz | C07D 305/06 534/15 |
| 2004/0135131 | A1* | 7/2004 | Treacher | C07C 17/2632 252/582 |
| 2010/0308714 | A1* | 12/2010 | Gessner | C07D 279/26 313/504 |
| 2013/0059902 | A1* | 3/2013 | Corey | C12N 15/113 514/44 A |
| 2013/0292665 | A1* | 11/2013 | Ono | C09K 11/06 257/40 |
| 2014/0061548 | A1 | 3/2014 | Montenegro et al. | |
| 2014/0339476 | A1* | 11/2014 | Schulte | H01L 51/0035 252/500 |
| 2015/0014671 | A1* | 1/2015 | Koike | C07D 401/10 257/40 |
| 2016/0343949 | A1* | 11/2016 | Seo | C09K 11/06 |
| 2017/0025615 | A1* | 1/2017 | Seo | H05B 33/20 |
| 2017/0115564 | A1* | 4/2017 | Yonezawa | G03F 7/027 |
| 2018/0212156 | A1* | 7/2018 | Baba | C07D 233/06 |
| 2018/0240983 | A1* | 8/2018 | Heil | H01L 51/0058 |

FOREIGN PATENT DOCUMENTS

| WO | 2010010356 A2 | 1/2010 |
| WO | 2010119275 A1 | 10/2010 |
| WO | 2012150001 A1 | 11/2012 |

OTHER PUBLICATIONS

Kulkarni et al., "New Ambipolar Organic Semiconductors. 2. Effects of Electron Acceptor Strength on Intramolecular Charge Transfer Photophysics, Highly Efficient Electroluminescence, and Field-Effect Charge Transport of Phenoxazine-Based Donor-Acceptor Materials," Chem. Mater., vol. 20, No. 13, pp. 4212-4223 (2008).
Ried et al., "Synthese von 6-Oxo-4.5.7-triphenyl-2.6-dihydrobenzoxazolen und Oxidationsprodukte des 6-Amino-2.4.5-triphenyl-resorcins," Liebigs Ann. Chem., vol. 764, pp. 11-20 (1972).

* cited by examiner

*Primary Examiner* — Mohammed Shamsuzzaman
(74) *Attorney, Agent, or Firm* — Kim IP Law Group PLLC

(57) ABSTRACT

The present invention relates to the compounds of the formula (1) and to organic electroluminescent devices, in particular blue-emitting devices, in which these compounds are used as host material or dopant in the emitting layer and/or as hole-transport material and/or as electron-transport material.

23 Claims, No Drawings

PHENOXAZINE DERIVATIVES FOR ORGANIC ELECTROLUMINESCENT DEVICES

RELATED APPLICATIONS

This application is a national stage entry, filed pursuant to 35 U.S.C. § 371, of PCT/EP2016/001241, filed Jul. 15, 2016, which claims the benefit of European Patent Application No. 15181178.3, filed Aug. 14, 2015, which is incorporated herein by reference in its entirety.

The present invention relates to a compound of the formula (1), to the use of the compound in an electronic device, and to an electronic device comprising a compound of the formula (1). The present invention furthermore relates to a process for the preparation of a compound of the formula (1) and to a formulation comprising one or more compounds of the formula (1).

The development of functional compounds for use in electronic devices is currently the subject of intensive research. The aim here is, in particular, the development of compounds with which improved properties of electronic devices in one or more relevant points can be achieved, such as, for example, power efficiency, lifetime or colour coordinates of the emitted light.

In accordance with the present invention, the term electronic device is taken to mean, inter alia, organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and organic electroluminescent devices (OLEDs).

Of particular interest is the provision of compounds for use in the last-mentioned electronic devices called OLEDs. The general structure and the functional principle of OLEDs are known to the person skilled in the art and are described, inter alia, in U.S. Pat. Nos. 4,539,507, 5,151,629, EP 0676461 and WO 1998/27136.

Further improvements are still necessary with respect to the performance data of OLEDs, in particular with a view to broad commercial use, for example in display devices or as light sources. Of particular importance in this connection are the lifetime, the efficiency and the operating voltage of the OLEDs and the colour values achieved. In particular in the case of blue-emitting OLEDs, there is potential for improvement with respect to the lifetime of the devices. In addition, it is desirable, for use as functional materials in electronic devices, for the compounds to have high thermal stability and a high glass-transition temperature and to be capable of sublimation without decomposition.

An important starting point for achieving the said improvements is the choice of the emitter compound employed in the electronic device.

Blue-fluorescent emitters known from the prior art are a multiplicity of compounds, in particular arylamines containing one or more condensed aryl groups and/or indenofluorene groups. Examples thereof are the pyrenearylamines disclosed in U.S. Pat. No. 5,153,073 and the pyrenearylamines disclosed in WO 2012/048780. Further examples of arylamine emitters are benzoindenofluorenamines, for example in accordance with WO 2008/006449 or WO 2008/003464, and dibenzoindenofluorenamines, for example in accordance with WO 2007/140847.

Furthermore, the use of fluorenamines which contain aromatic groups condensed onto the fluorene system is known in the prior art. The compounds which contain two or more arylamino groups are employed as fluorescent emitters (US 2012/0161615). However, the compounds exhibit green to green-blue emission and not blue emission.

Furthermore, KR 2009/131536 and WO 2004/061048 disclose benzofluorene derivatives which carry a diphenylamino group. However, compounds of this type have excessively short-wave emission to be used as blue-fluorescent emitters, or their efficiency and lifetime are unsatisfactory on use in OLEDs.

The use of phenoxazine derivatives as emitting compounds in OLEDs is also known from the prior art (US 2007/0176541, KR 2013/0115855).

However, further improvements are still necessary with respect to the colour values achieved in the case of blue-emitting OLEDs. More particularly, there is a need for deep-blue fluorescent emitters for OLEDs, which exhibit very good colour properties in terms of colour-depth and narrow emission band and at the same time still exhibit good properties in terms of lifetime, efficiency and operating voltage of the OLEDs.

Furthermore, there is also a need for alternative hole-transport materials. In hole-transport materials in accordance with the prior art, the voltage generally increases with the layer thickness of the hole-transport layer. In practice, a greater layer thickness of the hole-transport layer would frequently be desirable, but this often has the consequence of a higher operating voltage and worse performance data. In this connection, there is a need for novel hole-transport materials which have high charge-carrier mobility, enabling thicker hole-transport layers to be achieved with an only slight increase in the operating voltage.

The prior art discloses the use, in particular, of arylamine compounds and carbazole compounds as hole-transport materials for OLEDs.

The applications WO 2010/083871, WO 2011/107186 and WO 2012/150001 disclose the use of heterocyclic derivatives of anthracenes which are substituted by one or more arylamino groups or by one or more carbazole groups as functional materials in OLEDs, preferably as hole-transport and hole-injection materials.

Again furthermore, the application US 2010/0019658 discloses the use of dihydroacridine derivatives which carry aryl or heteroaryl groups as substituents of the methylene group of the dihydroacridine as functional materials in OLEDs.

However, there continues to be a need for alternative hole-transport and hole-injection materials for use in OLEDs. In particular, there is a need for materials with which the above-mentioned, highly desired improvements in the performance data and properties of OLEDs can be achieved.

There is likewise a need for alternative matrix materials for use in OLEDs and in other electronic devices. In particular, there is a need for matrix materials for phosphorescent dopants and for matrix materials for mixed-matrix systems, which preferably result in good efficiency, a long lifetime and a low operating voltage of the electronic devices.

The present invention is thus based on the technical object of providing compounds which are suitable for use in electronic devices, such as, for example, OLEDs, and which can be employed, in particular, as blue emitters, as hole-transport materials and/or as matrix materials.

Surprisingly, it has been found that compounds in which an aromatic (or heteroaromatic) ring system or diarylamino group is linked para to the oxygen atom of a phenoxazine compound are very suitable for use in organic electroluminescent devices. These compounds exhibit very good colour properties in terms of color-depth and narrow emission band and at the same time still exhibit good properties in terms of lifetime, efficiency and operating voltage of the OLEDs. Furthermore, these compounds are very suitable as hole-transport and hole-injection materials and as matrix materials for phosphorescent emitters. An increase in the efficiency and lifetime of the organic electronic device compared with materials in accordance with the prior art is possible using these materials. Furthermore, these materials are very suitable for use in organic electronic devices since they have a high glass transition temperature. The present invention therefore relates to these materials and to the use thereof in organic electronic devices.

As part of the present invention, it has now been found that compounds of the formula (1) indicated below are highly suitable for the above-mentioned uses.

The invention thus relates to a compound of formula (1)

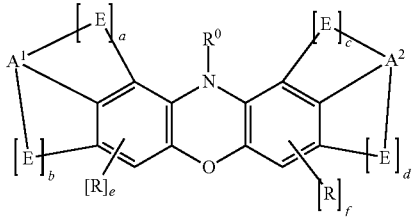

formula (1)

where the following applies to the symbols and indices:
$A^1$, $A^2$ are, on each occurrence, identically or differently, selected from $Ar^1$ or $N(Ar^2)_2$;
E is on each occurrence, identically or differently, a divalent bridge selected from $B(R^1)$, $C(R^1)_2$, $Si(R^1)_2$, C=O, C=NR$^1$, C=C(R$^1)_2$, O, S, S=O, SO$_2$, N(R$^1$), P(R$^1$) and P(=O)R$^1$;
or E is a group of the following formula (E-1),

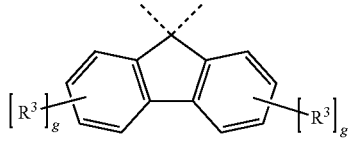

formula (E-1)

where the dashed bonds indicate the bonding to the phenoxazine structure and to $A^1$ or $A^2$;
$Ar^1$, $Ar^2$ are, on each occurrence, identically or differently, selected from the group consisting of an aromatic or heteroaromatic ring system having 5 to 30 aromatic ring atoms, which may be substituted by one or more radicals $R^2$, where two groups $Ar^2$ may be linked to one another and may form a ring;
R, $R^0$, $R^1$, $R^2$ are on each occurrence, identically or differently, H, D, F, Br, Cl, I, C(=O)R$^3$, CN, Si(R$^3$)$_3$, N(R$^3$)$_2$, P(=O)(R$^3$)$_2$, S(=O)R$^3$, S(=O)$_2$R$^3$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^3$ and where one or more CH$_2$ groups in the above-mentioned groups may be replaced by —R$^3$C=CR$^3$—, —C≡C—, Si(R$^3$)$_2$, C=O, C=NR$^3$, —C(=O)O—, —C(=O)NR$^3$—, NR$^3$, P(=O)(R$^3$), —O—, —S—, SO or SO$_2$, or an aromatic or heteroaromatic ring system having 5 to 30 aromatic ring atoms, which may in each case be substituted by one or more radicals $R^3$, or an aryloxy or heteroaryloxy group having 5 to 30 aromatic ring atoms, which may be substituted by one or more radicals $R^3$, where two substituents $R^1$, which are attached to the same C or Si atom, may be linked to one another and may form an aliphatic or aromatic ring, and where two adjacent substituents $R^2$ may be linked to one another and may form an aliphatic or aromatic ring;
$R^3$ is on each occurrence, identically or differently, H, D, F, Br, Cl, I, C(=O)R$^4$, CN, Si(R$^4$)$_3$, N(R$^4$)$_2$, P(=O)(R$^4$)$_2$, S(=O)R$^4$, S(=O)$_2$R$^3$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^4$ and where one or more CH$_2$ groups in the above-mentioned groups may be replaced by —R$^4$C=CR$^4$—, —C≡C—, Si(R$^4$)$_2$, C=O, C=NR$^4$, —C(=O)O—, —C(=O)NR$^4$—, NR$^4$, P(=O)(R$^4$), —O—, —S—, SO or SO$_2$, or an aromatic or heteroaromatic ring system having 5 to 30 aromatic ring atoms, which may in each case be substituted by one or more radicals $R^4$, or an aryloxy or heteroaryloxy group having 5 to 30 aromatic ring atoms, which may be substituted by one or more radicals $R^4$, where two adjacent substituents $R^3$ may be linked to one another and may form an aliphatic or aromatic ring;
$R^4$ is on each occurrence, identically or differently, H or an aliphatic, aromatic and/or heteroaromatic hydrocarbon radical having 1 to 20 C atoms, in which, in addition, H atoms may be replaced by F; two adjacent substituents $R^4$ here may also form a mono- or polycyclic aliphatic or aromatic ring system with one another;
a, b, c, d are on each occurrence, identically or differently selected from 0 or 1; where a=0, b=0, c=0 or d=0 means that the corresponding bridge is not present;
where a+b=0, 1 or 2; and
c+d=0, 1 or 2;
where a+b=0 when $A^1$ is $N(Ar^2)_2$; and
c+d=0 when $A^2$ is $N(Ar^2)_2$;
e is 0, 1, 2 or 3 and a+b+e≤3;
f is 0, 1, 2 or 3 and c+d+f≤3;
g is 0, 1, 2, 3 or 4.

An aryl group in the sense of this invention contains 6 to 60 aromatic ring atoms; a heteroaryl group in the sense of this invention contains 5 to 60 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, spentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two radicals are adjacent, for the purposes of the present application, is taken to mean that two radicals are linked to two C atoms, wherein the two C atoms are directly linked to each other.

The formulation that two or more radicals may form a ring with one another is, for the purposes of the present application, intended to be taken to mean, inter alia, that the two radicals are linked to one another by a chemical bond. This is illustrated by the following schemes:

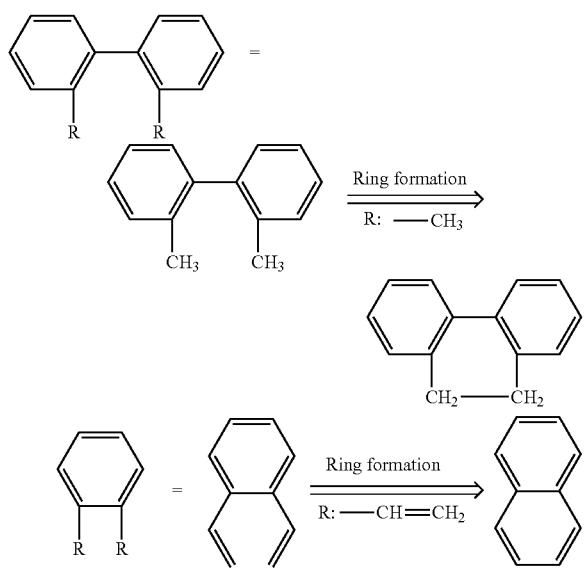

Furthermore, however, the above-mentioned formulation is also intended to be taken to mean that, in the case where one of the two radicals represents hydrogen, the second radical is bonded at the position to which the hydrogen atom was bonded, with formation of a ring. This is illustrated by the following scheme:

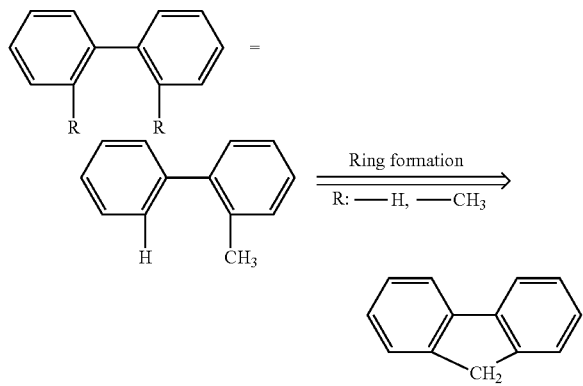

In accordance with a preferred embodiment, a+b=0 or 1 and c+d=0 or 1.

In accordance with a preferred embodiment, the group $A^1$ stands for $Ar^1$ and a+b=0 or 1 and/or the group $A^2$ stands for $Ar^1$ and c+d=0 or 1.

It is furthermore preferred for the group E to be a divalent bridge selected, on each occurrence, identically or differently, from the group consisting of $C(R^1)_2$, $Si(R^1)_2$, O and S, or E is a group of formula (E-1) as defined above, the groups $C(R^1)_2$ or the group of formula (E-1) are particularly preferred, the group $C(R^1)_2$ is very particularly preferred.

According to a preferred embodiment, $R^0$ is on each occurrence, identically or differently, a straight-chain alkyl having 1 to 20 C atoms or a branched or cyclic alkyl having 3 to 20 C atoms, where the above-mentioned groups may each be substituted by one or more radicals $R^3$ and where one or more $CH_2$ groups in the above-mentioned groups may be replaced by $-R^3C=CR^3-$, $-C\equiv C-$, $-NR^3-$, $-O-$, $-S-$, or an aromatic or heteroaromatic ring system having 5 to 14 aromatic ring atoms, which may in each case be substituted by one or more radicals $R^3$.

It is particularly preferred that $R^0$ is an aromatic or heteroaromatic ring system having 5 to 14 aromatic ring atoms, which may in each case be substituted by one or more radicals $R^3$.

According to a preferred embodiment, $R^1$ and $R^2$ are on each occurrence, identically or differently, H, D, F, CN, a straight-chain alkyl group having 1 to 20 C atoms or a branched or cyclic alkyl group having 3 to 20 C atoms, where the above-mentioned groups may each be substituted by one or more radicals $R^3$ and where one or more $CH_2$ groups in the above-mentioned groups may be replaced by $-R^3C=CR^3-$, $-C\equiv C-$, $C=O$, $-O-$, $-S-$, an aromatic or heteroaromatic ring system having 5 to 30 aromatic ring atoms, which may in each case be substituted by one or more radicals $R^3$, where two substituents $R^1$, which are attached to the same C or Si atom, may be linked to one another and may form an aliphatic or aromatic ring.

$R^1$, $R^2$ are particularly preferably on each occurrence, identically or differently, H, D, F, a straight-chain alkyl group having 1 to 10 C atoms or a branched or cyclic alkyl group having 3 to 10 C atoms, where the above-mentioned groups may each be substituted by one or more radicals $R^3$ and where one or more $CH_2$ groups in the above-mentioned groups may be replaced by $-R^3C=CR^3-$, $-C\equiv C-$, $C=O$, $-O-$, $-S-$, an aromatic or heteroaromatic ring system having 5 to 18 aromatic ring atoms, which may in each case be substituted by one or more radicals $R^3$, where two substituents $R^1$, which are attached to the same C or Si atom, may be linked to one another and may form an aliphatic or aromatic ring, and where two adjacent substituents $R^2$ may be linked to one another and may form an aliphatic or aromatic ring;

In accordance with a preferred embodiment, $R^3$ is on each occurrence, identically or differently, H, D, F, CN, $Si(R^4)_3$, $N(R^4)_2$, a straight-chain alkyl or alkoxy group having 1 to 14 C atoms or a branched or cyclic alkyl or alkoxy group having 3 to 14 C atoms, where the above-mentioned groups may each be substituted by one or more radicals $R^4$ and where one or more $CH_2$ groups in the above-mentioned groups may be replaced by $-R^4C=CR^4-$, $-C\equiv C-$, $C=O$, $-O-$, $-S-$, or an aromatic or heteroaromatic ring system having 5 to 14 aromatic ring atoms, which may in each case be substituted by one or more radicals $R^4$, where two adjacent substituents $R^3$ may be linked to one another and may form an aliphatic or aromatic ring; It is particularly preferred that $R^3$ is on each occurrence, identically or differently, H, F, a straight-chain alkyl group having 1 to 10 C atoms or a branched or cyclic alkyl or group having 3 to 10 C atoms, where the above-mentioned groups may each be substituted by one or more radicals $R^4$, or an aryl or heteroaryl group having 5 to 14 aromatic ring atoms, which may in each case be substituted by one or more radicals $R^4$, where two adjacent substituents $R^3$ may be linked to one another and may form an aliphatic or aromatic ring;

In accordance with a further preferred embodiment, both groups $A^1$ and $A^2$ stand for $Ar^1$. It is particularly preferred that both groups $A^1$ and $A^2$ stand for $Ar^1$ and that a+b=0 or 1 and c+d=0 or 1. In a very particularly preferred embodiment, $A^1$ and $A^2$ stand for $Ar^1$ and a+b=0 and c+d=0. In a further very particularly preferred embodiment, $A^1$ and $A^2$ stand for $Ar^1$ and a+b=1 and c+d=1.

Preferred embodiments of the structures of the formula (1) are the structures of the formulae (2) to (7)

formula (2)

formula (3)

formula (4)

formula (5)

formula (6)

formula (7)

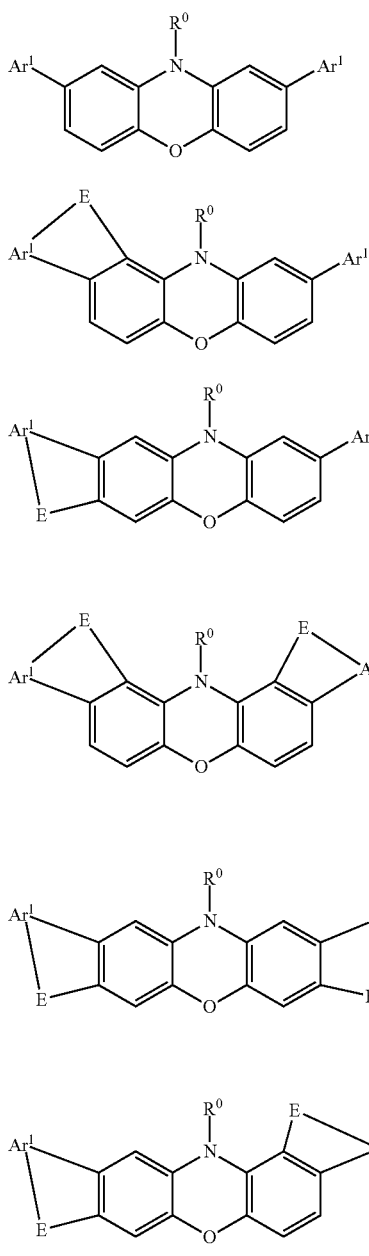

formula (2a)

formula (3a)

formula (4a)

formula (5a)

formula (6a)

formula (7a)

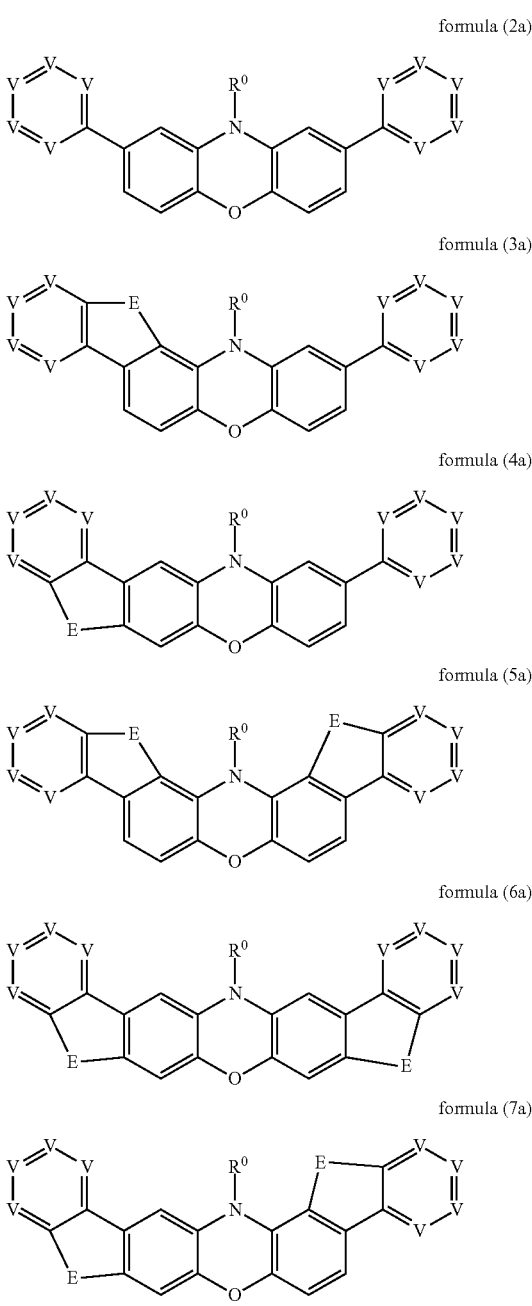

where the symbols Ar¹ and E have the same meaning as described above and where each free position of the two phenyl rings of the phenoxazine structure may be substituted by a group R.

According to a preferred embodiment of the invention, Ar¹ is selected, identically or differently, from the group consisting of an aromatic or heteroaromatic ring system having 5 to 14 aromatic ring atoms, which may be substituted by one or more radicals $R^2$.

It is very preferred that Ar¹ is selected identically from the group consisting of an aromatic or heteroaromatic ring system having 5 to 14 aromatic ring atoms, which may be substituted by one or more radicals $R^2$.

Further preferred embodiments of the structures of the formula (1) are the structures of the formulae (2a) to (7a)

where

V is, identically or differently, equal to $CR^2$, N or two adjacent groups V may stand for a group of the formula (8a) or (9a)

formula (8a)

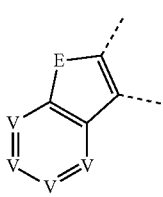

-continued formula (9a)

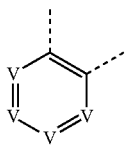

in which the dashed bonds indicate the linking of this unit; and where the symbols E and R⁰ have the same meaning as defined above.

Among formulae (2a) to (7a), the formulae (2a), (5a) and (6a) are preferred.

It is furthermore preferred for formulae (2a) to (7a) that at least one 6-membered ring in the para position to the O atom of the central ring of the phenoxazine structure comprises two adjacent groups V, which stand for a group of the formula (8a) or (9a). More preferably, both 6-membered rings in the para position to the O atom of the central ring of the phenoxazine structure comprise two adjacent groups V, which stand for a group of the formula (8a) or (9a). Very particularly preferred are structures of formulae (2a), (5a) and (6a), where both 6-membered rings in the para position to the O atom of the central ring of the phenoxazine structure comprise two adjacent groups V, which stand for a group of the formula (8a) or (9a) as depicted below with formulae (2a-1) to (2a-5), (5a-1) to (5a-5), and (6a-1) to (6a-5):

formula (2a-1)

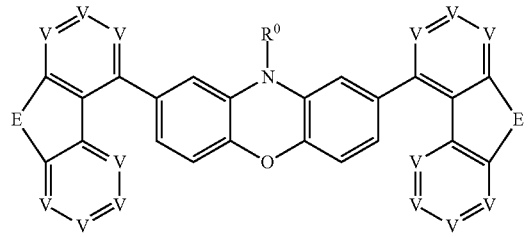

formula (2a-2)

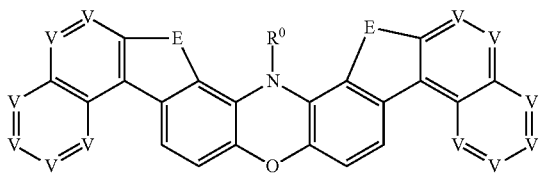

formula (2a-3)

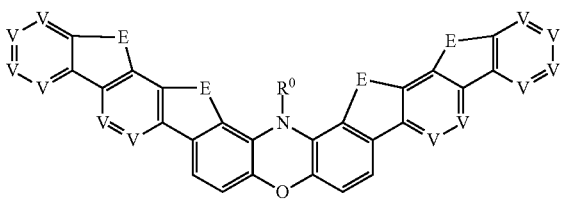

formula (2a-4)

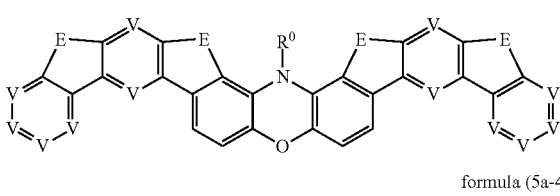

formula (2a-5)

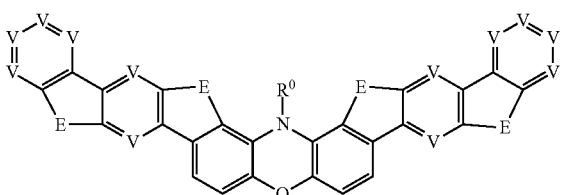

formula (5a-1)

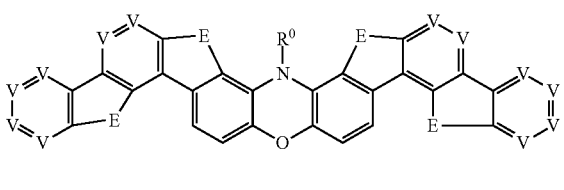

formula (5a-2)

formula (5a-3)

formula (5a-4)

formula (5a-5)

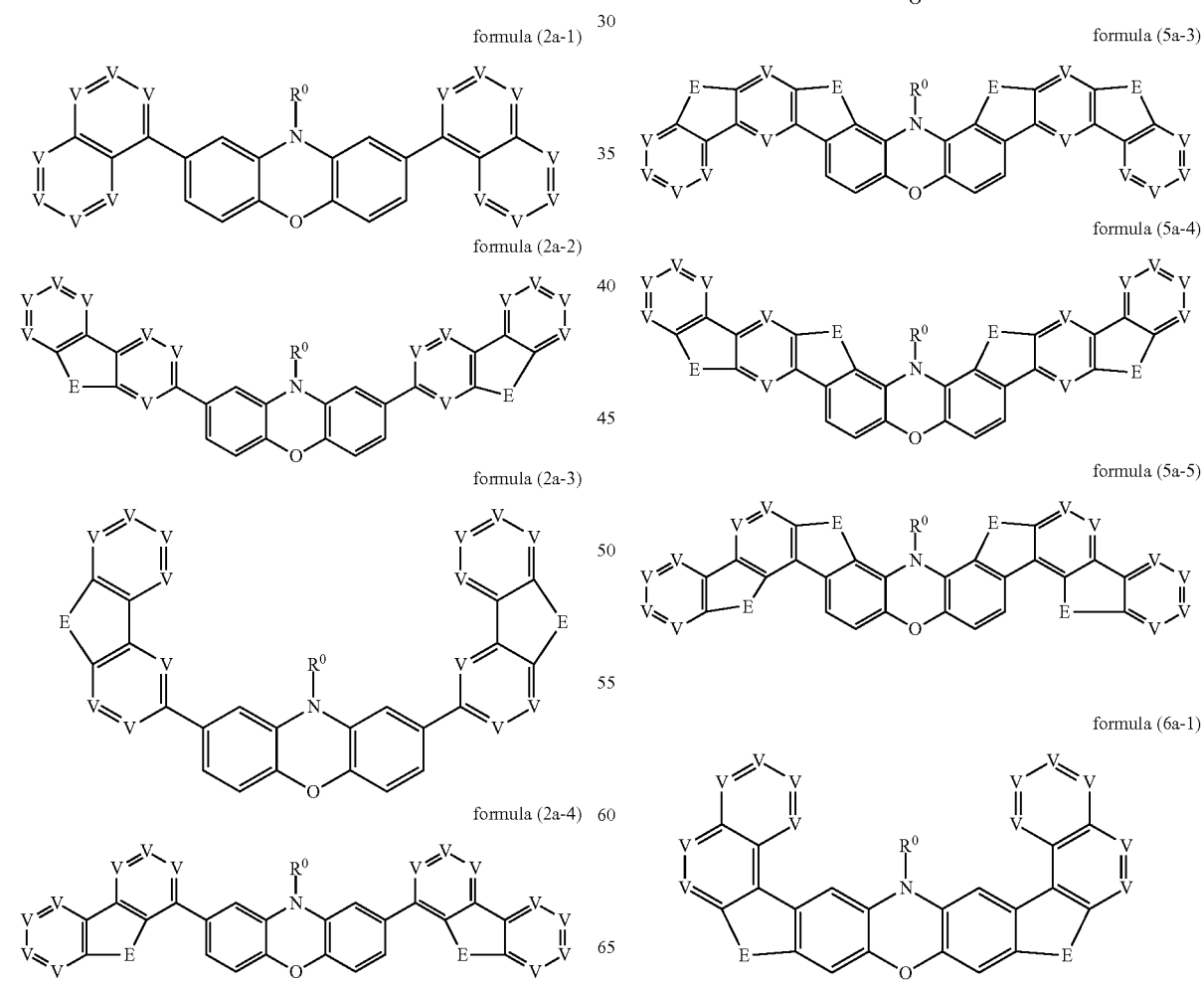

formula (6a-1)

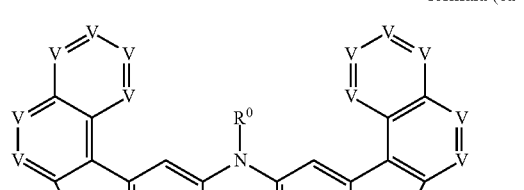

formula (6a-2)

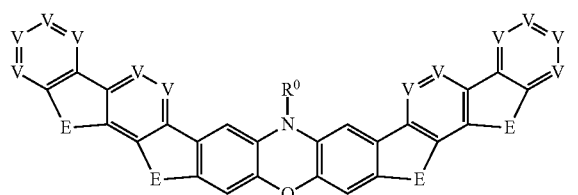

formula (6a-3)

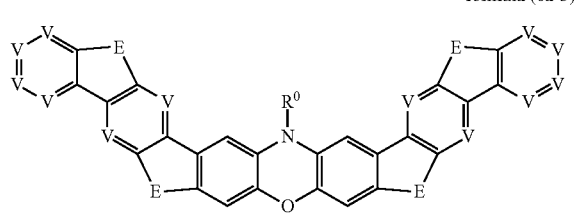

formula (6a-4)

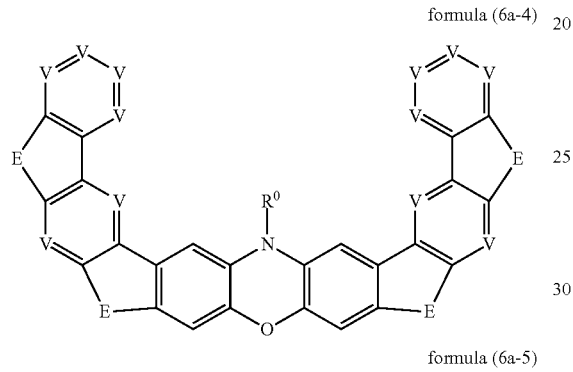

formula (6a-5)

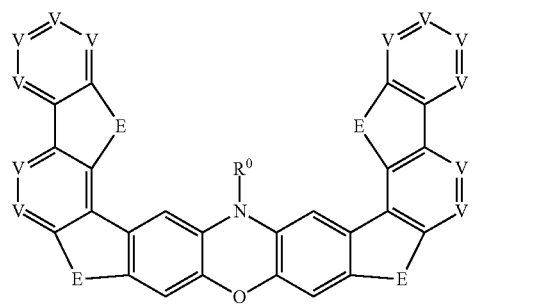

where V, E and R⁰ have the same meaning as above.

It is furthermore preferred for formulae (2a) to (7a) and their preferred embodiments, that at least one group V stands for $CR^2$, wherein $R^2$ is a selected from $N(R^3)_2$ or an aromatic or heteroaromatic ring system having 5 to 30 aromatic ring atoms, which may in each case be substituted by one or more radicals $R^3$.

In accordance with a further preferred embodiment, both groups $A^1$ and $A^2$ stand for $N(Ar^2)_2$.

Preferred embodiments of the structures of the formula (1) are the structures of the formula (20)

formula (20)

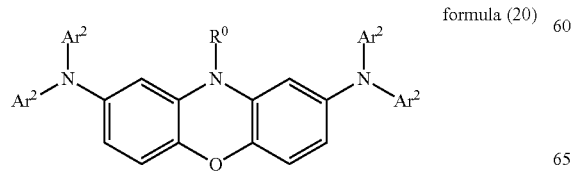

where the symbols $Ar^2$ and $R^0$ have the same meaning as defined above and where each free position of the two phenyl rings of the phenoxazine structure may be substituted by a group R.

It is particularly preferred that $Ar^2$ in formula (20) is selected, identically or differently, from the group consisting of an aryl or heteroaryl group having 5 to 18 aromatic ring atoms, which may be substituted by one or more radicals $R^2$.

It is very particularly preferred that $Ar^2$ in formula (20) is selected identically from the group consisting of an aryl or heteroaryl group having 5 to 18 aromatic ring atoms, which may be substituted by one or more radicals $R^2$.

According to a preferred embodiment, $Ar^1$ and $Ar^2$ are preferably selected from the groups of formulae (A-1) to (A-68)

formula (A-1)

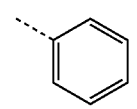

formula (A-2)

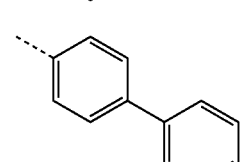

formula (A-3)

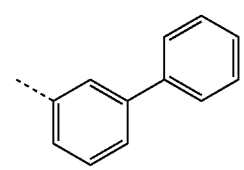

formula (A-4)

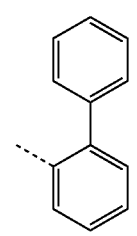

formula (A-5)

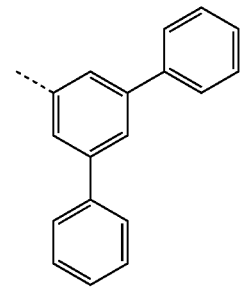

formula (A-6)

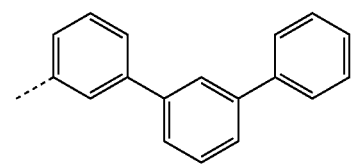

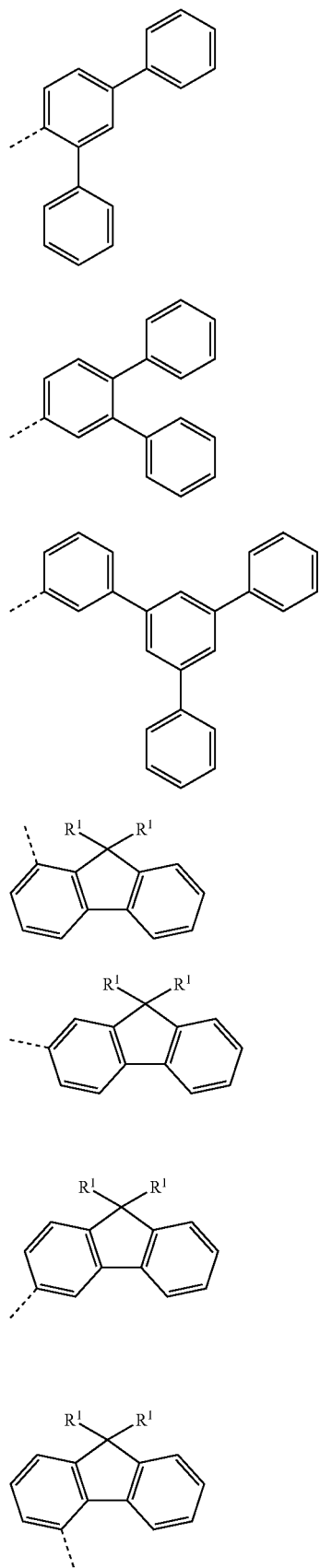
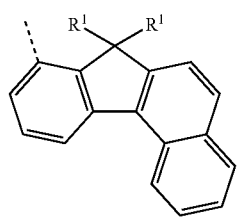
formula (A-7)
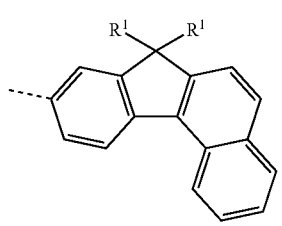
formula (A-14)
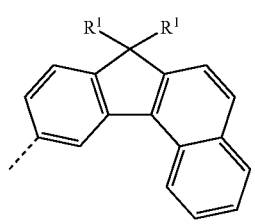
formula (A-15)
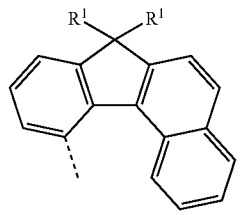
formula (A-16)
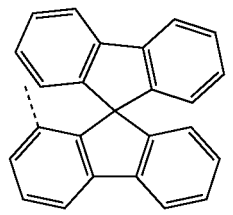
formula (A-17)
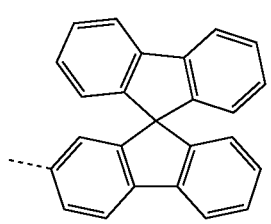
formula (A-18)
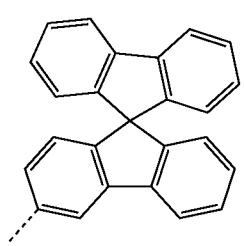
formula (A-19)
formula (Ar¹-20)

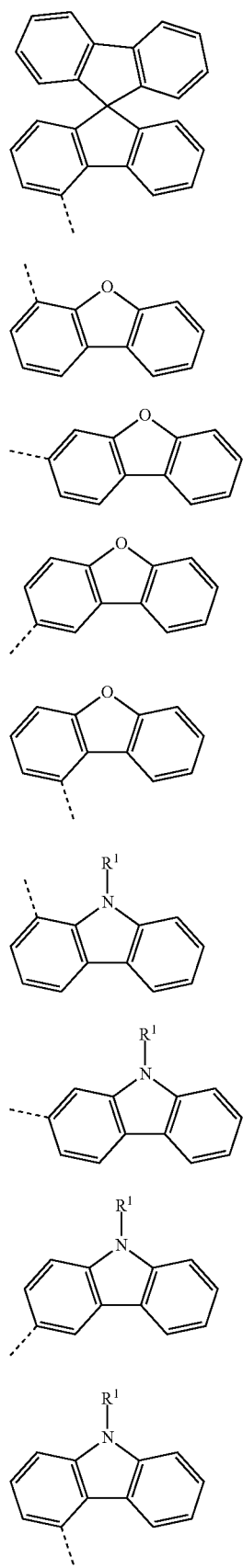
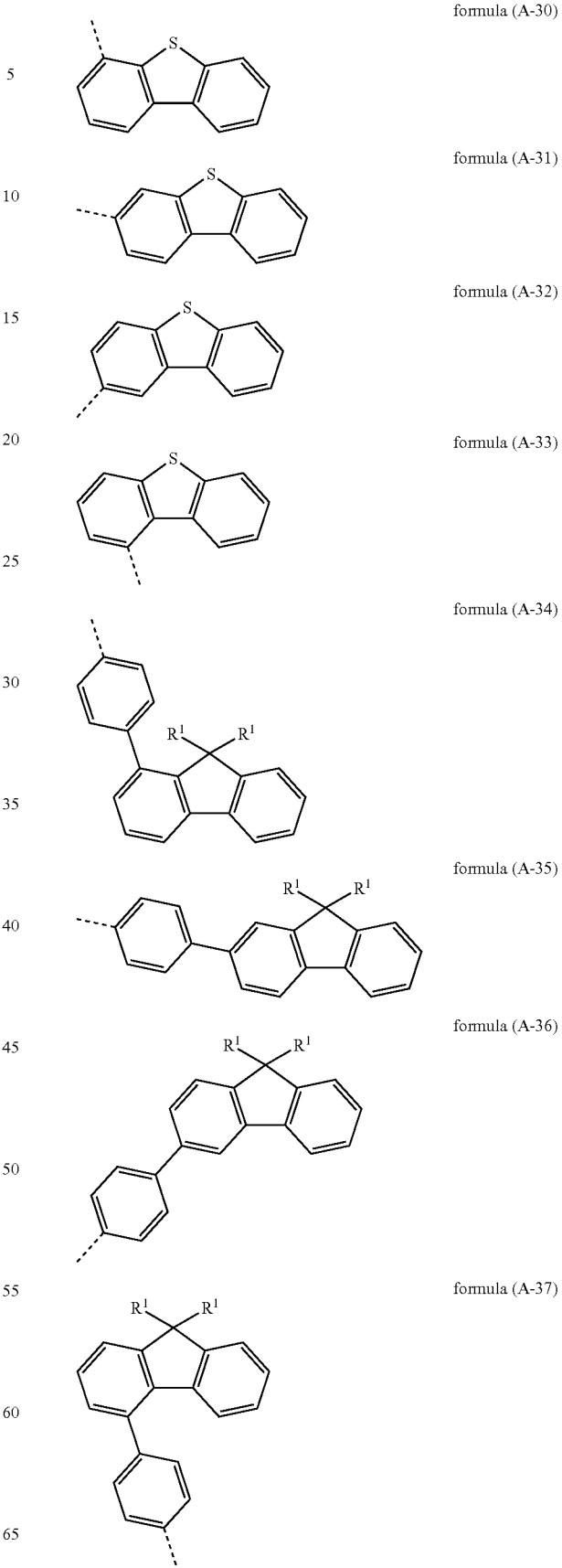

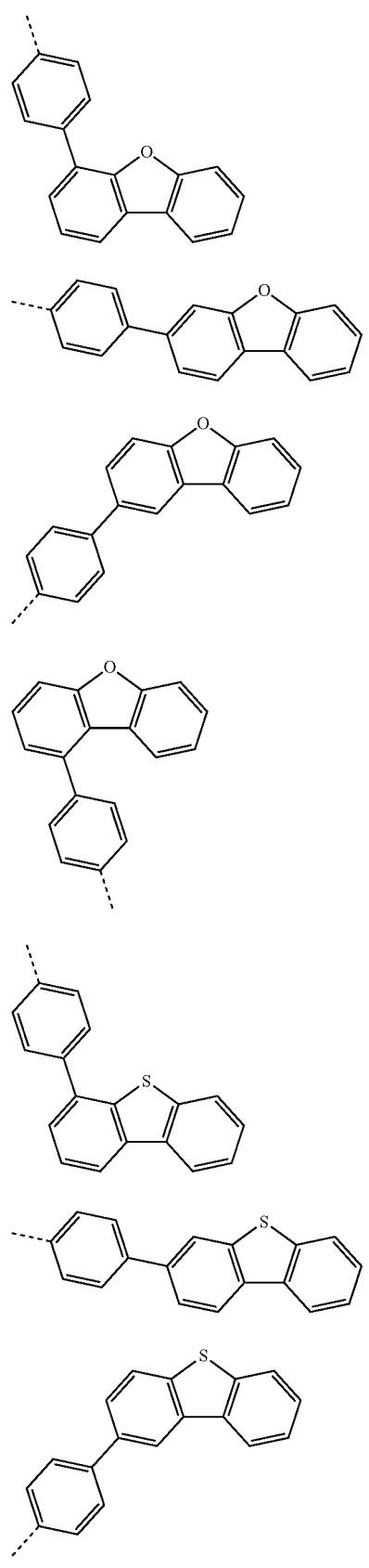
formula (A-38)
formula (A-39)
formula (A-40)
formula (A-41)
formula (A-42)
formula (A-43)
formula (A-44)
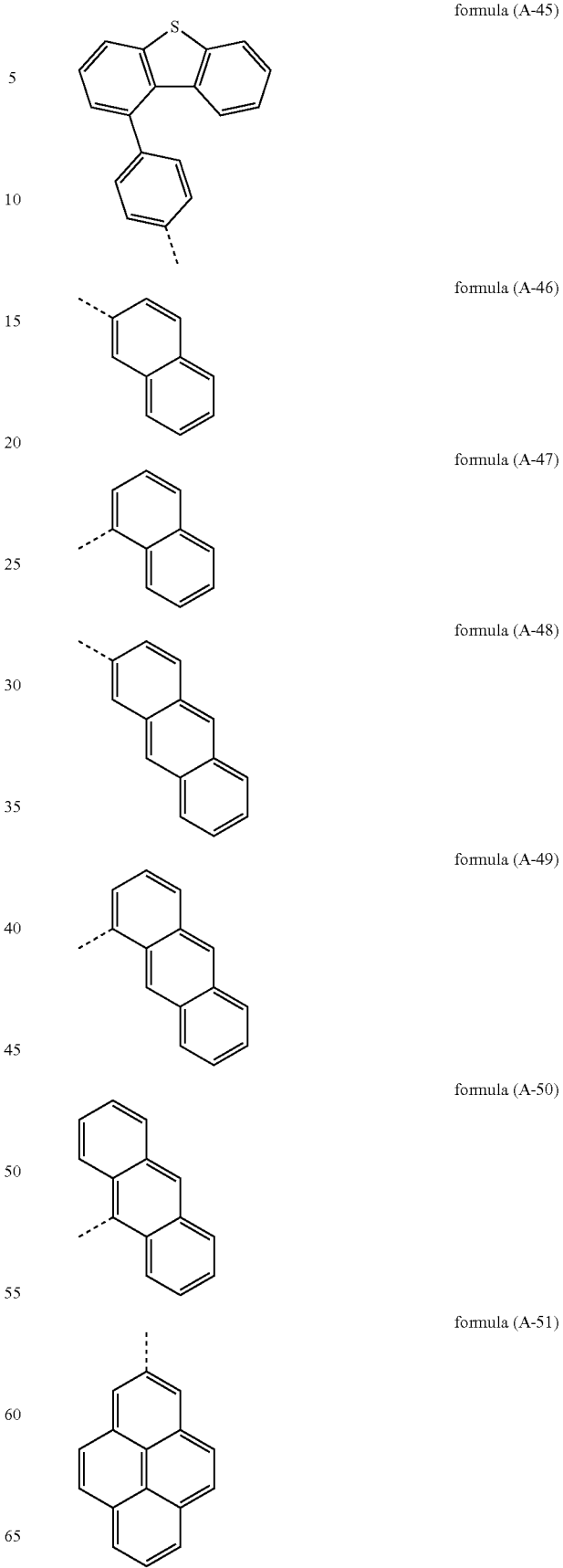
formula (A-45)
formula (A-46)
formula (A-47)
formula (A-48)
formula (A-49)
formula (A-50)
formula (A-51)

-continued
formula (A-52)
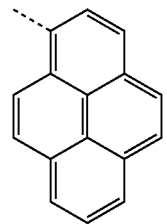
formula (A-53)
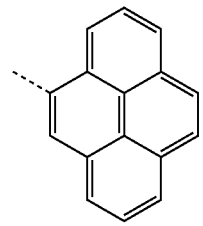
formula (A-54)
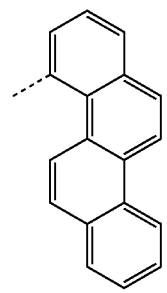
formula (A-55)
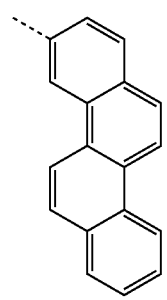
formula (A-56)
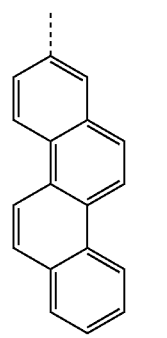
formula (A-57)
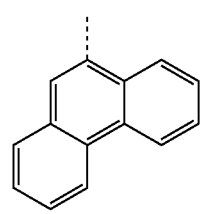
-continued
formula (A-58)
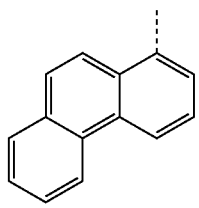
formula (A-59)
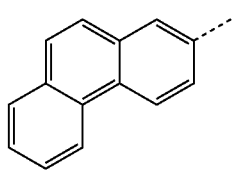
formula (A-60)
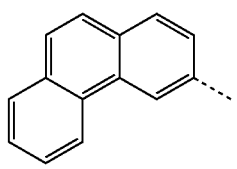
formula (A-61)
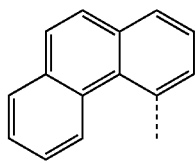
formula (A-62)
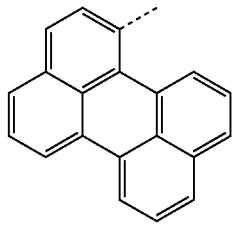
formula (A-63)
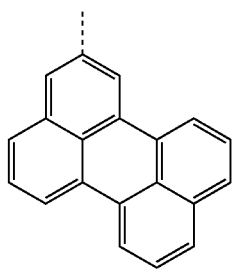
formula (A-64)
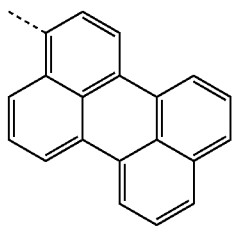

formula (A-65)
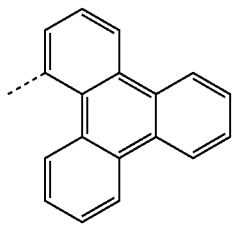

formula (A-66)
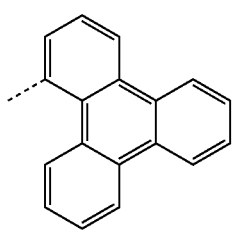

formula (A-67)
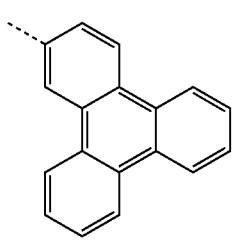

formula (A-68)
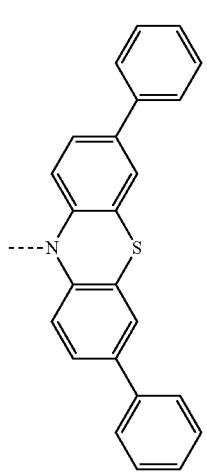

formula ($A^2$-1)
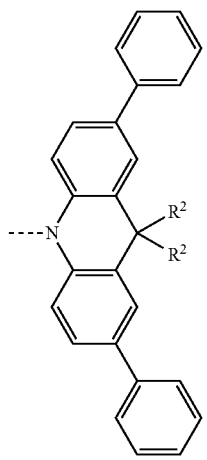

formula ($A^2$-2)
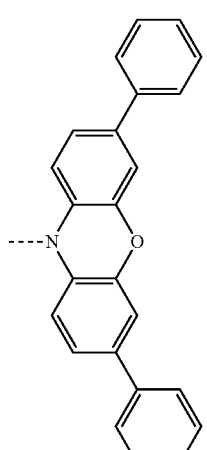

formula ($A^2$-3)

where the dashed bond in the formulae (A-1) to (A-68) indicates the linking position of $Ar^1$ para to the O atom of the phenoxazine structure element, or the linking of $Ar^2$ to the nitrogen atom in the diarylamine substituent $N(Ar^2)_2$; and if a divalent bridge E is bonded to the unit $Ar^1$, this is bonded at an adjacent position to the dashed bond; and where $R^1$ in formulae (A-10) to (A-17), (A-26) to (A-29) and (A-34) to (A-37) has the same meaning as indicated above; and where the structures of formulae (A-1) to (A-68) may be substituted by one or more radicals $R^3$, where $R^3$ has the same meaning as indicated above.

If the groups $Ar^2$ in the compounds of the formulae (1) or (20) are linked to one another, then the group $—N(Ar^2)_2$ preferably has the structure of one of the following formulae ($A^2$-1) to ($A^2$-8):

formula (A²-4)

formula (A²-5)

formula (A²-6)

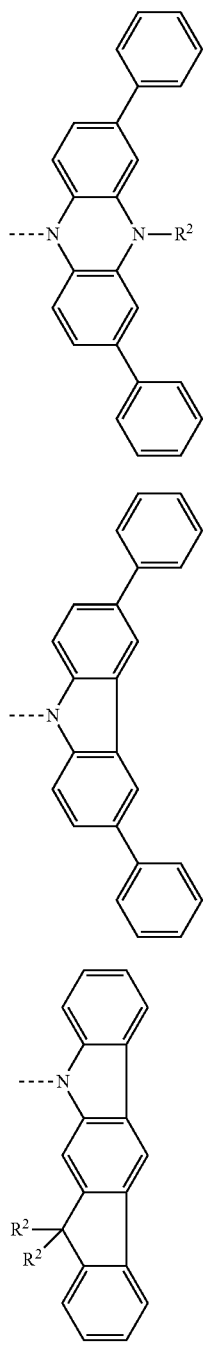

formula (A²-7)

formula (A²-8)

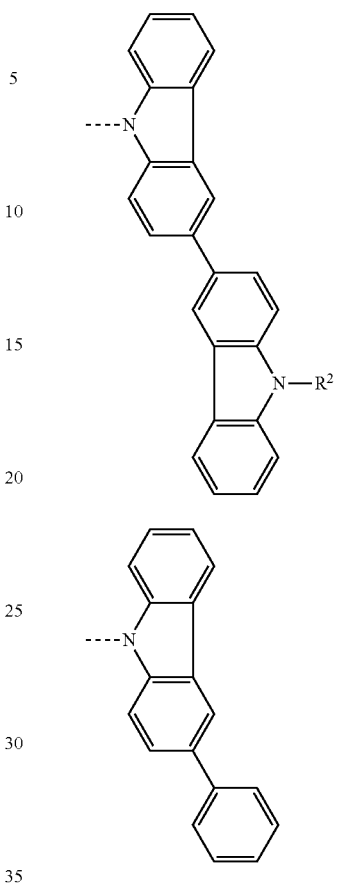

where the dashed bond in the formulae (A²-1) to (A²-8) indicates the linking of the nitrogen atom in the diarylamine substituent $N(Ar^2)_2$ para to the O atom of the phenoxazine structure element; where $R^2$ in formulae (A²-1) to (A²-4), (A²-6) and (A²-7) has the same meaning as indicated above;

For compounds which are processed by vacuum evaporation, the alkyl groups preferably have not more than four C atoms, particularly preferably not more than 1 C atom. For compounds which are processed from solution, suitable compounds are also those which are substituted by linear, branched or cyclic alkyl groups having up to 10 C atoms or which are substituted by oligoarylene groups, for example ortho-, meta-, para- or branched terphenyl or quaterphenyl groups.

Examples of suitable compounds according to the invention are the compounds shown in the following table:

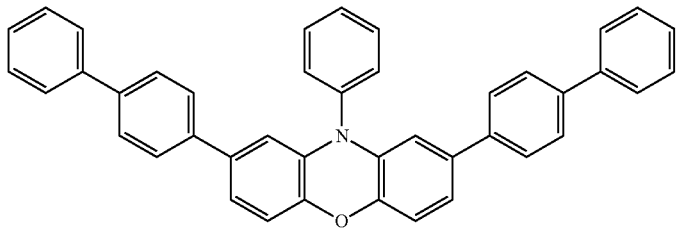 [SMILES: c1ccc(-c2ccc(-c3ccc4c(c3)N(c3ccccc3)c3cc(-c5ccc(-c6ccccc6)cc5)ccc3O4)cc2)cc1]

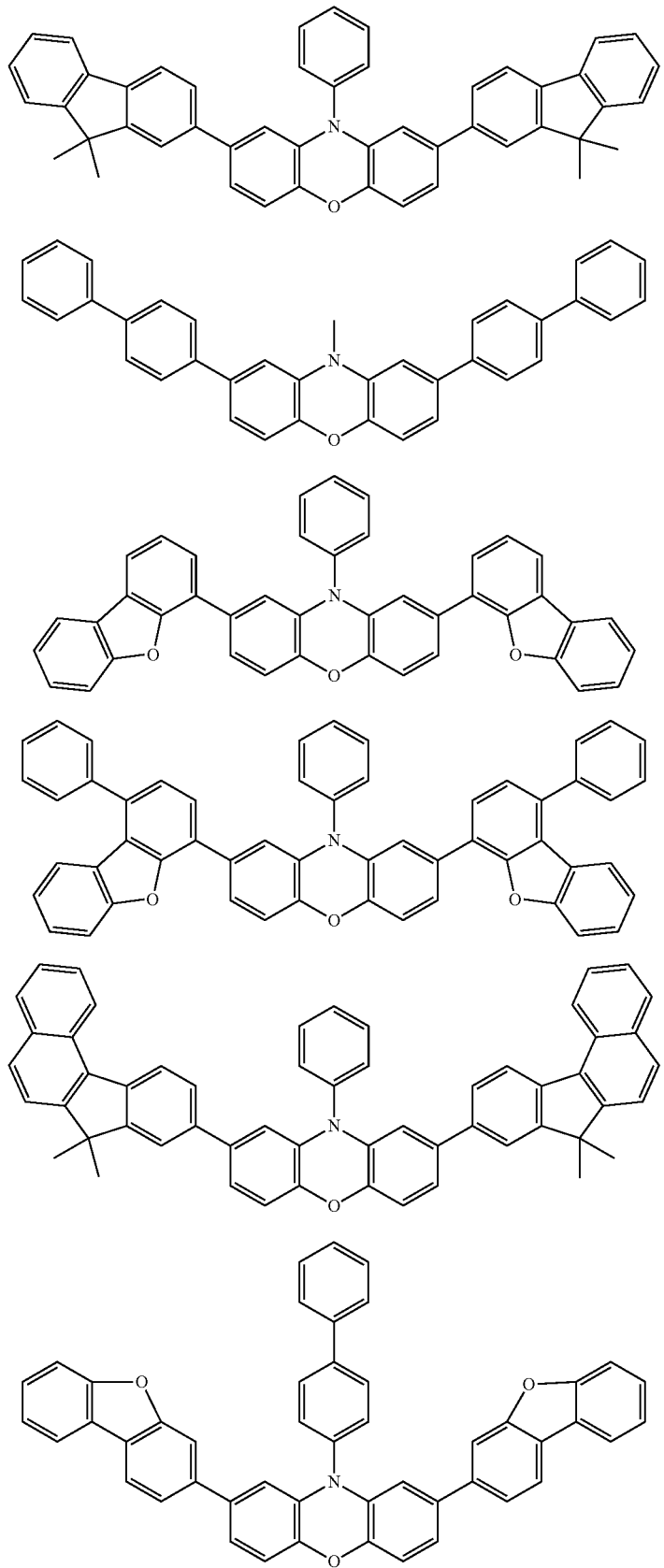

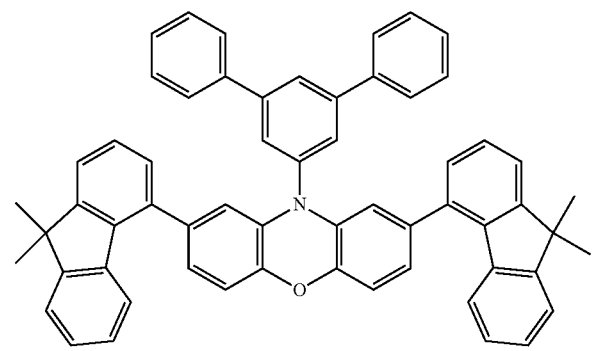
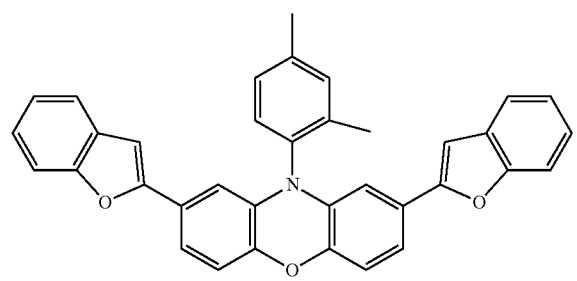 [SMILES: Cc1ccc(N2c3cc(-c4cc5ccccc5o4)ccc3Oc3ccc(-c4cc5ccccc5o4)cc32)c(C)c1]
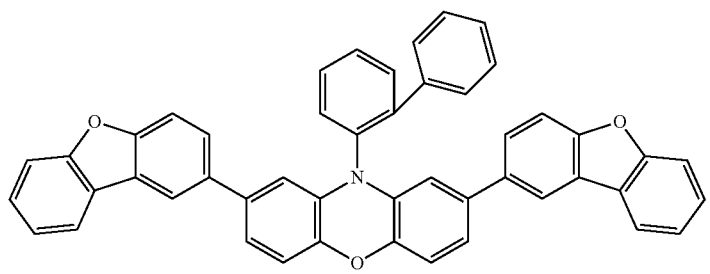 [SMILES: c1ccc(-c2ccccc2N2c3cc(-c4ccc5oc6ccccc6c5c4)ccc3Oc3ccc(-c4ccc5oc6ccccc6c5c4)cc32)cc1]
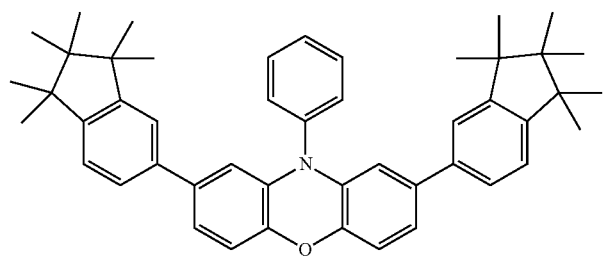
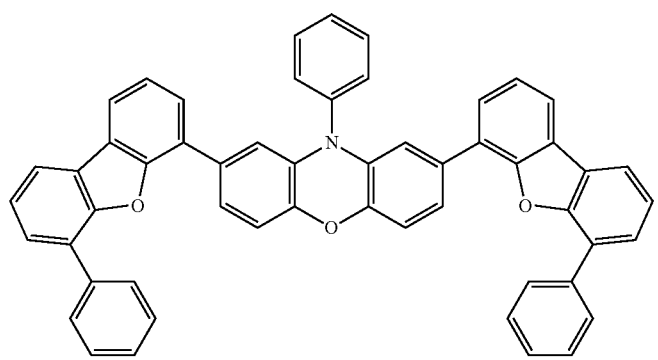 [SMILES: c1ccc(-c2cccc3c2oc2c(-c4ccc5c(c4)N(c4ccccc4)c4cc(-c6cccc7c6oc6c(-c8ccccc8)cccc67)ccc4O5)cccc23)cc1]

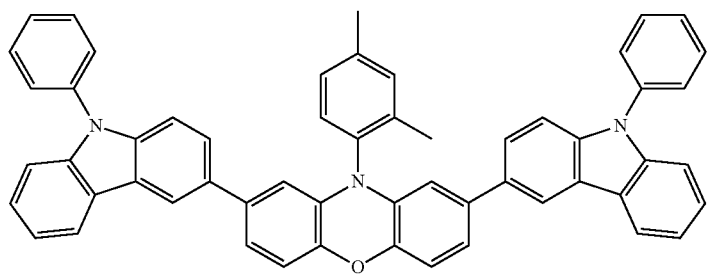 [SMILES: Cc1ccc(N2c3cc(-c4ccc5c(c4)c4ccccc4n5-c4ccccc4)ccc3Oc3ccc(-c4ccc5c(c4)c4ccccc4n5-c4ccccc4)cc32)c(C)c1]
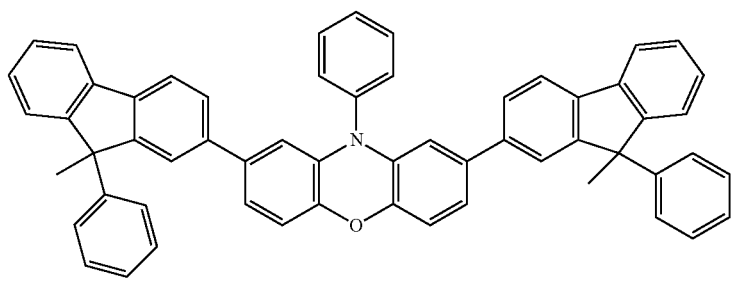 [SMILES: CC1(c2ccccc2)c2ccccc2-c2ccc(-c3ccc4c(c3)N(c3ccccc3)c3cc(-c5ccc6c(c5)C(C)(c5ccccc5)c5ccccc5-6)ccc3O4)cc21]
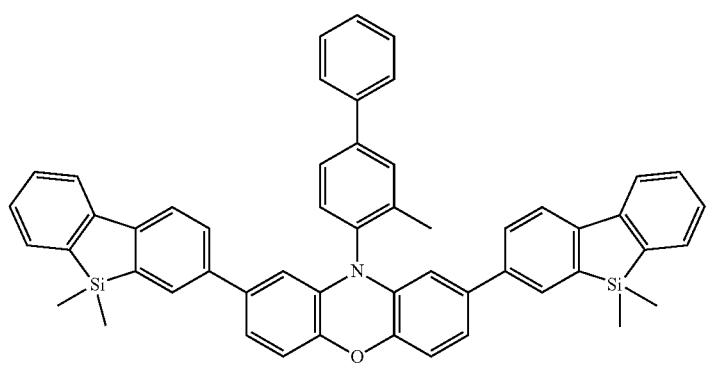 [SMILES: Cc1cc(-c2ccccc2)ccc1N1c2cc(-c3ccc4c(c3)[Si](C)(C)c3ccccc3-4)ccc2Oc2ccc(-c3ccc4c(c3)[Si](C)(C)c3ccccc3-4)cc21]
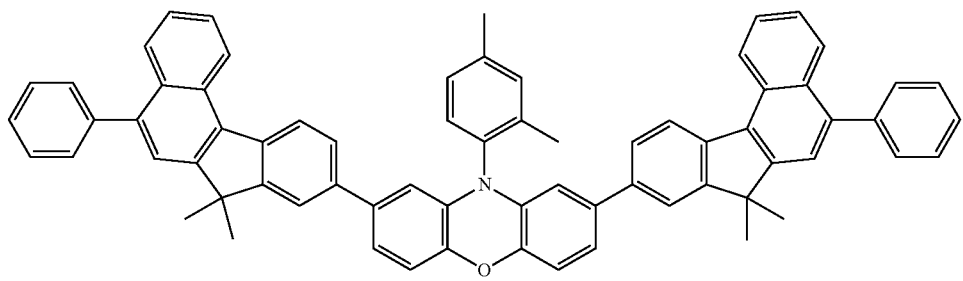 [SMILES: Cc1ccc(N2c3cc(-c4ccc5c(c4)C(C)(C)c4cc(-c6ccccc6)c6ccccc6c4-5)ccc3Oc3ccc(-c4ccc5c(c4)C(C)(C)c4cc(-c6ccccc6)c6ccccc6c4-5)cc32)c(C)c1]
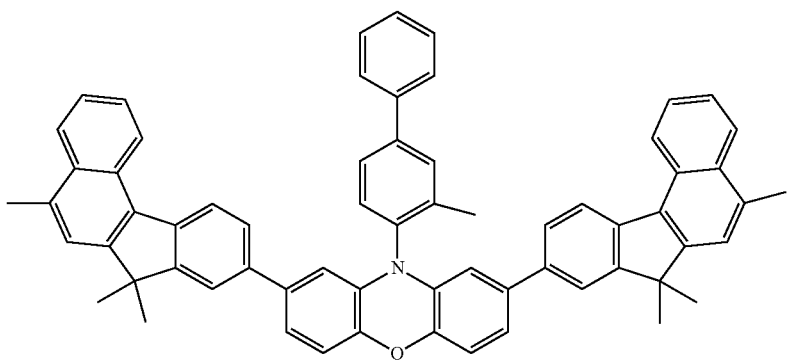

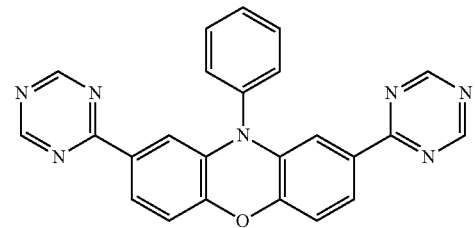 [SMILES: c1ccc(N2c3cc(-c4ncncn4)ccc3Oc3ccc(-c4ncncn4)cc32)cc1]
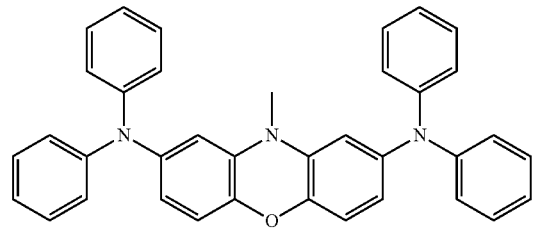 [SMILES: CN1c2cc(N(c3ccccc3)c3ccccc3)ccc2Oc2ccc(N(c3ccccc3)c3ccccc3)cc21]
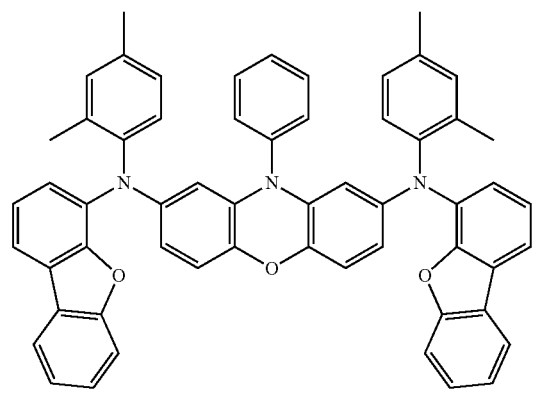 [SMILES: Cc1ccc(N(c2ccc3c(c2)N(c2ccccc2)c2cc(N(c4ccc(C)cc4C)c4cccc5c4oc4ccccc45)ccc2O3)c2cccc3c2oc2ccccc23)c(C)c1]
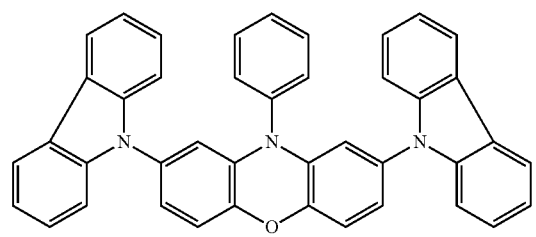 [SMILES: c1ccc(N2c3cc(-n4c5ccccc5c5ccccc54)ccc3Oc3ccc(-n4c5ccccc5c5ccccc54)cc32)cc1]
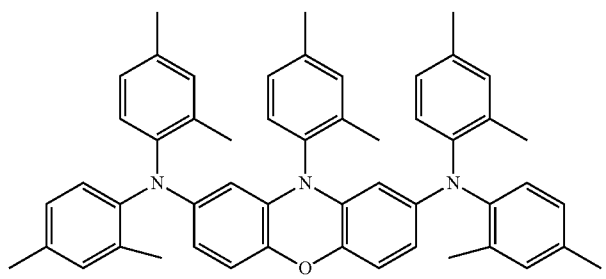

-continued
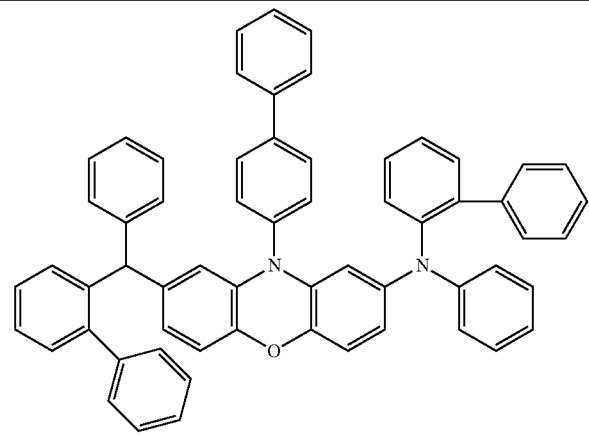
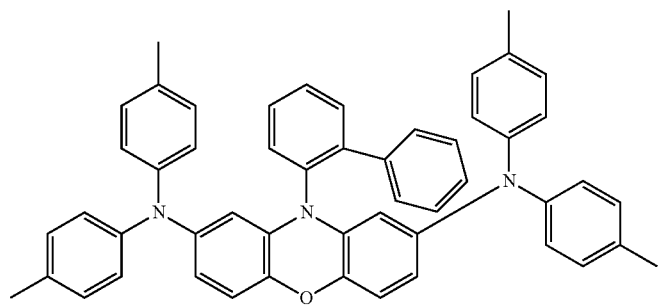
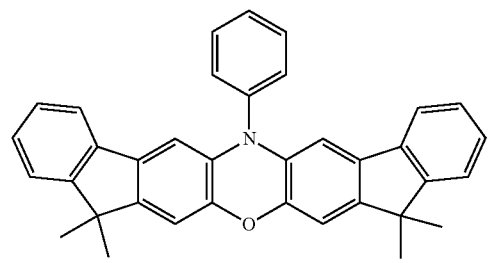 [SMILES: CC1(C)c2ccccc2-c2cc3c(cc21)Oc1cc2c(cc1N3c1ccccc1)-c1ccccc1C2(C)C]
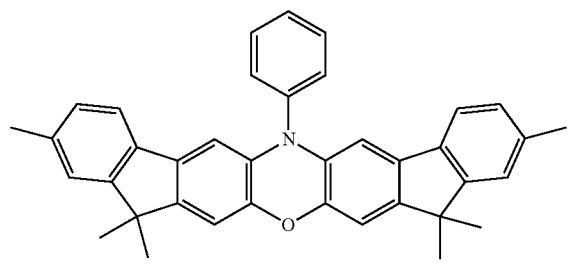
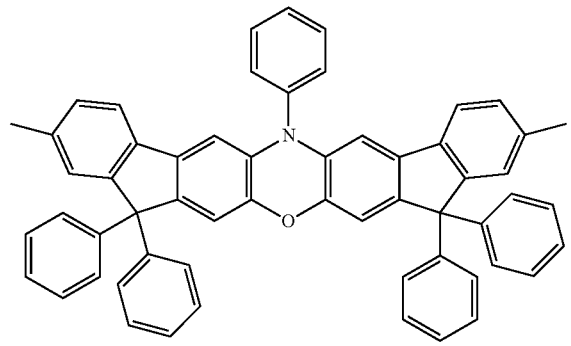

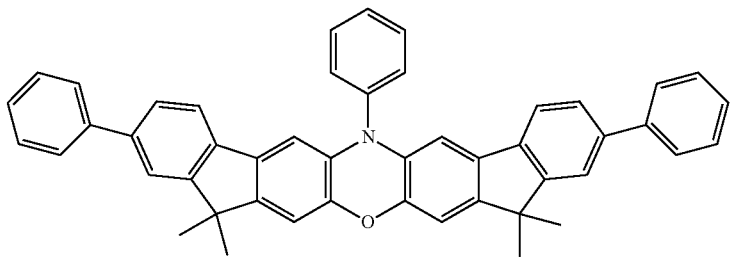 [SMILES: CC1(C)c2cc(-c3ccccc3)ccc2-c2cc3c(cc21)Oc1cc2c(cc1N3c1ccccc1)-c1ccc(-c3ccccc3)cc1C2(C)C]
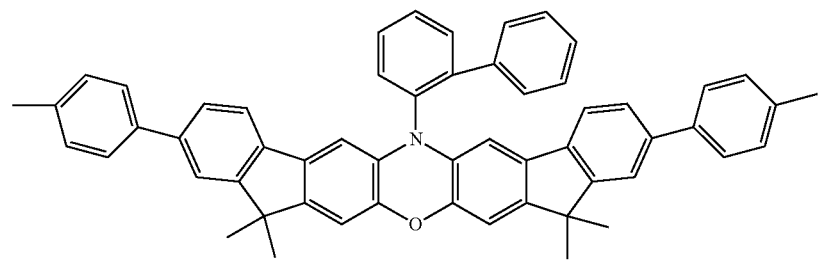
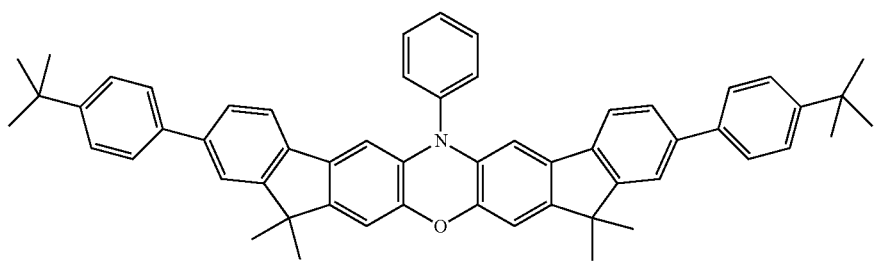 [SMILES: CC(C)(C)c1ccc(-c2ccc3c(c2)C(C)(C)c2cc4c(cc2-3)N(c2ccccc2)c2cc3c(cc2O4)C(C)(C)c2cc(-c4ccc(C(C)(C)C)cc4)ccc2-3)cc1]
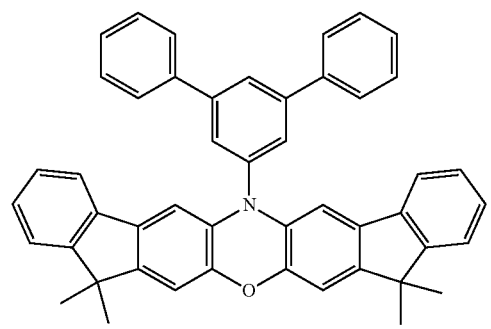 [SMILES: CC1(C)c2ccccc2-c2cc3c(cc21)Oc1cc2c(cc1N3c1cc(-c3ccccc3)cc(-c3ccccc3)c1)-c1ccccc1C2(C)C]
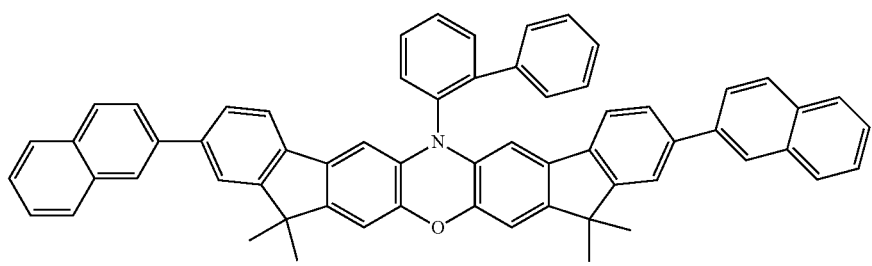 [SMILES: CC1(C)c2cc(-c3ccc4ccccc4c3)ccc2-c2cc3c(cc21)Oc1cc2c(cc1N3c1ccccc1-c1ccccc1)-c1ccc(-c3ccc4ccccc4c3)cc1C2(C)C]

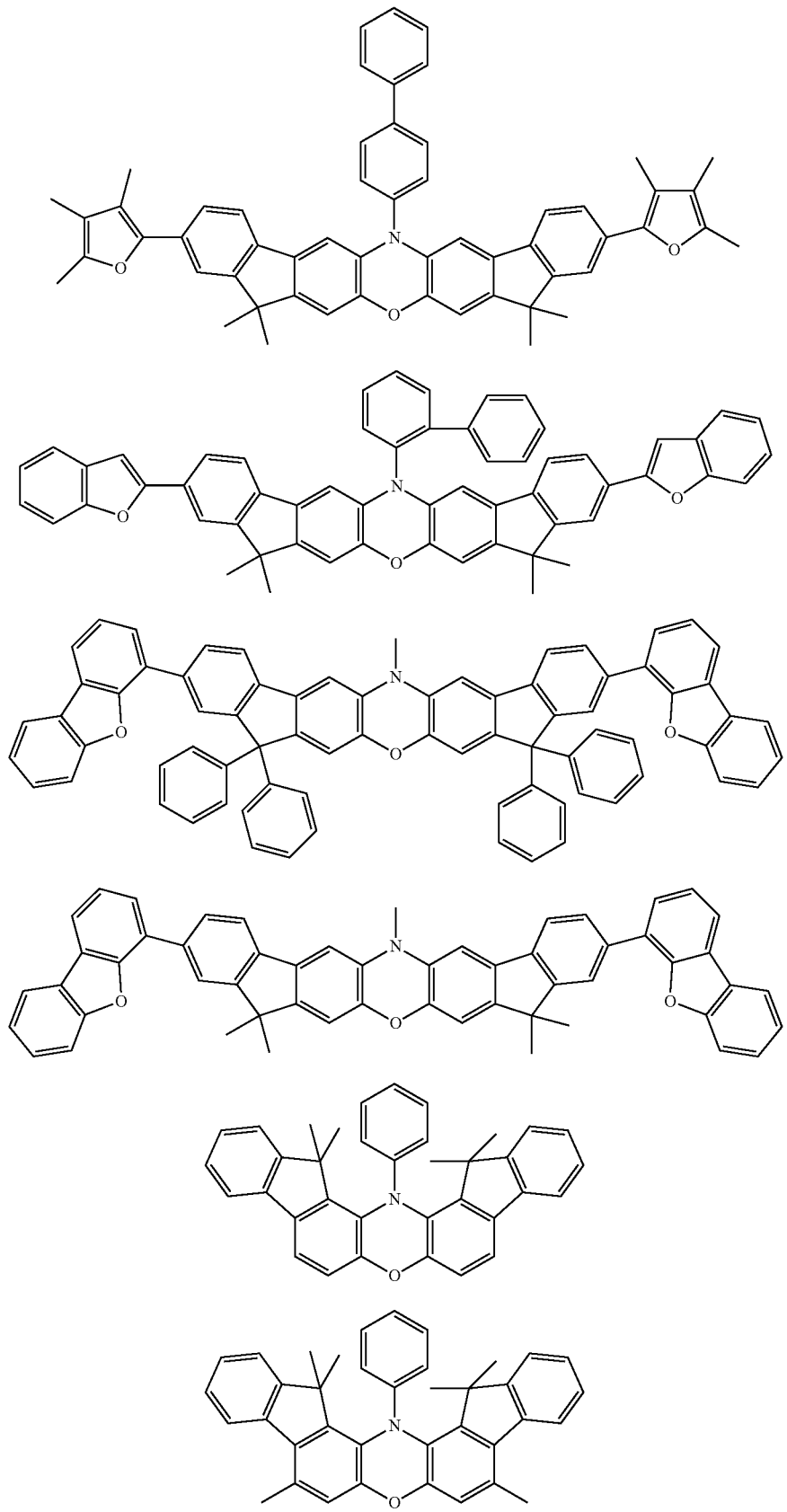

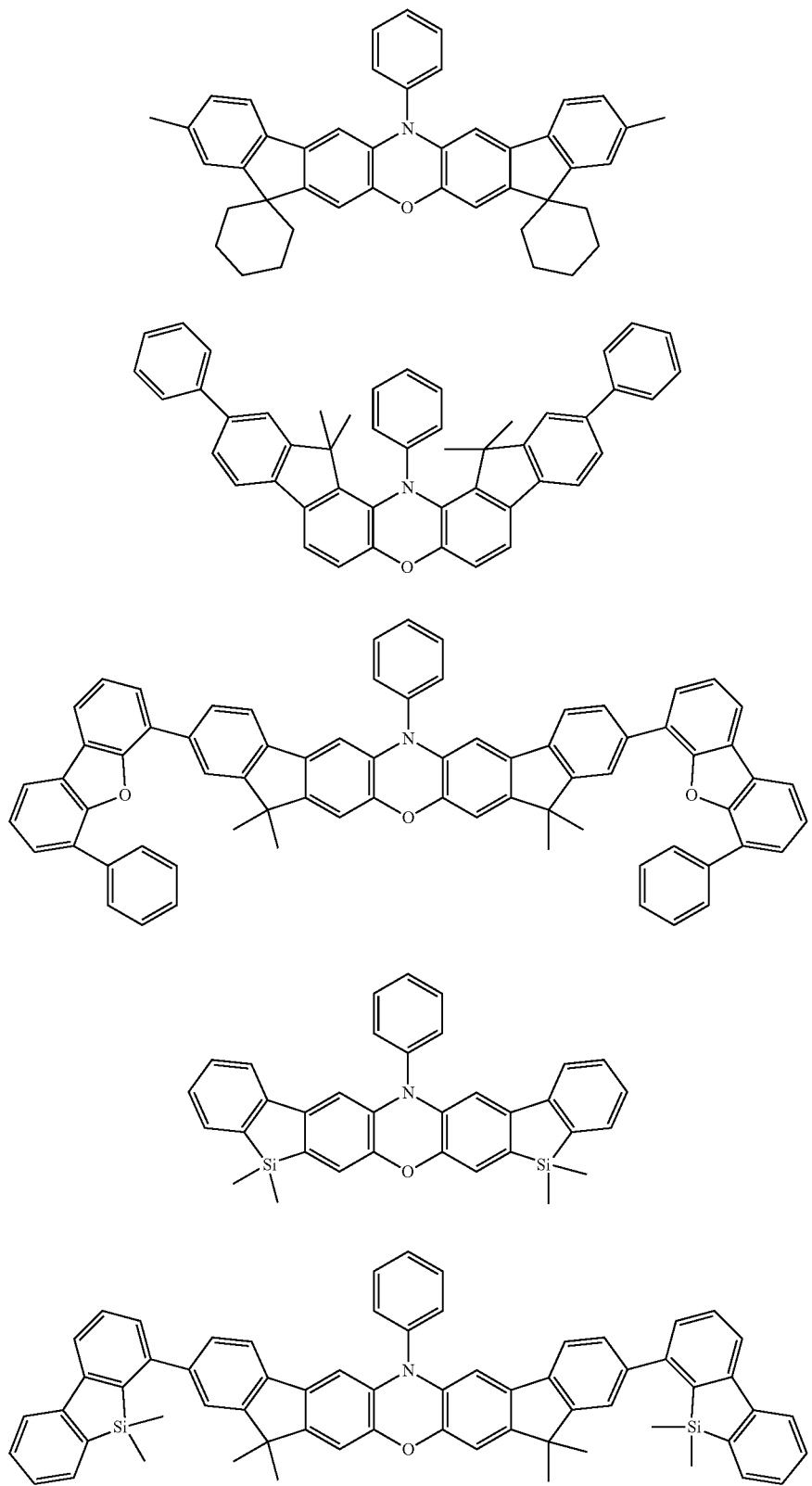

-continued
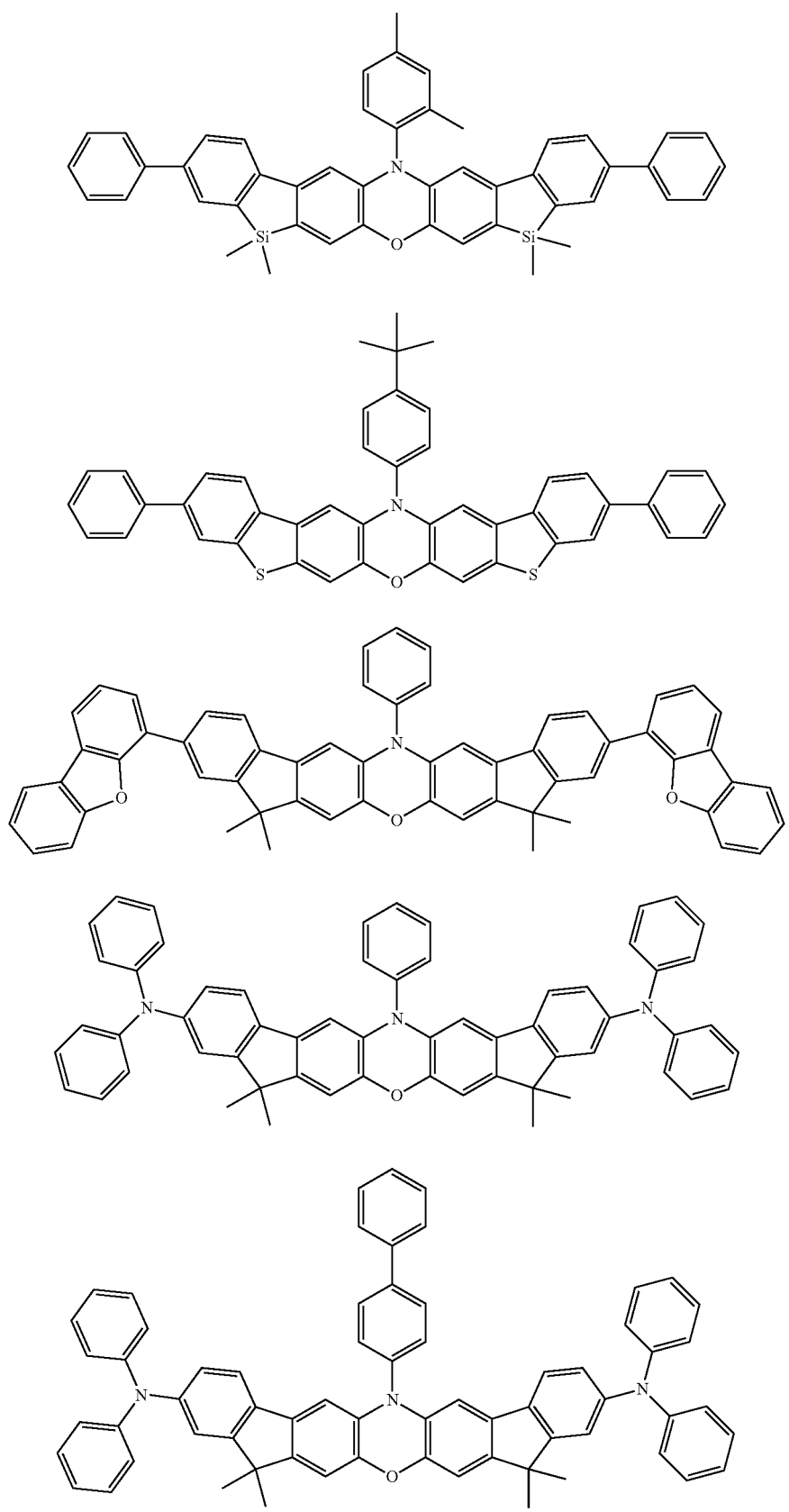

-continued
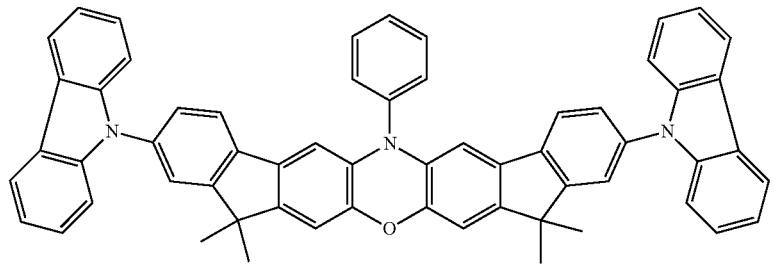 [SMILES: CC1(C)c2cc(-n3c4ccccc4c4ccccc43)ccc2-c2cc3c(cc21)Oc1cc2c(cc1N3c1ccccc1)-c1ccc(-n3c4ccccc4c4ccccc43)cc1C2(C)C]
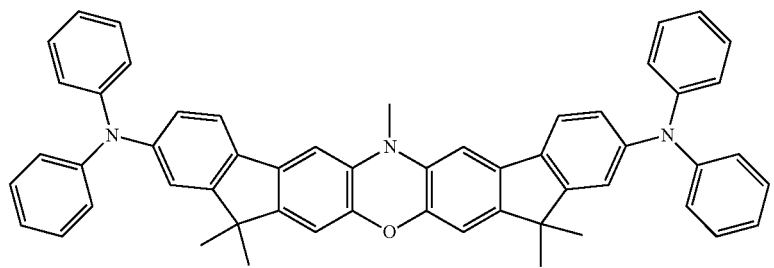 [SMILES: CN1c2cc3c(cc2Oc2cc4c(cc21)-c1ccc(N(c2ccccc2)c2ccccc2)cc1C4(C)C)C(C)(C)c1cc(N(c2ccccc2)c2ccccc2)ccc1-3]
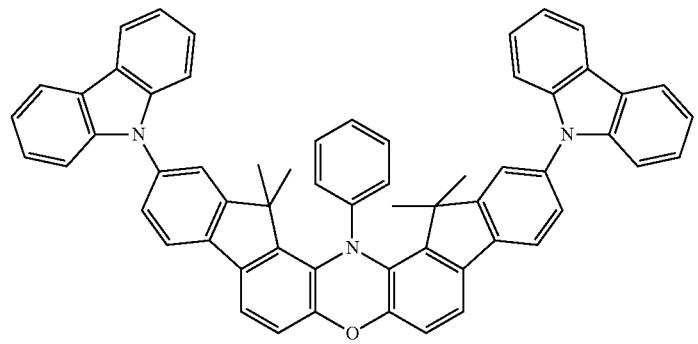 [SMILES: CC1(C)c2cc(-n3c4ccccc4c4ccccc43)ccc2-c2ccc3c(c21)N(c1ccccc1)c1c(ccc2c1C(C)(C)c1cc(-n4c5ccccc5c5ccccc54)ccc1-2)O3]
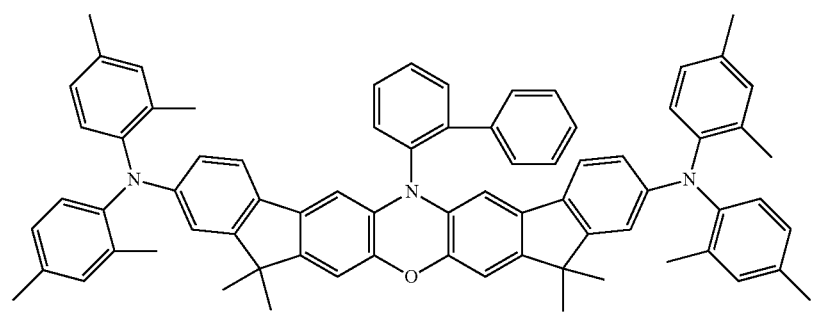

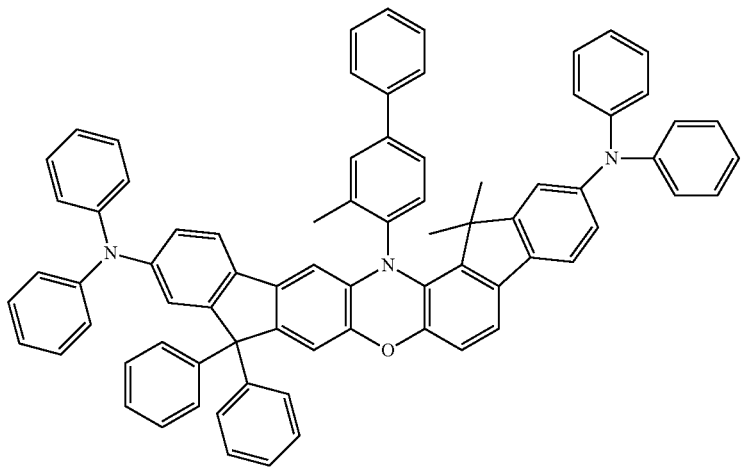 [SMILES: Cc1cc(-c2ccccc2)ccc1N1c2cc3c(cc2Oc2ccc4c(c21)C(C)(C)c1cc(N(c2ccccc2)c2ccccc2)ccc1-4)C(c1ccccc1)(c1ccccc1)c1cc(N(c2ccccc2)c2ccccc2)ccc1-3]
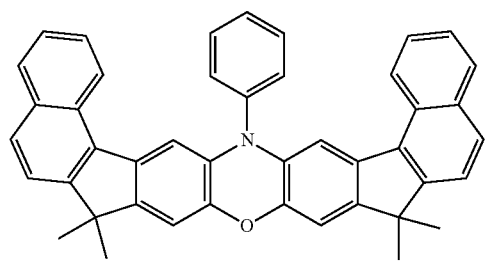 [SMILES: CC1(C)c2cc3c(cc2-c2c1ccc1ccccc21)N(c1ccccc1)c1cc2c(cc1O3)C(C)(C)c1ccc3ccccc3c1-2]
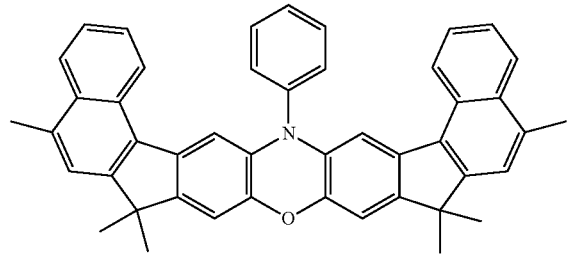
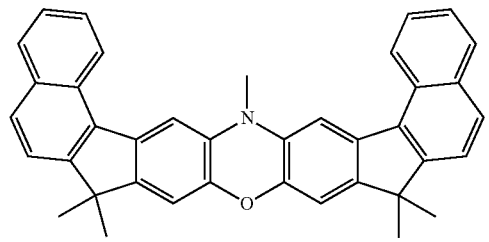 [SMILES: CN1c2cc3c(cc2Oc2cc4c(cc21)-c1c(ccc2ccccc12)C4(C)C)C(C)(C)c1ccc2ccccc2c1-3]
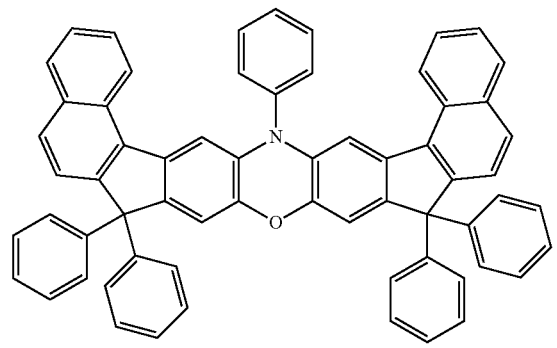 [SMILES: c1ccc(N2c3cc4c(cc3Oc3cc5c(cc32)-c2c(ccc3ccccc23)C5(c2ccccc2)c2ccccc2)C(c2ccccc2)(c2ccccc2)c2ccc3ccccc3c2-4)cc1]

-continued
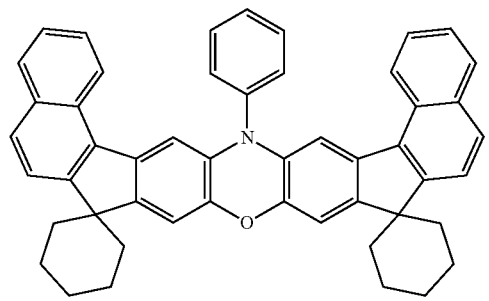 [SMILES: c1ccc(N2c3cc4c(cc3Oc3cc5c(cc32)-c2c(ccc3ccccc23)C52CCCCC2)C2(CCCCC2)c2ccc3ccccc3c2-4)cc1]
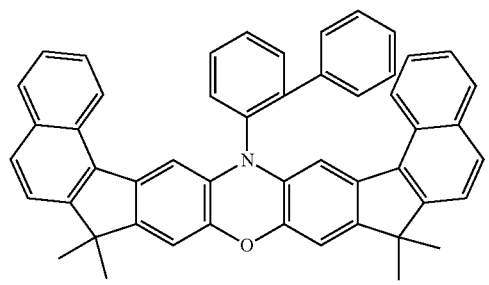 [SMILES: CC1(C)c2cc3c(cc2-c2c1ccc1ccccc21)N(c1ccccc1-c1ccccc1)c1cc2c(cc1O3)C(C)(C)c1ccc3ccccc3c1-2]
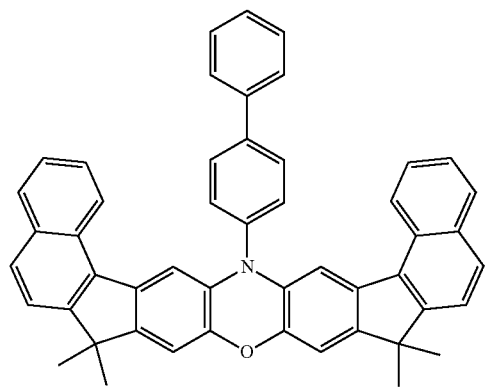 [SMILES: CC1(C)c2cc3c(cc2-c2c1ccc1ccccc21)N(c1ccc(-c2ccccc2)cc1)c1cc2c(cc1O3)C(C)(C)c1ccc3ccccc3c1-2]
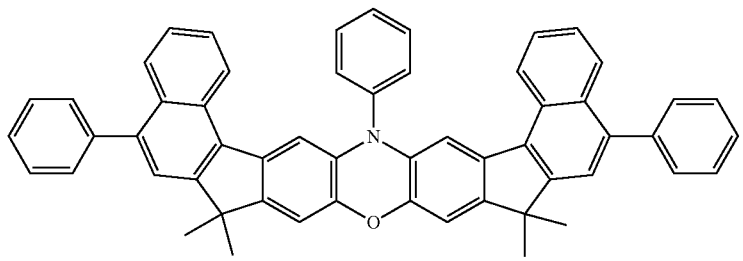 [SMILES: CC1(C)c2cc3c(cc2-c2c1cc(-c1ccccc1)c1ccccc21)N(c1ccccc1)c1cc2c(cc1O3)C(C)(C)c1cc(-c3ccccc3)c3ccccc3c1-2]
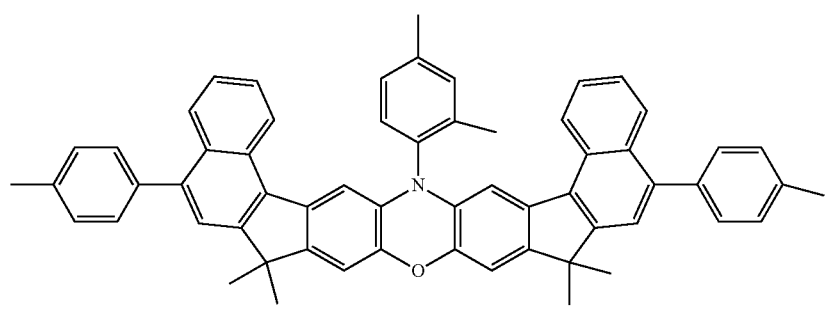

-continued
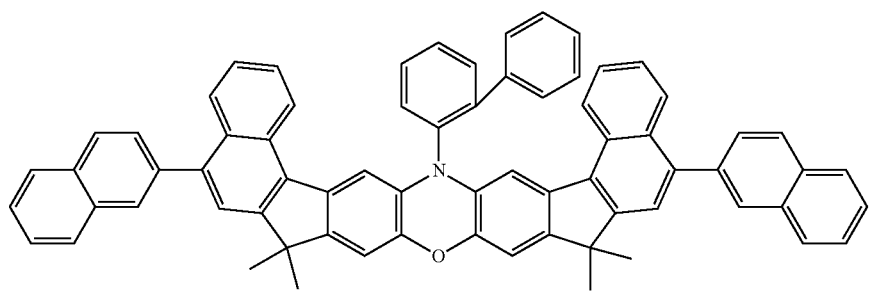 [SMILES: CC1(C)c2cc3c(cc2-c2c1cc(-c1ccc4ccccc4c1)c1ccccc21)N(c1ccccc1-c1ccccc1)c1cc2c(cc1O3)C(C)(C)c1cc(-c3ccc4ccccc4c3)c3ccccc3c1-2]
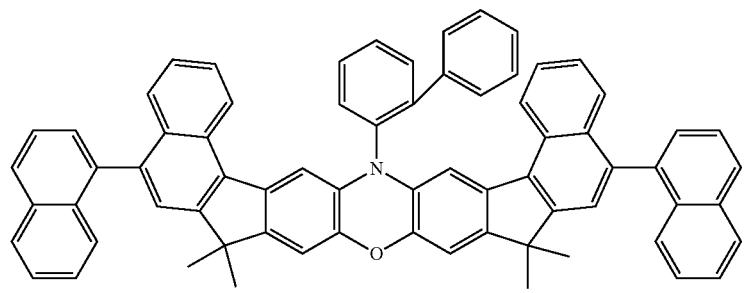 [SMILES: CC1(C)c2cc3c(cc2-c2c1cc(-c1cccc4ccccc14)c1ccccc21)N(c1ccccc1-c1ccccc1)c1cc2c(cc1O3)C(C)(C)c1cc(-c3cccc4ccccc34)c3ccccc3c1-2]
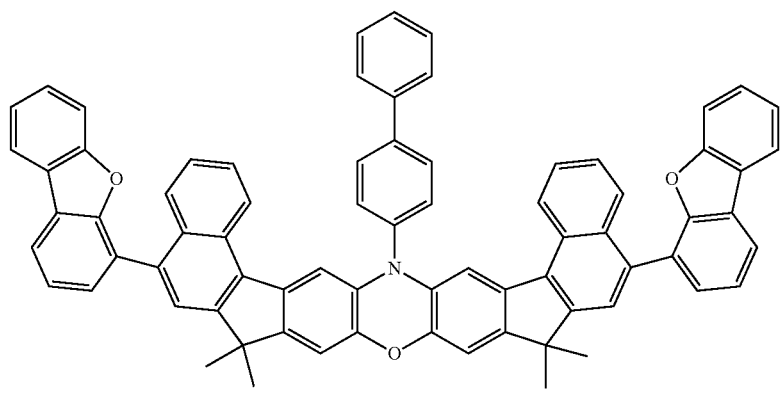 [SMILES: CC1(C)c2cc3c(cc2-c2c1cc(-c1cccc4c1oc1ccccc14)c1ccccc21)N(c1ccc(-c2ccccc2)cc1)c1cc2c(cc1O3)C(C)(C)c1cc(-c3cccc4c3oc3ccccc34)c3ccccc3c1-2]
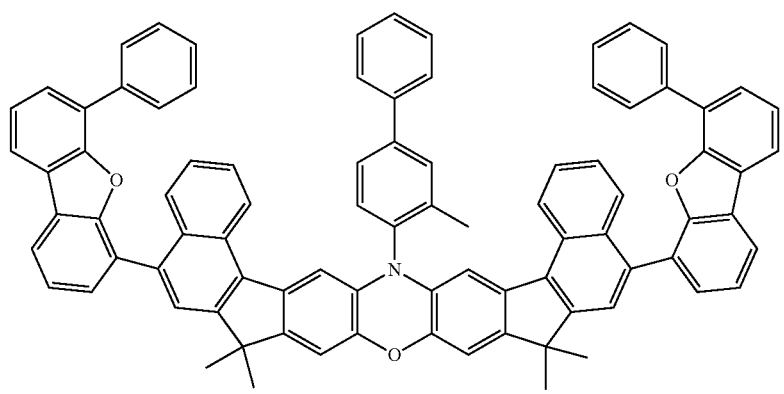 [SMILES: Cc1cc(-c2ccccc2)ccc1N1c2cc3c(cc2Oc2cc4c(cc21)-c1c(cc(-c2cccc5c2oc2c(-c6ccccc6)cccc25)c2ccccc12)C4(C)C)C(C)(C)c1cc(-c2cccc4c2oc2c(-c5ccccc5)cccc24)c2ccccc2c1-3]

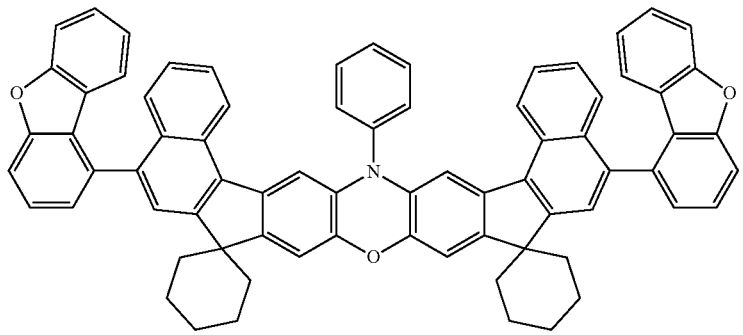 [SMILES: c1ccc(N2c3cc4c(cc3Oc3cc5c(cc32)-c2c(cc(-c3cccc6oc7ccccc7c36)c3ccccc23)C52CCCCC2)C2(CCCCC2)c2cc(-c3cccc5oc6ccccc6c35)c3ccccc3c2-4)cc1]
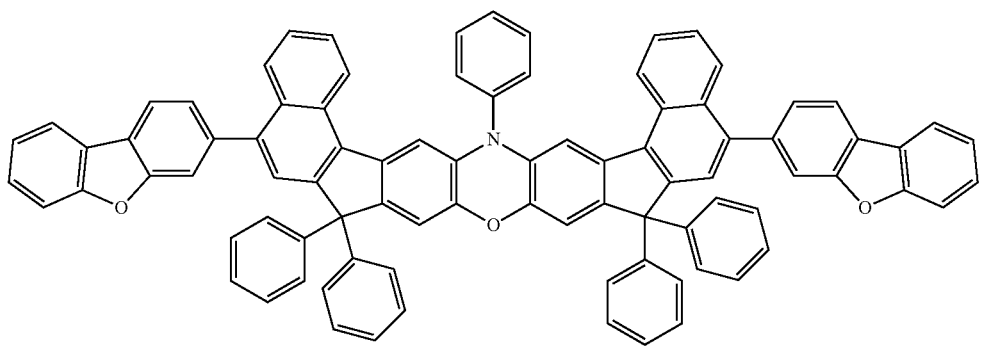 [SMILES: c1ccc(N2c3cc4c(cc3Oc3cc5c(cc32)-c2c(cc(-c3ccc6c(c3)oc3ccccc36)c3ccccc23)C5(c2ccccc2)c2ccccc2)C(c2ccccc2)(c2ccccc2)c2cc(-c3ccc5c(c3)oc3ccccc35)c3ccccc3c2-4)cc1]
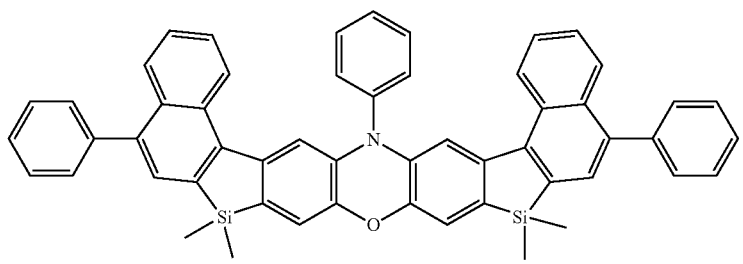 [SMILES: C[Si]1(C)c2cc3c(cc2-c2c1cc(-c1ccccc1)c1ccccc21)N(c1ccccc1)c1cc2c(cc1O3)[Si](C)(C)c1cc(-c3ccccc3)c3ccccc3c1-2]
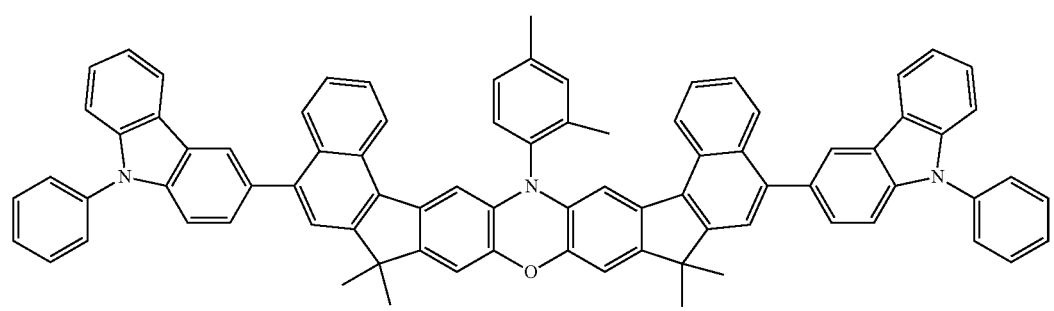 [SMILES: Cc1ccc(N2c3cc4c(cc3Oc3cc5c(cc32)-c2c(cc(-c3ccc6c(c3)c3ccccc3n6-c3ccccc3)c3ccccc23)C5(C)C)C(C)(C)c2cc(-c3ccc5c(c3)c3ccccc3n5-c3ccccc3)c3ccccc3c2-4)c(C)c1]
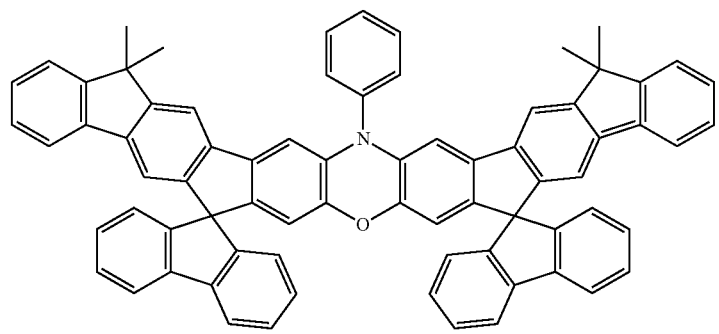

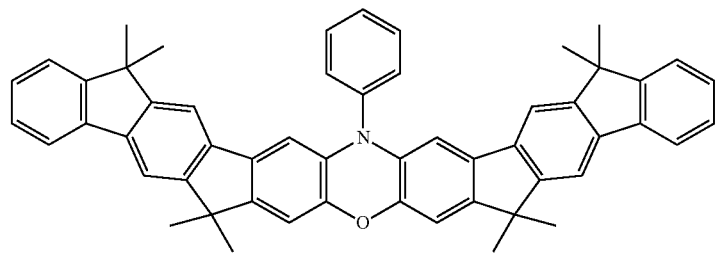 [SMILES: CC1(C)c2ccccc2-c2cc3c(cc21)-c1cc2c(cc1C3(C)C)Oc1cc3c(cc1N2c1ccccc1)-c1cc2c(cc1C3(C)C)-c1ccccc1C2(C)C]
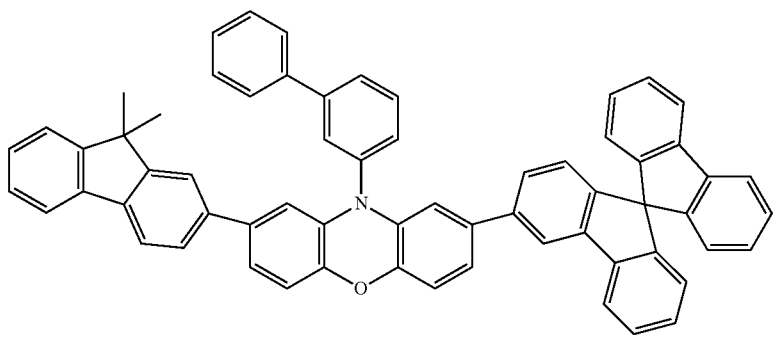 [SMILES: CC1(C)c2ccccc2-c2ccc(-c3ccc4c(c3)N(c3cccc(-c5ccccc5)c3)c3cc(-c5ccc6c(c5)-c5ccccc5C65c6ccccc6-c6ccccc65)ccc3O4)cc21]
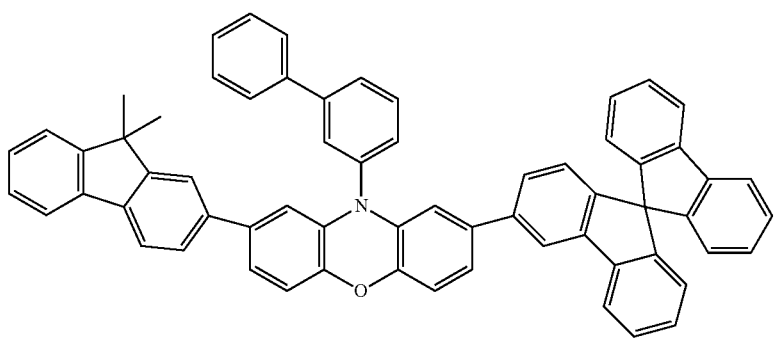 [SMILES: CC1(C)c2ccccc2-c2ccc(-c3ccc4c(c3)N(c3cccc(-c5ccccc5)c3)c3cc(-c5ccc6c(c5)-c5ccccc5C65c6ccccc6-c6ccccc65)ccc3O4)cc21]
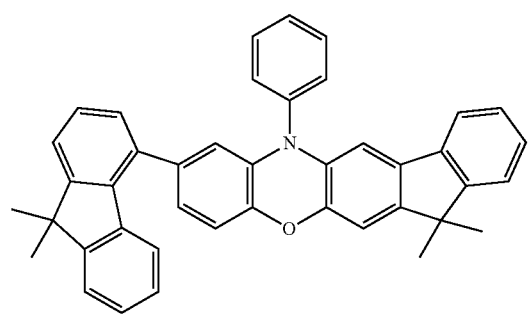 [SMILES: CC1(C)c2ccccc2-c2cc3c(cc21)Oc1ccc(-c2cccc4c2-c2ccccc2C4(C)C)cc1N3c1ccccc1]
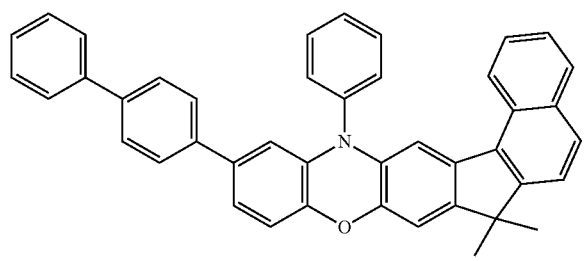 [SMILES: CC1(C)c2cc3c(cc2-c2c1ccc1ccccc21)N(c1ccccc1)c1cc(-c2ccc(-c4ccccc4)cc2)ccc1O3]

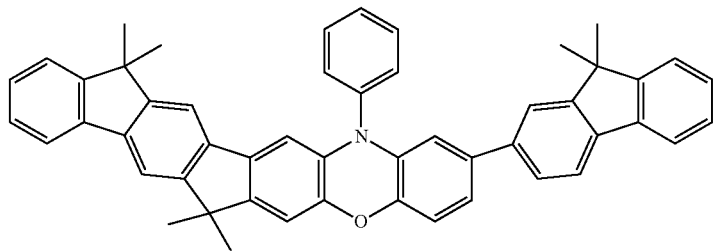 [SMILES: CC1(C)c2ccccc2-c2ccc(-c3ccc4c(c3)N(c3ccccc3)c3cc5c(cc3O4)C(C)(C)c3cc4c(cc3-5)C(C)(C)c3ccccc3-4)cc21]
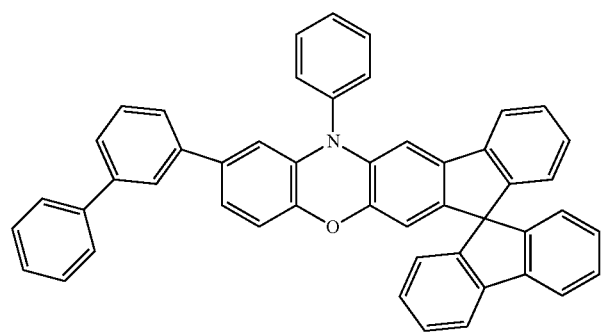 [SMILES: c1ccc(-c2cccc(-c3ccc4c(c3)N(c3ccccc3)c3cc5c(cc3O4)C3(c4ccccc4-c4ccccc43)c3ccccc3-5)c2)cc1]
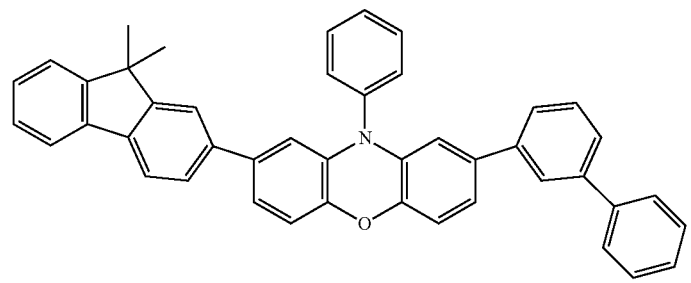 [SMILES: CC1(C)c2ccccc2-c2ccc(-c3ccc4c(c3)N(c3ccccc3)c3cc(-c5cccc(-c6ccccc6)c5)ccc3O4)cc21]
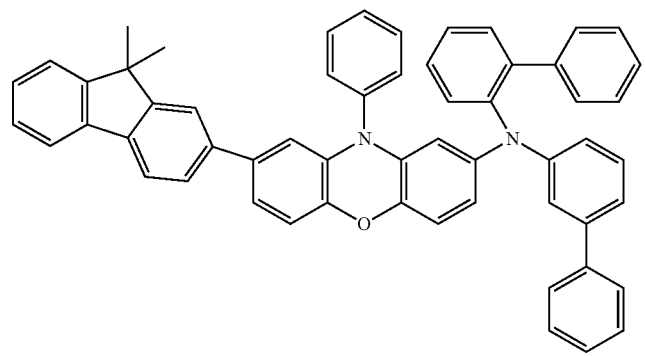 [SMILES: CC1(C)c2ccccc2-c2ccc(-c3ccc4c(c3)N(c3ccccc3)c3cc(N(c5cccc(-c6ccccc6)c5)c5ccccc5-c5ccccc5)ccc3O4)cc21]

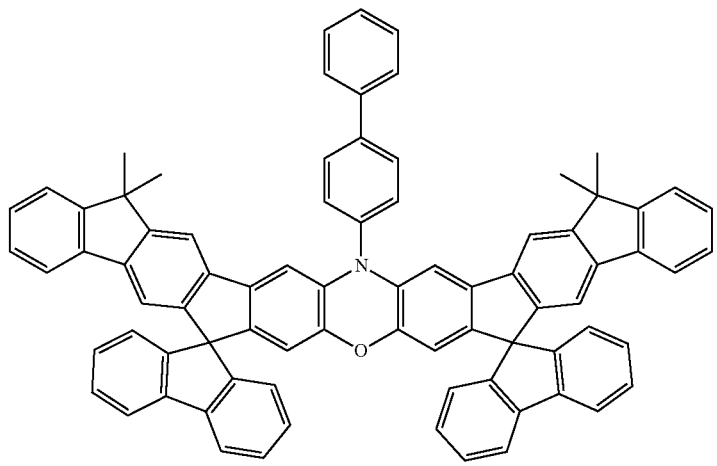 [SMILES: CC1(C)c2ccccc2-c2cc3c(cc21)-c1cc2c(cc1C31c3ccccc3-c3ccccc31)Oc1cc3c(cc1N2c1ccc(-c2ccccc2)cc1)-c1cc2c(cc1C31c3ccccc3-c3ccccc31)-c1ccccc1C2(C)C]
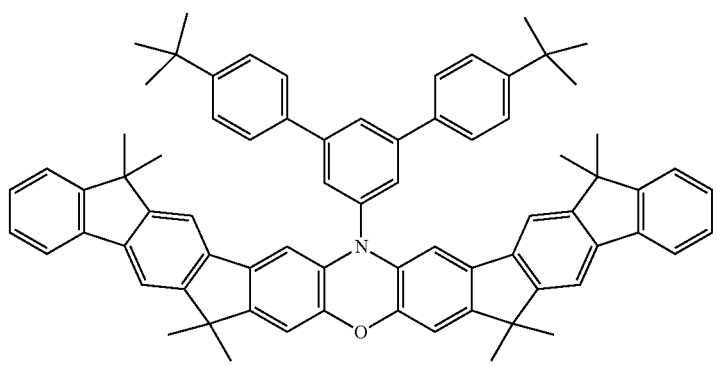 [SMILES: CC(C)(C)c1ccc(-c2cc(-c3ccc(C(C)(C)C)cc3)cc(N3c4cc5c(cc4Oc4cc6c(cc43)-c3cc4c(cc3C6(C)C)-c3ccccc3C4(C)C)C(C)(C)c3cc4c(cc3-5)C(C)(C)c3ccccc3-4)c2)cc1]
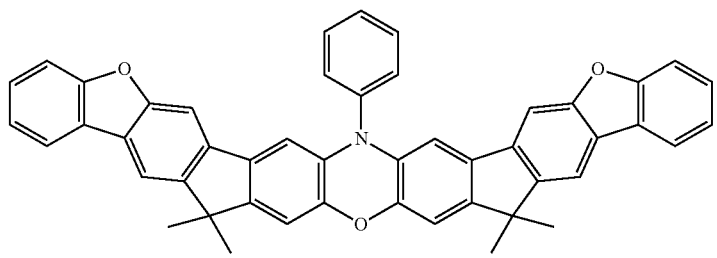 [SMILES: CC1(C)c2cc3c(cc2-c2cc4oc5ccccc5c4cc21)N(c1ccccc1)c1cc2c(cc1O3)C(C)(C)c1cc3c(cc1-2)oc1ccccc13]
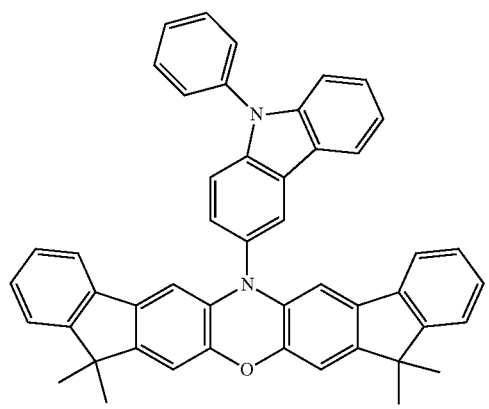 [SMILES: CC1(C)c2ccccc2-c2cc3c(cc21)Oc1cc2c(cc1N3c1ccc3c(c1)c1ccccc1n3-c1ccccc1)-c1ccccc1C2(C)C]

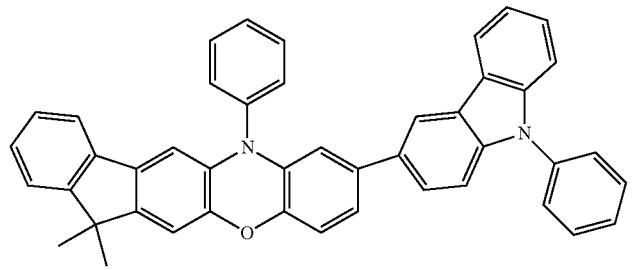 [SMILES: CC1(C)c2ccccc2-c2cc3c(cc21)Oc1ccc(-c2ccc4c(c2)c2ccccc2n4-c2ccccc2)cc1N3c1ccccc1]
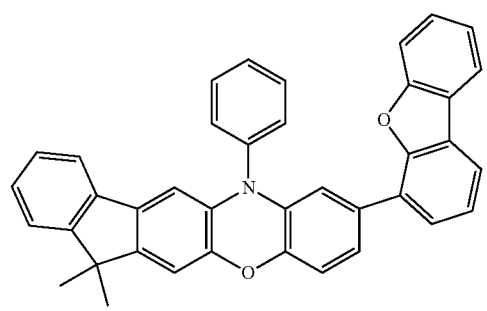 [SMILES: CC1(C)c2ccccc2-c2cc3c(cc21)Oc1ccc(-c2cccc4c2oc2ccccc24)cc1N3c1ccccc1]
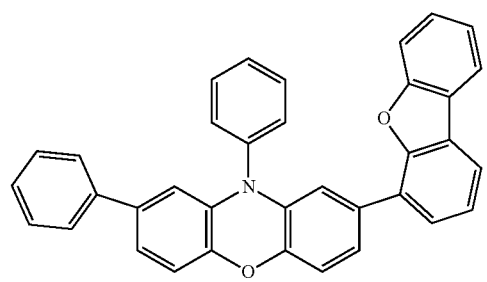 [SMILES: c1ccc(-c2ccc3c(c2)N(c2ccccc2)c2cc(-c4cccc5c4oc4ccccc45)ccc2O3)cc1]
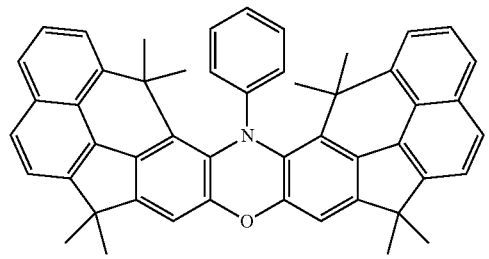 [SMILES: CC1(C)c2cc3c(c4c2-c2c1ccc1cccc(c21)C4(C)C)N(c1ccccc1)c1c(cc2c4c1C(C)(C)c1cccc5ccc(c-4c15)C2(C)C)O3]
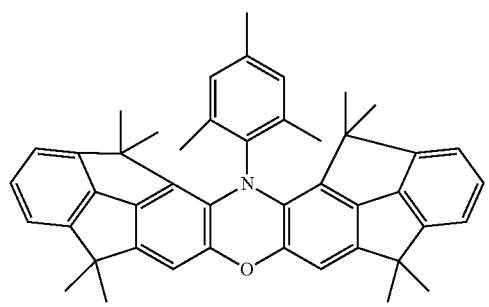 [SMILES: Cc1cc(C)c(N2c3c(cc4c5c3C(C)(C)c3cccc(c3-5)C4(C)C)Oc3cc4c5c(c32)C(C)(C)c2cccc(c2-5)C4(C)C)c(C)c1]

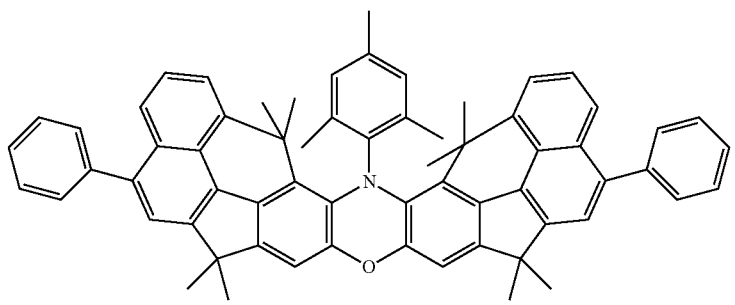 [SMILES: Cc1cc(C)c(N2c3c(cc4c5c3C(C)(C)c3cccc6c(-c7ccccc7)cc(c-5c36)C4(C)C)Oc3cc4c5c(c32)C(C)(C)c2cccc3c(-c6ccccc6)cc(c-5c23)C4(C)C)c(C)c1]
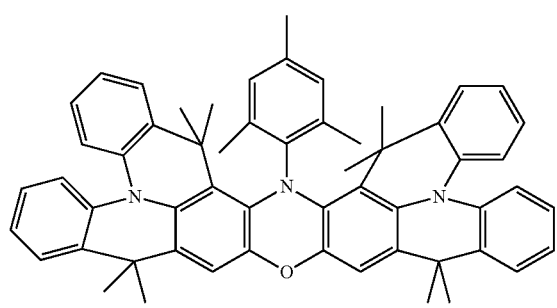 [SMILES: Cc1cc(C)c(N2c3c(cc4c5c3C(C)(C)c3ccccc3N5c3ccccc3C4(C)C)Oc3cc4c5c(c32)C(C)(C)c2ccccc2N5c2ccccc2C4(C)C)c(C)c1]
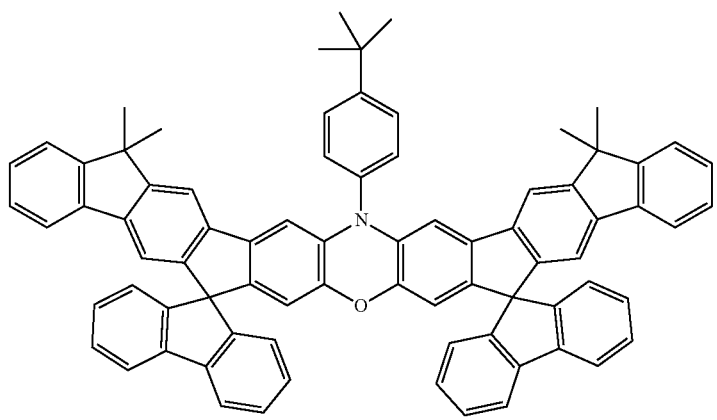 [SMILES: CC(C)(C)c1ccc(N2c3cc4c(cc3Oc3cc5c(cc32)-c2cc3c(cc2C52c5ccccc5-c5ccccc52)-c2ccccc2C3(C)C)C2(c3ccccc3-c3ccccc32)c2cc3c(cc2-4)C(C)(C)c2ccccc2-3)cc1]
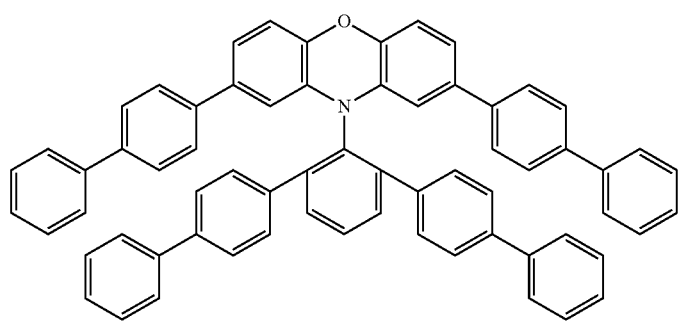 [SMILES: c1ccc(-c2ccc(-c3ccc4c(c3)N(c3c(-c5ccc(-c6ccccc6)cc5)cccc3-c3ccc(-c5ccccc5)cc3)c3cc(-c5ccc(-c6ccccc6)cc5)ccc3O4)cc2)cc1]

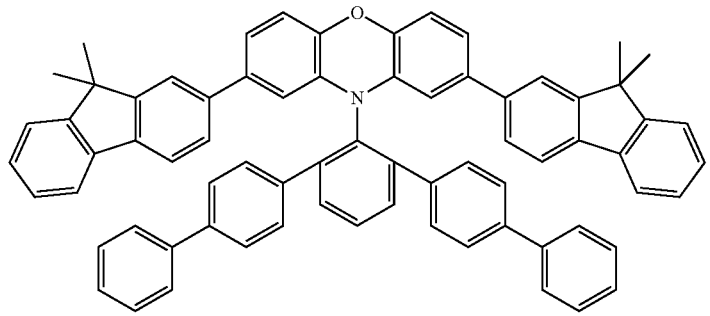 [SMILES: CC1(C)c2ccccc2-c2ccc(-c3ccc4c(c3)N(c3c(-c5ccc(-c6ccccc6)cc5)cccc3-c3ccc(-c5ccccc5)cc3)c3cc(-c5ccc6c(c5)C(C)(C)c5ccccc5-6)ccc3O4)cc21]
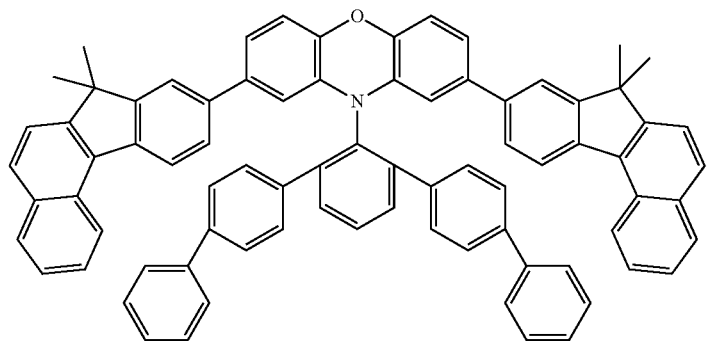 [SMILES: CC1(C)c2cc(-c3ccc4c(c3)N(c3c(-c5ccc(-c6ccccc6)cc5)cccc3-c3ccc(-c5ccccc5)cc3)c3cc(-c5ccc6c(c5)C(C)(C)c5ccc7ccccc7c5-6)ccc3O4)ccc2-c2c1ccc1ccccc21]
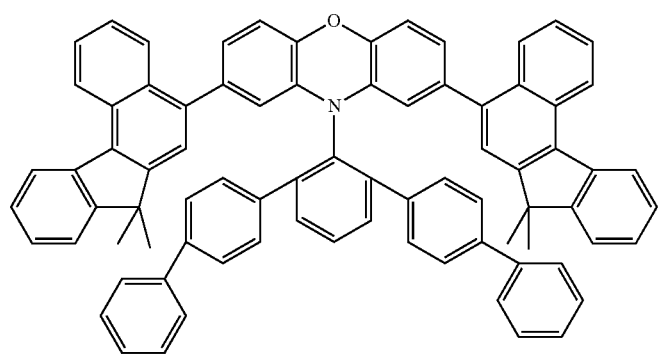 [SMILES: CC1(C)c2ccccc2-c2c1cc(-c1ccc3c(c1)N(c1c(-c4ccc(-c5ccccc5)cc4)cccc1-c1ccc(-c4ccccc4)cc1)c1cc(-c4cc5c(c6ccccc46)-c4ccccc4C5(C)C)ccc1O3)c1ccccc21]
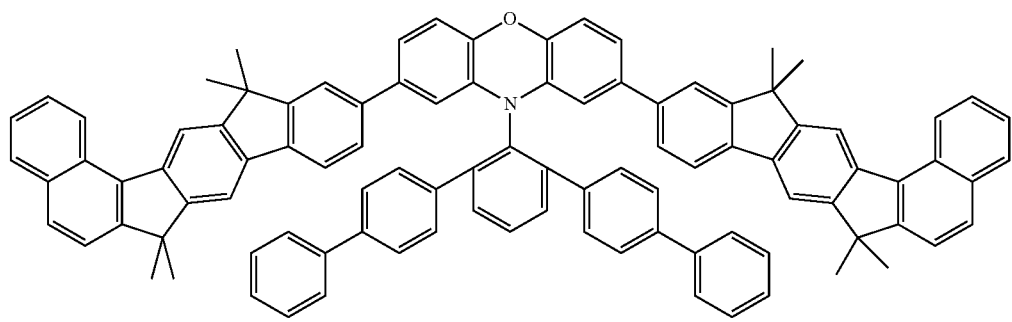 [SMILES: CC1(C)c2cc(-c3ccc4c(c3)N(c3c(-c5ccc(-c6ccccc6)cc5)cccc3-c3ccc(-c5ccccc5)cc3)c3cc(-c5ccc6c(c5)C(C)(C)c5cc7c(cc5-6)C(C)(C)c5ccc6ccccc6c5-7)ccc3O4)ccc2-c2cc3c(cc21)-c1c(ccc2ccccc12)C3(C)C]

-continued
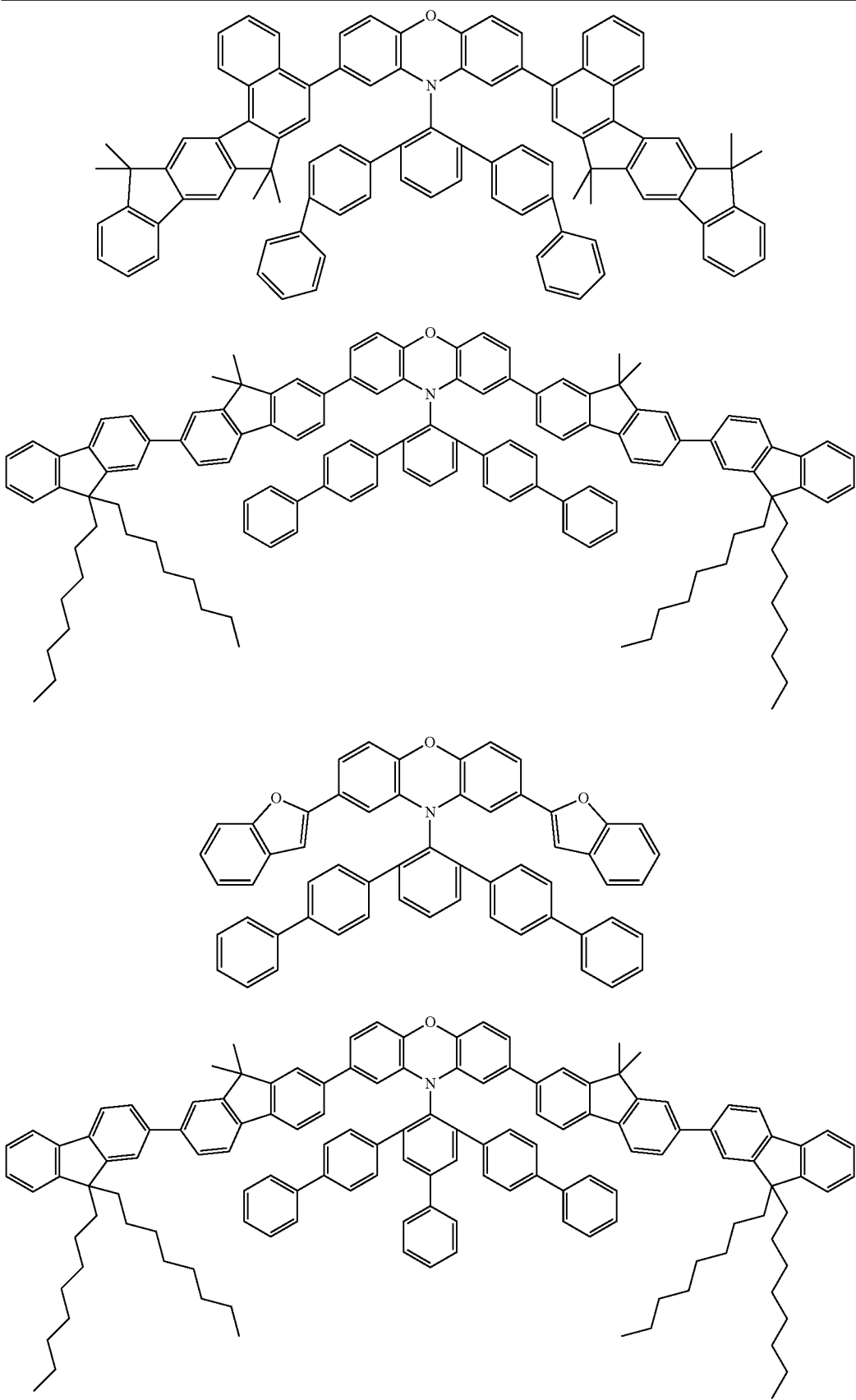

-continued
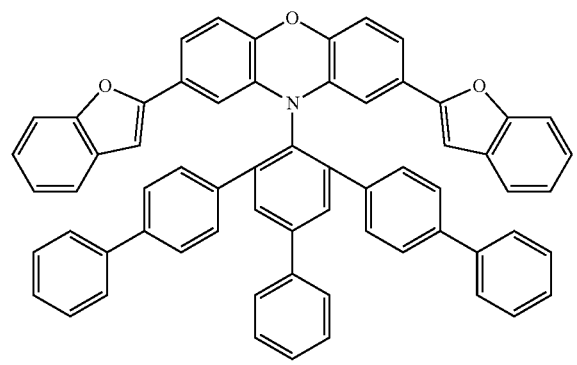 [SMILES: c1ccc(-c2ccc(-c3cc(-c4ccccc4)cc(-c4ccc(-c5ccccc5)cc4)c3N3c4cc(-c5cc6ccccc6o5)ccc4Oc4ccc(-c5cc6ccccc6o5)cc43)cc2)cc1]
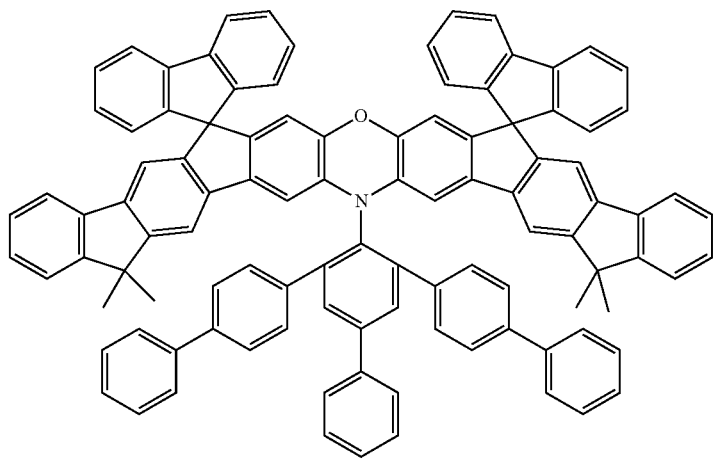 [SMILES: CC1(C)c2ccccc2-c2cc3c(cc21)-c1cc2c(cc1C31c3ccccc3-c3ccccc31)Oc1cc3c(cc1N2c1c(-c2ccc(-c4ccccc4)cc2)cc(-c2ccccc2)cc1-c1ccc(-c2ccccc2)cc1)-c1cc2c(cc1C31c3ccccc3-c3ccccc31)-c1ccccc1C2(C)C]
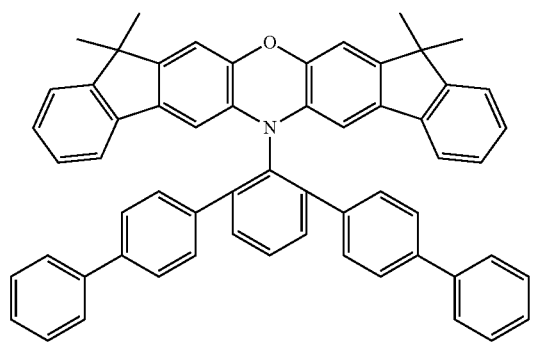 [SMILES: CC1(C)c2ccccc2-c2cc3c(cc21)Oc1cc2c(cc1N3c1c(-c3ccc(-c4ccccc4)cc3)cccc1-c1ccc(-c3ccccc3)cc1)-c1ccccc1C2(C)C]
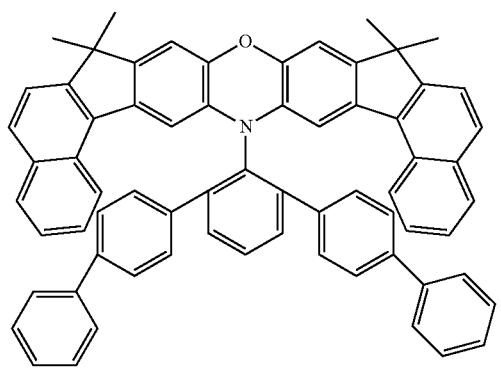 [SMILES: CC1(C)c2cc3c(cc2-c2c1ccc1ccccc21)N(c1c(-c2ccc(-c4ccccc4)cc2)cccc1-c1ccc(-c2ccccc2)cc1)c1cc2c(cc1O3)C(C)(C)c1ccc3ccccc3c1-2]

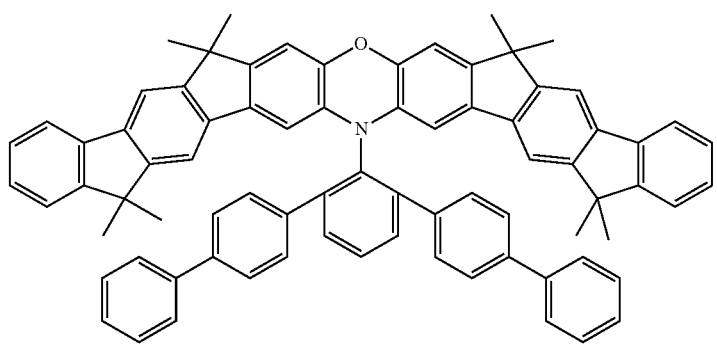 [SMILES: CC1(C)c2ccccc2-c2cc3c(cc21)-c1cc2c(cc1C3(C)C)Oc1cc3c(cc1N2c1c(-c2ccc(-c4ccccc4)cc2)cccc1-c1ccc(-c2ccccc2)cc1)-c1cc2c(cc1C3(C)C)-c1ccccc1C2(C)C]
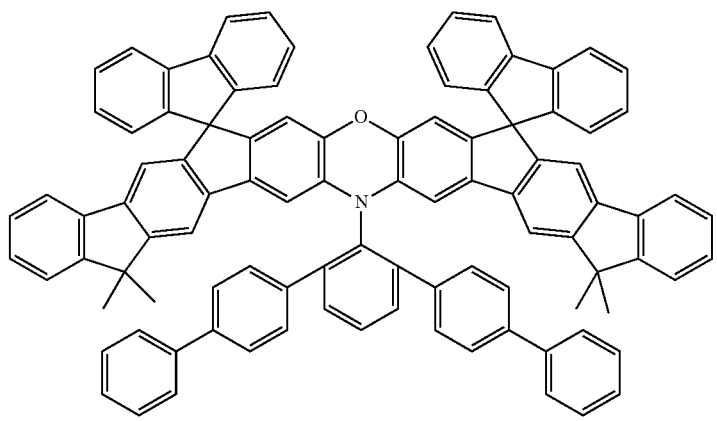 [SMILES: CC1(C)c2ccccc2-c2cc3c(cc21)-c1cc2c(cc1C31c3ccccc3-c3ccccc31)Oc1cc3c(cc1N2c1c(-c2ccc(-c4ccccc4)cc2)cccc1-c1ccc(-c2ccccc2)cc1)-c1cc2c(cc1C31c3ccccc3-c3ccccc31)-c1ccccc1C2(C)C]
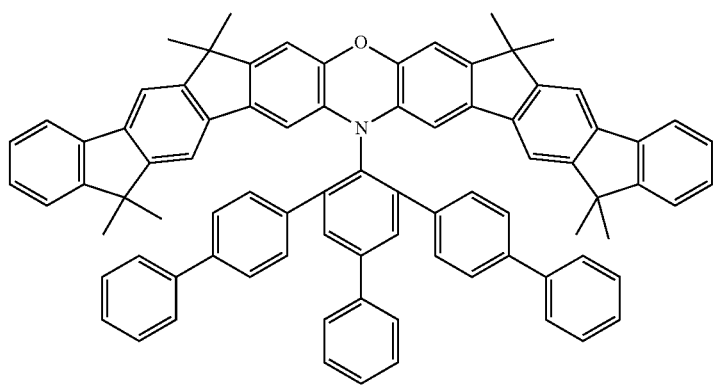 [SMILES: CC1(C)c2ccccc2-c2cc3c(cc21)-c1cc2c(cc1C3(C)C)Oc1cc3c(cc1N2c1c(-c2ccc(-c4ccccc4)cc2)cc(-c2ccccc2)cc1-c1ccc(-c2ccccc2)cc1)-c1cc2c(cc1C3(C)C)-c1ccccc1C2(C)C]
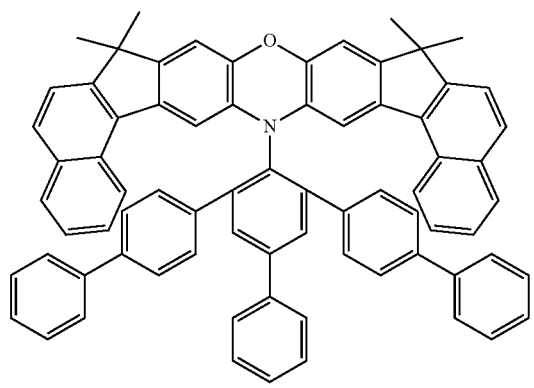 [SMILES: CC1(C)c2cc3c(cc2-c2c1ccc1ccccc21)N(c1c(-c2ccc(-c4ccccc4)cc2)cc(-c2ccccc2)cc1-c1ccc(-c2ccccc2)cc1)c1cc2c(cc1O3)C(C)(C)c1ccc3ccccc3c1-2]

-continued
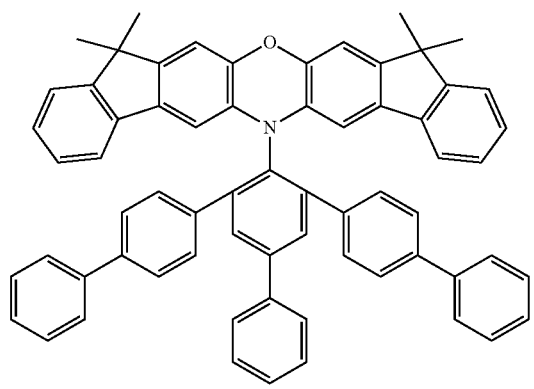 [SMILES: CC1(C)c2ccccc2-c2cc3c(cc21)Oc1cc2c(cc1N3c1c(-c3ccc(-c4ccccc4)cc3)cc(-c3ccccc3)cc1-c1ccc(-c3ccccc3)cc1)-c1ccccc1C2(C)C]
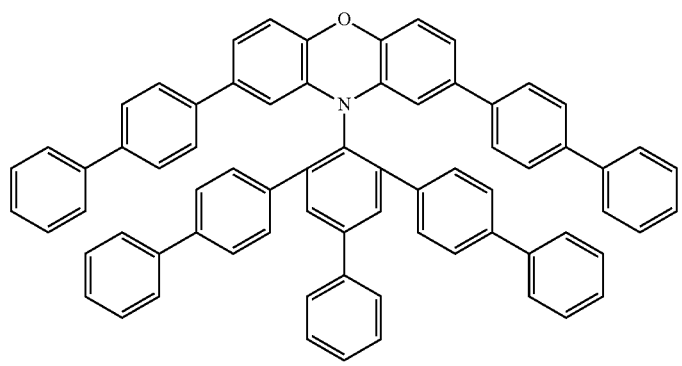 [SMILES: c1ccc(-c2ccc(-c3ccc4c(c3)N(c3c(-c5ccc(-c6ccccc6)cc5)cc(-c5ccccc5)cc3-c3ccc(-c5ccccc5)cc3)c3cc(-c5ccc(-c6ccccc6)cc5)ccc3O4)cc2)cc1]
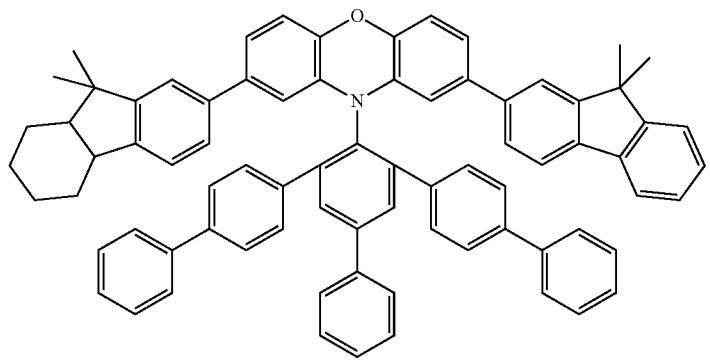 [SMILES: CC1(C)c2ccccc2-c2ccc(-c3ccc4c(c3)N(c3c(-c5ccc(-c6ccccc6)cc5)cc(-c5ccccc5)cc3-c3ccc(-c5ccccc5)cc3)c3cc(-c5ccc6c(c5)C(C)(C)C5CCCCC65)ccc3O4)cc21]
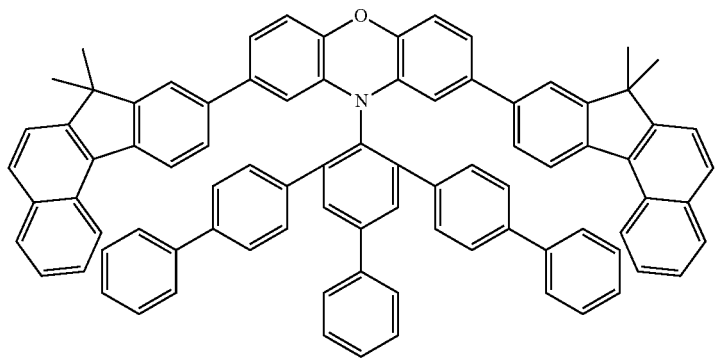 [SMILES: CC1(C)c2cc(-c3ccc4c(c3)N(c3c(-c5ccc(-c6ccccc6)cc5)cc(-c5ccccc5)cc3-c3ccc(-c5ccccc5)cc3)c3cc(-c5ccc6c(c5)C(C)(C)c5ccc7ccccc7c5-6)ccc3O4)ccc2-c2c1ccc1ccccc21]

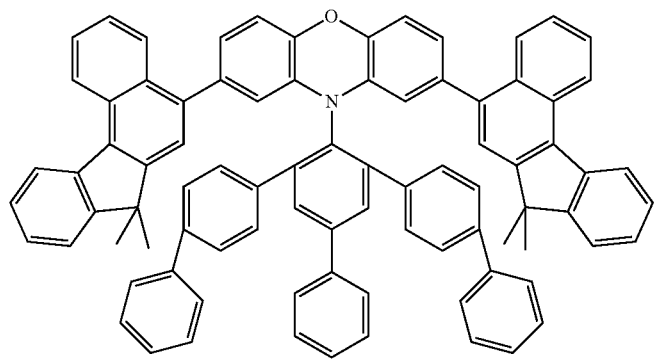 [SMILES: CC1(C)c2ccccc2-c2c1cc(-c1ccc3c(c1)N(c1c(-c4ccc(-c5ccccc5)cc4)cc(-c4ccccc4)cc1-c1ccc(-c4ccccc4)cc1)c1cc(-c4cc5c(c6ccccc46)-c4ccccc4C5(C)C)ccc1O3)c1ccccc21]
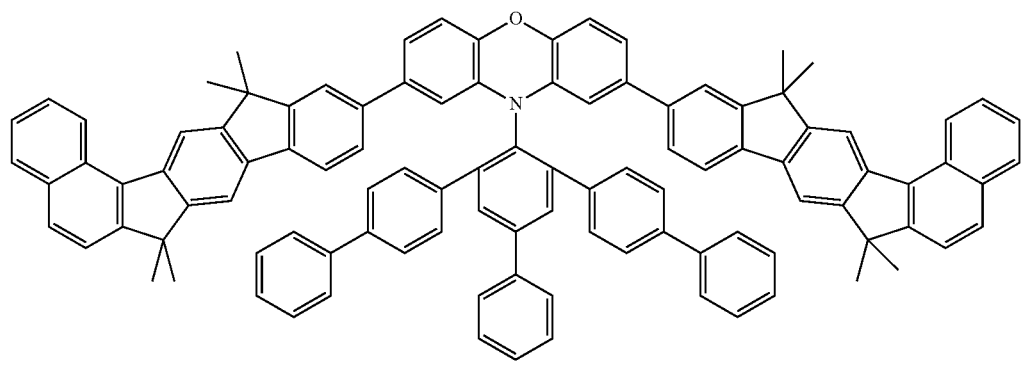 [SMILES: CC1(C)c2cc(-c3ccc4c(c3)N(c3c(-c5ccc(-c6ccccc6)cc5)cc(-c5ccccc5)cc3-c3ccc(-c5ccccc5)cc3)c3cc(-c5ccc6c(c5)C(C)(C)c5cc7c(cc5-6)C(C)(C)c5ccc6ccccc6c5-7)ccc3O4)ccc2-c2cc3c(cc21)-c1c(ccc2ccccc12)C3(C)C]
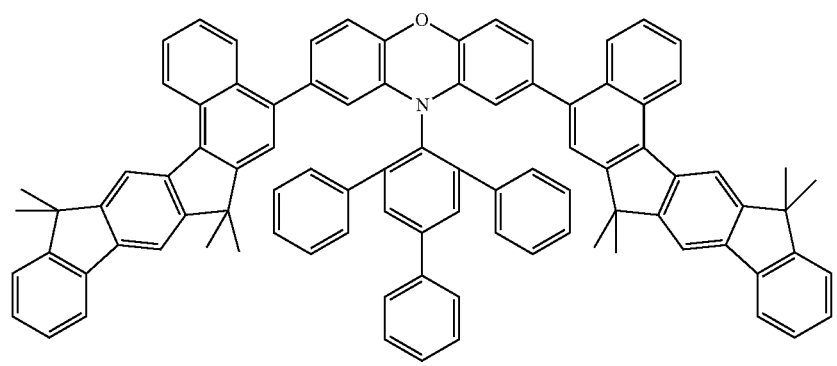 [SMILES: CC1(C)c2ccccc2-c2cc3c(cc21)-c1c(cc(-c2ccc4c(c2)N(c2c(-c5ccccc5)cc(-c5ccccc5)cc2-c2ccccc2)c2cc(-c5cc6c(c7ccccc57)-c5cc7c(cc5C6(C)C)-c5ccccc5C7(C)C)ccc2O4)c2ccccc12)C3(C)C]
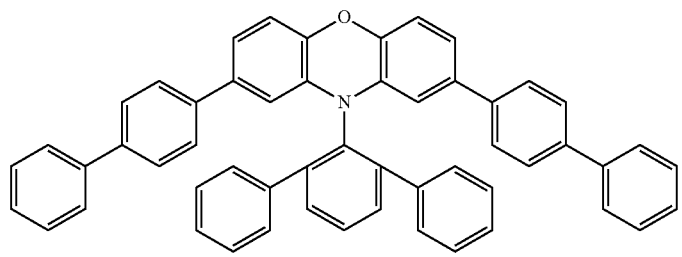 [SMILES: c1ccc(-c2ccc(-c3ccc4c(c3)N(c3c(-c5ccccc5)cccc3-c3ccccc3)c3cc(-c5ccc(-c6ccccc6)cc5)ccc3O4)cc2)cc1]
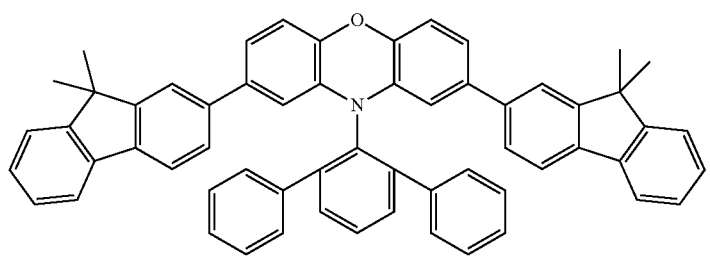 [SMILES: CC1(C)c2ccccc2-c2ccc(-c3ccc4c(c3)N(c3c(-c5ccccc5)cccc3-c3ccccc3)c3cc(-c5ccc6c(c5)C(C)(C)c5ccccc5-6)ccc3O4)cc21]

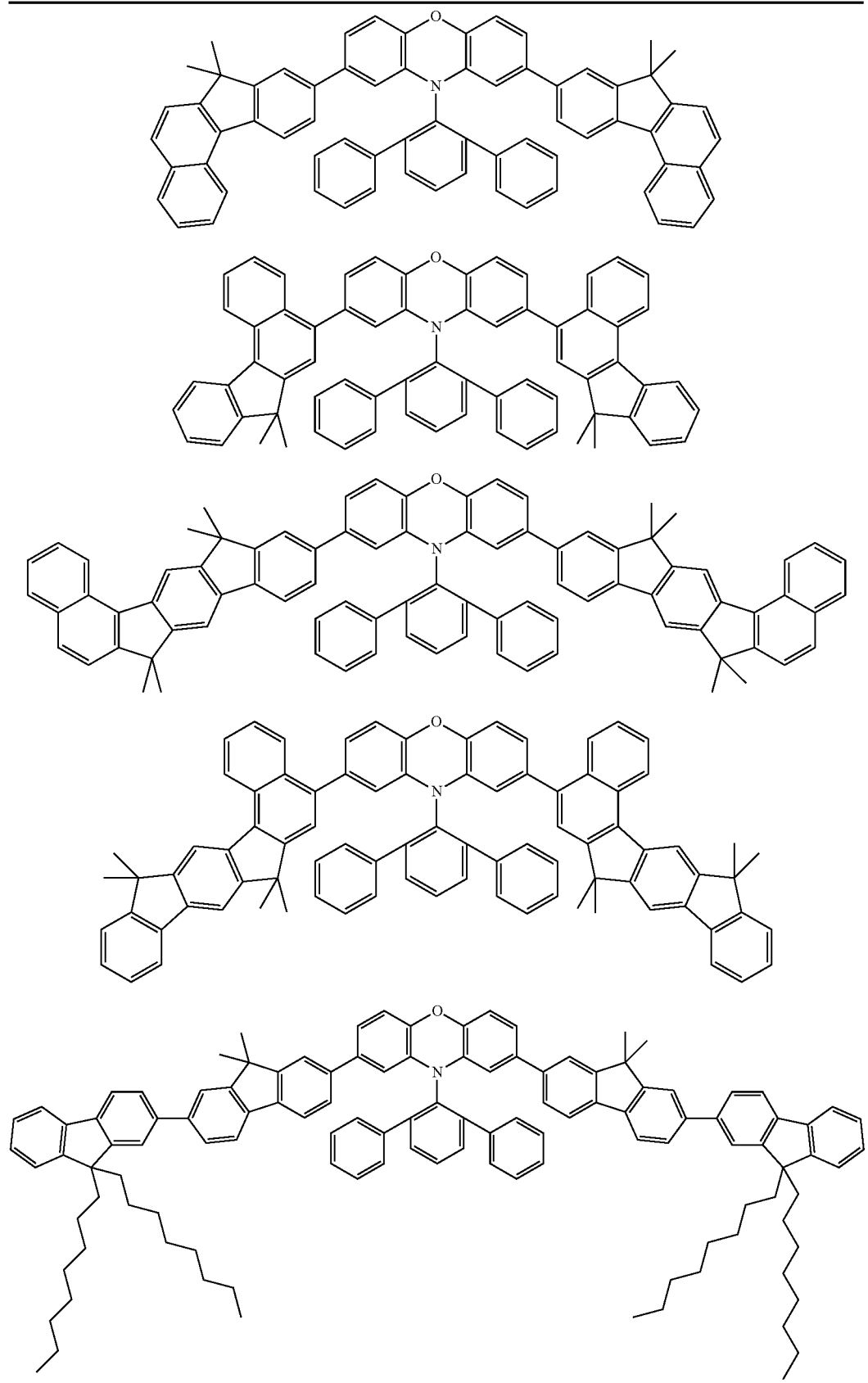

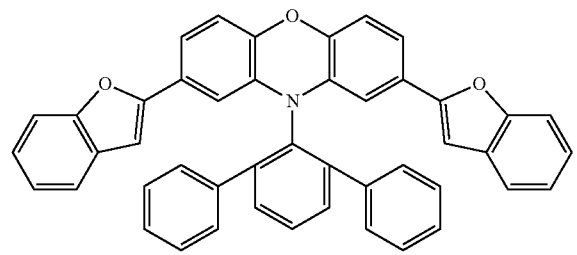 [SMILES: c1ccc(-c2cccc(-c3ccccc3)c2N2c3cc(-c4cc5ccccc5o4)ccc3Oc3ccc(-c4cc5ccccc5o4)cc32)cc1]
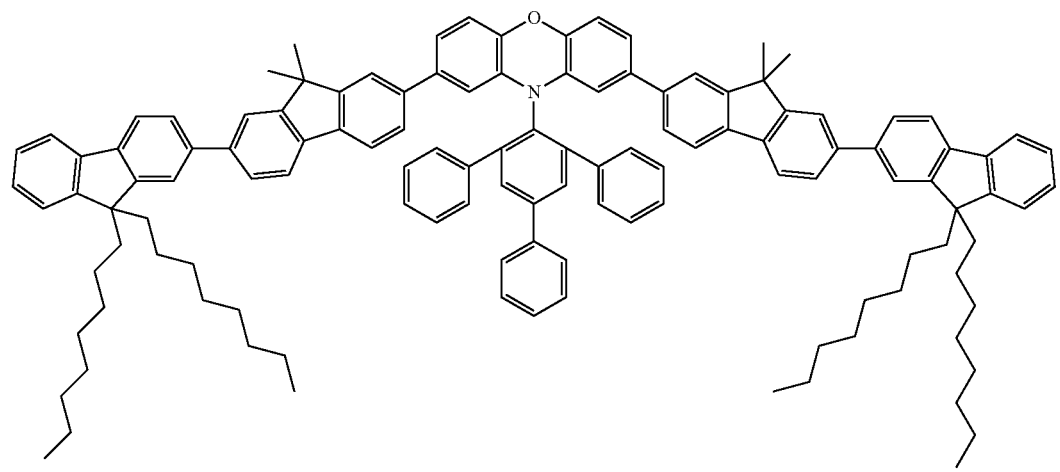 [SMILES: CCCCCCCCC1(CCCCCCCC)c2ccccc2-c2ccc(-c3ccc4c(c3)C(C)(C)c3cc(-c5ccc6c(c5)N(c5c(-c7ccccc7)cc(-c7ccccc7)cc5-c5ccccc5)c5cc(-c7ccc8c(c7)C(C)(C)c7cc(-c9ccc%10c(c9)C(CCCCCCCC)(CCCCCCCC)c9ccccc9-%10)ccc7-8)ccc5O6)ccc3-4)cc21]
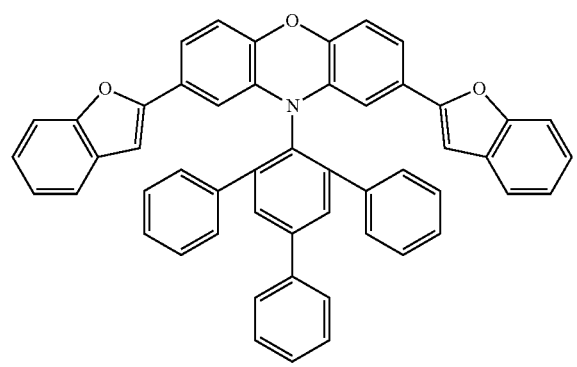 [SMILES: c1ccc(-c2cc(-c3ccccc3)c(N3c4cc(-c5cc6ccccc6o5)ccc4Oc4ccc(-c5cc6ccccc6o5)cc43)c(-c3ccccc3)c2)cc1]
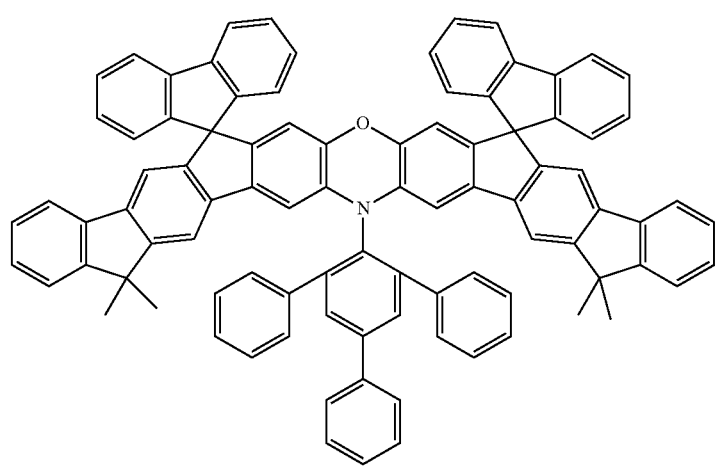 [SMILES: CC1(C)c2ccccc2-c2cc3c(cc21)-c1cc2c(cc1C31c3ccccc3-c3ccccc31)Oc1cc3c(cc1N2c1c(-c2ccccc2)cc(-c2ccccc2)cc1-c1ccccc1)-c1cc2c(cc1C31c3ccccc3-c3ccccc31)-c1ccccc1C2(C)C]

-continued
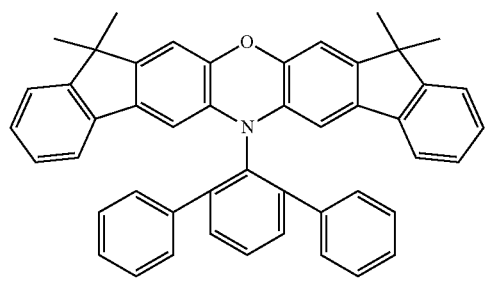 [SMILES: CC1(C)c2ccccc2-c2cc3c(cc21)Oc1cc2c(cc1N3c1c(-c3ccccc3)cccc1-c1ccccc1)-c1ccccc1C2(C)C]
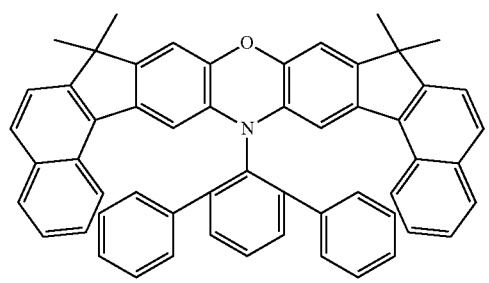 [SMILES: CC1(C)c2cc3c(cc2-c2c1ccc1ccccc21)N(c1c(-c2ccccc2)cccc1-c1ccccc1)c1cc2c(cc1O3)C(C)(C)c1ccc3ccccc3c1-2]
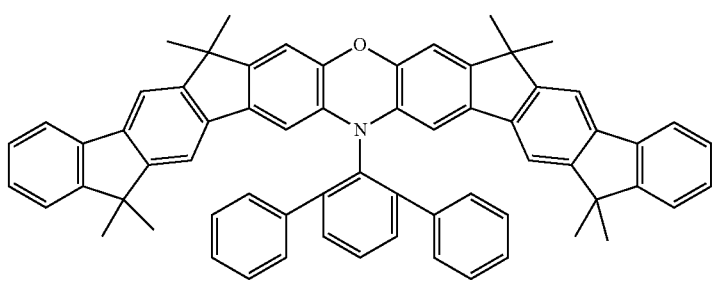 [SMILES: CC1(C)c2ccccc2-c2cc3c(cc21)-c1cc2c(cc1C3(C)C)Oc1cc3c(cc1N2c1c(-c2ccccc2)cccc1-c1ccccc1)-c1cc2c(cc1C3(C)C)-c1ccccc1C2(C)C]
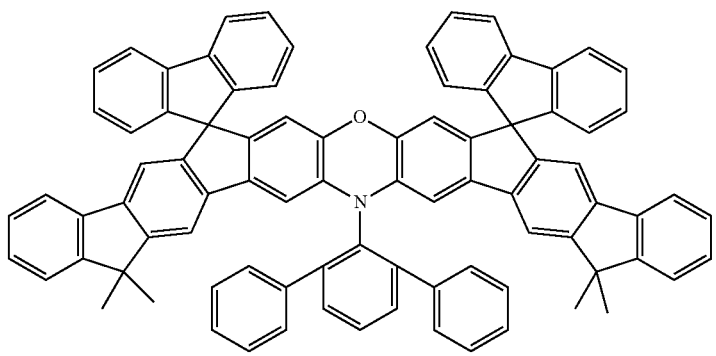 [SMILES: CC1(C)c2ccccc2-c2cc3c(cc21)-c1cc2c(cc1C31c3ccccc3-c3ccccc31)Oc1cc3c(cc1N2c1c(-c2ccccc2)cccc1-c1ccccc1)-c1cc2c(cc1C31c3ccccc3-c3ccccc31)-c1ccccc1C2(C)C]
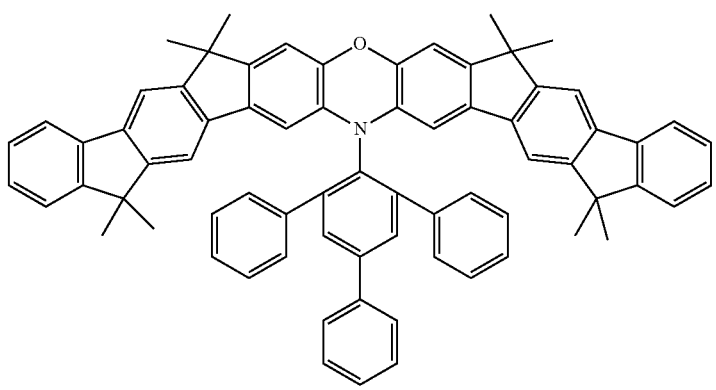 [SMILES: CC1(C)c2ccccc2-c2cc3c(cc21)-c1cc2c(cc1C3(C)C)Oc1cc3c(cc1N2c1c(-c2ccccc2)cc(-c2ccccc2)cc1-c1ccccc1)-c1cc2c(cc1C3(C)C)-c1ccccc1C2(C)C]

-continued
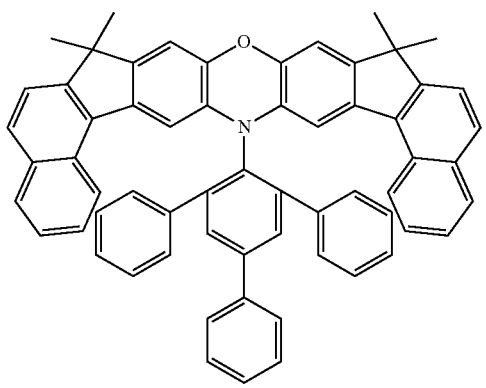 [SMILES: CC1(C)c2cc3c(cc2-c2c1ccc1ccccc21)N(c1c(-c2ccccc2)cc(-c2ccccc2)cc1-c1ccccc1)c1cc2c(cc1O3)C(C)(C)c1ccc3ccccc3c1-2]
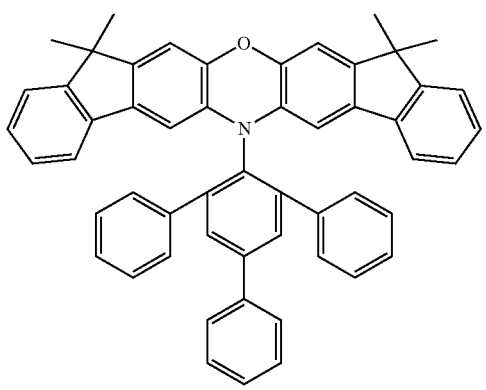 [SMILES: CC1(C)c2ccccc2-c2cc3c(cc21)Oc1cc2c(cc1N3c1c(-c3ccccc3)cc(-c3ccccc3)cc1-c1ccccc1)-c1ccccc1C2(C)C]
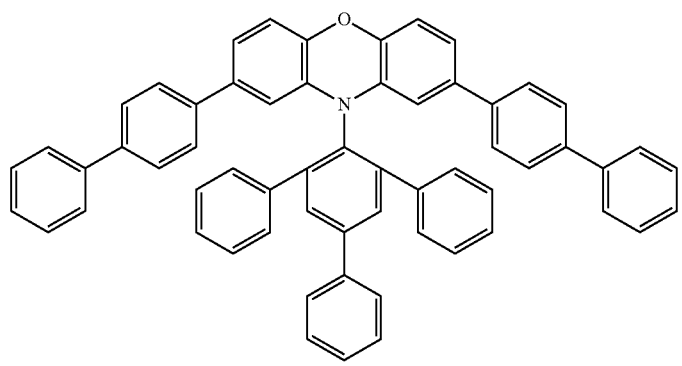 [SMILES: c1ccc(-c2ccc(-c3ccc4c(c3)N(c3c(-c5ccccc5)cc(-c5ccccc5)cc3-c3ccccc3)c3cc(-c5ccc(-c6ccccc6)cc5)ccc3O4)cc2)cc1]
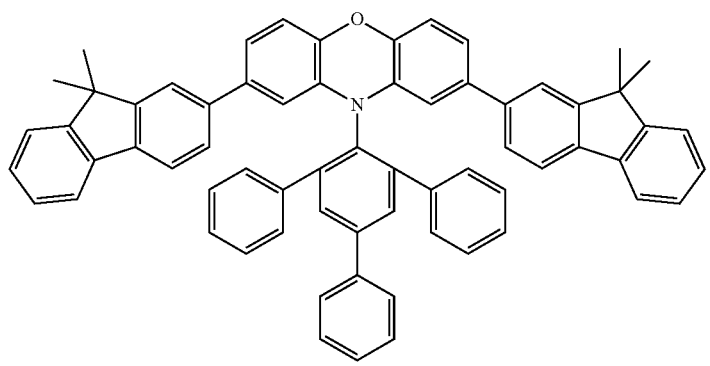 [SMILES: CC1(C)c2ccccc2-c2ccc(-c3ccc4c(c3)N(c3c(-c5ccccc5)cc(-c5ccccc5)cc3-c3ccccc3)c3cc(-c5ccc6c(c5)C(C)(C)c5ccccc5-6)ccc3O4)cc21]

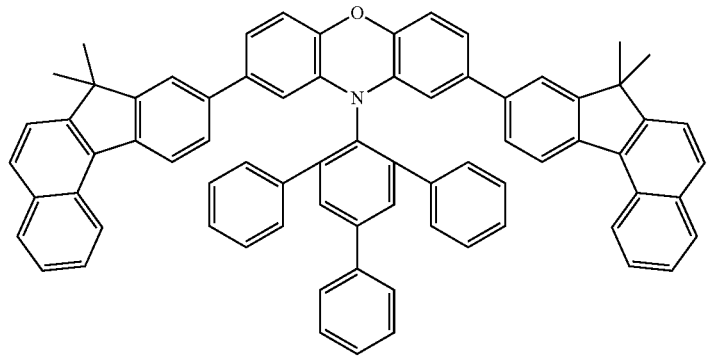 [SMILES: CC1(C)c2cc(-c3ccc4c(c3)N(c3c(-c5ccccc5)cc(-c5ccccc5)cc3-c3ccccc3)c3cc(-c5ccc6c(c5)C(C)(C)c5ccc7ccccc7c5-6)ccc3O4)ccc2-c2c1ccc1ccccc21]
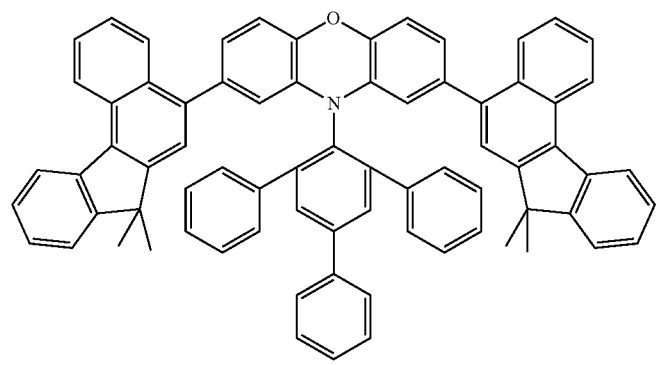 [SMILES: CC1(C)c2ccccc2-c2c1cc(-c1ccc3c(c1)N(c1c(-c4ccccc4)cc(-c4ccccc4)cc1-c1ccccc1)c1cc(-c4cc5c(c6ccccc46)-c4ccccc4C5(C)C)ccc1O3)c1ccccc21]
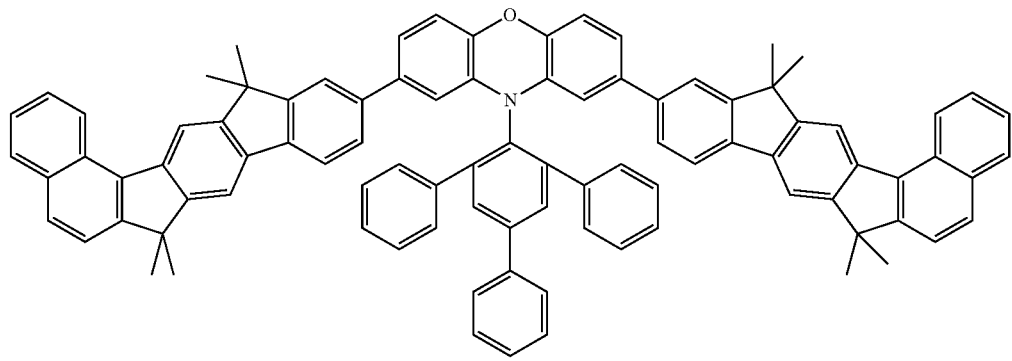 [SMILES: CC1(C)c2cc(-c3ccc4c(c3)N(c3c(-c5ccccc5)cc(-c5ccccc5)cc3-c3ccccc3)c3cc(-c5ccc6c(c5)C(C)(C)c5cc7c(cc5-6)C(C)(C)c5ccc6ccccc6c5-7)ccc3O4)ccc2-c2cc3c(cc21)-c1c(ccc2ccccc12)C3(C)C]
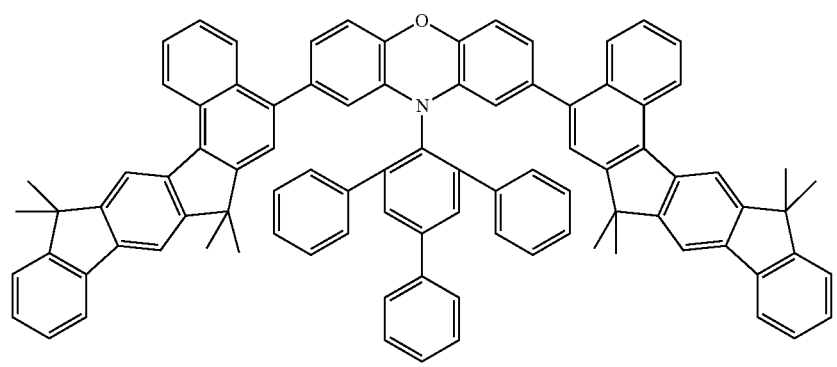 [SMILES: CC1(C)c2ccccc2-c2cc3c(cc21)-c1c(cc(-c2ccc4c(c2)N(c2c(-c5ccccc5)cc(-c5ccccc5)cc2-c2ccccc2)c2cc(-c5cc6c(c7ccccc57)-c5cc7c(cc5C6(C)C)-c5ccccc5C7(C)C)ccc2O4)c2ccccc12)C3(C)C]

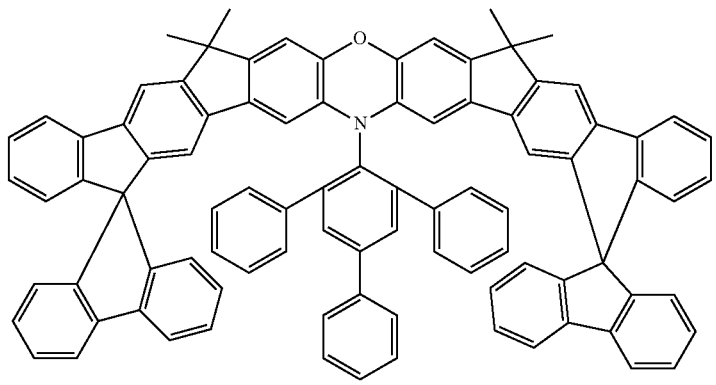 [SMILES: CC1(C)c2cc3c(cc2-c2cc4c(cc21)-c1ccccc1C41c2ccccc2-c2ccccc21)N(c1c(-c2ccccc2)cc(-c2ccccc2)cc1-c1ccccc1)c1cc2c(cc1O3)C(C)(C)c1cc3c(cc1-2)C1(c2ccccc2-c2ccccc21)c1ccccc1-3]

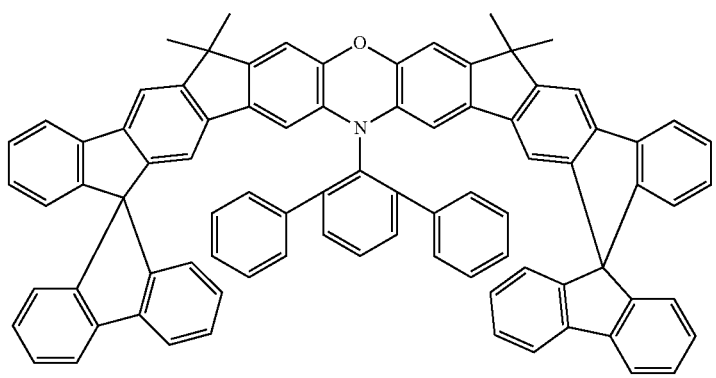 [SMILES: CC1(C)c2cc3c(cc2-c2cc4c(cc21)-c1ccccc1C41c2ccccc2-c2ccccc21)N(c1c(-c2ccccc2)cccc1-c1ccccc1)c1cc2c(cc1O3)C(C)(C)c1cc3c(cc1-2)C1(c2ccccc2-c2ccccc21)c1ccccc1-3]

The synthesis of the compounds according to the invention can be carried out by processes of preparative organic chemistry which are generally known to the person skilled in the art. Examples of reactions which are preferably employed are halogenations and transition metal-catalysed coupling reactions, preferably Suzuki couplings and Buchwald couplings.

Illustrative processes for the preparation of the compounds according to the invention are presented below. The processes shown are particularly suitable for the preparation of the compounds according to the invention. However, alternative processes are conceivable and possibly preferable in certain cases. Accordingly, the person skilled in the art will be able to modify the processes shown below within the scope of his general expert knowledge.

The compounds according to the invention are preferably synthesised as shown in Scheme 1 and Scheme 2 or as shown in Scheme 1 and Scheme 3. All compounds shown may optionally be substituted by one or more organic radicals.

Scheme 1

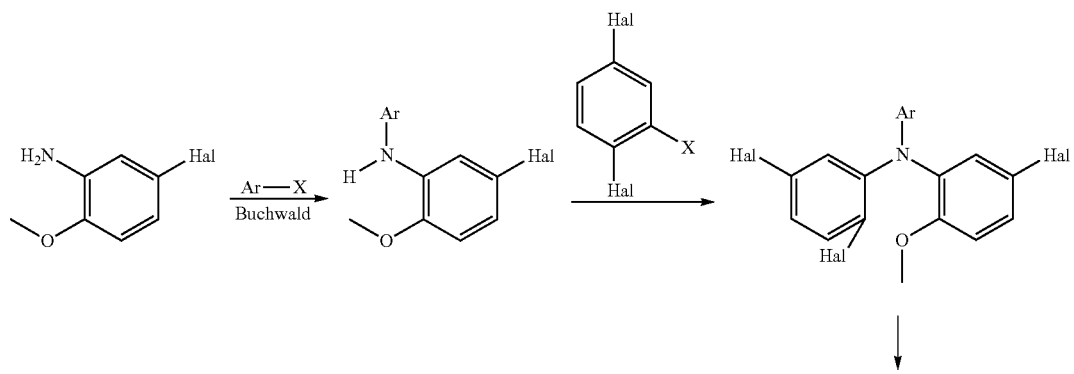

-continued

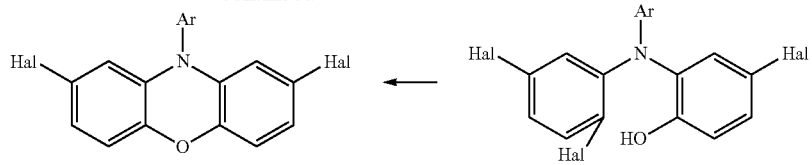

R = organic radical
Ar = Aryl or heteroaryl
Hal = Halogen or another reactive leaving group
X = Any halogen or reactive leaving group, which is more reactive than Hal The compounds in accordance with Scheme 1 may already contain two halogen groups or other reactive leaving groups.

The compounds are reacted with an aryl or heteroaryl compound Ar'—X in a Suzuki coupling, which introduces the substituent on the phenoxazine backbone para to the O atom (Scheme 2).

Alternatively, the compounds are reacted with a diarylamine compound HN(Ar')$_2$ in a Buchwald coupling, which introduces the substituent on the phenoxazine backbone para to the O atom (Scheme 3).

Scheme 2

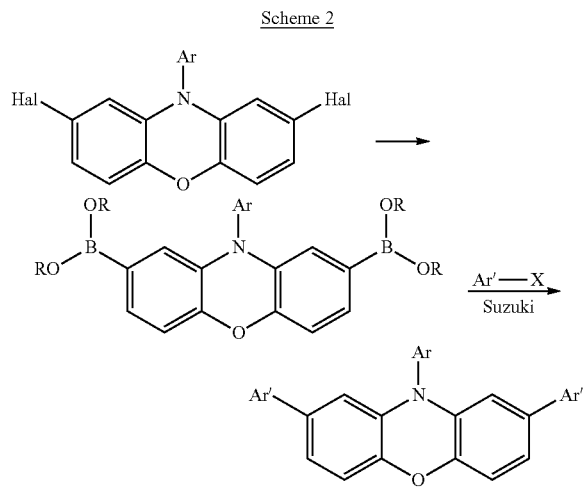

R = organic radical
Ar, Ar' = Aryl or heteroaryl
Hal = Halogen or another reactive leaving group
X = Halogen or another reactive leaving group Scheme 3

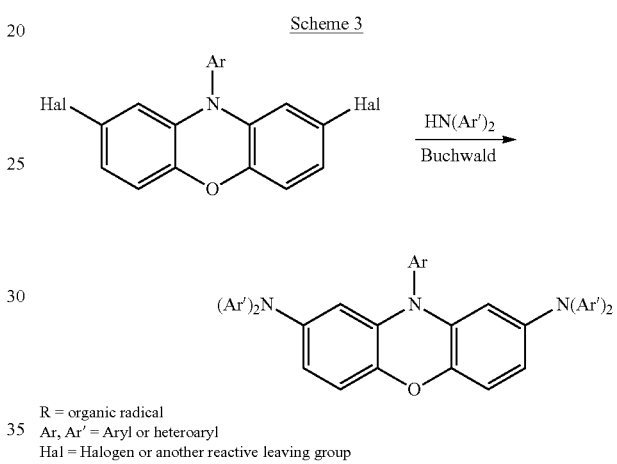

R = organic radical
Ar, Ar' = Aryl or heteroaryl
Hal = Halogen or another reactive leaving group Alternatively, the compounds are reacted with an aryl or heteroaryl compound comprising a carboxylate ester group ROOC—Ar'—X'— in a Suzuki coupling, which introduces the substituent on the phenoxazine backbone para to the O atom (Scheme 4). The carboxylate substituents are then alkylated via a reaction using an organometallic and the compound is finally condensed.

Scheme 4

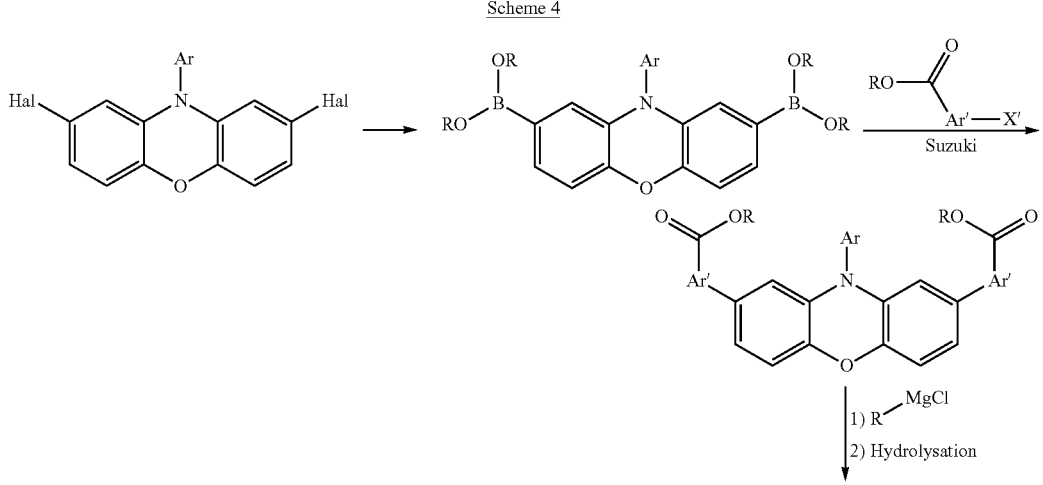

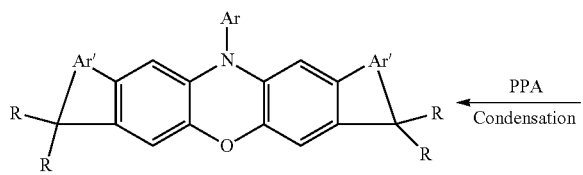 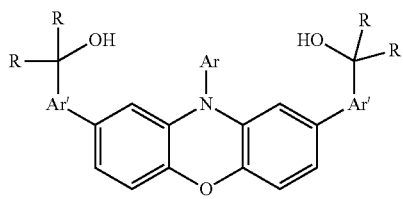

PPA Condensation

R = organic radical
Ar, Ar' = Aryl or heteroaryl
Hal = Halogen or another reactive leaving group
X = Halogen or another reactive leaving group The synthetic process shown above has an illustrative character and may be modified in a suitable manner by the person skilled in the art in the area of organic synthesis if this is advantageous for the synthesis of certain embodiments of compounds according to the invention.

The present invention thus furthermore relates to a process for the preparation of compounds of the formula (1) which is characterised in that one or more transition metal-catalysed coupling reactions by means of which aryl, heteroaryl or diarylamino groups are introduced as substituents para to the O atom from a phenoxazine derivative. The transition metal-catalysed coupling reactions are preferably selected from Hartwig-Buchwald couplings and Suzuki couplings.

The compounds according to the invention described above, in particular compounds which are substituted by reactive leaving groups, such as bromine, iodine, chlorine, boronic acid or boronic acid ester, can be used as monomers for the production of corresponding oligomers, dendrimers or polymers. Suitable reactive leaving groups are, for example, bromine, iodine, chlorine, boronic acids, boronic acid esters, amines, alkenyl or alkynyl groups having a terminal C=C double bond or C—C triple bond, oxiranes, oxetanes, groups which undergo a cycloaddition, for example a 1,3-dipolar cycloaddition, such as, for example, dienes or azides, carboxylic acid derivatives, alcohols and silanes.

The invention therefore furthermore relates to oligomers, polymers or dendrimers containing one or more compounds of the formula (1), where the bond(s) to the polymer, oligomer or dendrimer may be localised at any desired positions in formula (1) which are substituted by $R^1$, $R^2$ or $R^3$. Depending on the linking of the compound of the formula (1), the compound is a constituent of a side chain of the oligomer or polymer or a constituent of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (1) may be linked directly to one another or they may be linked to one another via a divalent group, for example via a substituted or unsubstituted alkylene group, via a heteroatom or via a divalent aromatic or heteroaromatic group. In branched and dendritic structures, for example, three or more units of the formula (1) may be linked via a trivalent or polyvalent group, for example via a trivalent or polyvalent aromatic or heteroaromatic group, to form a branched or dendritic oligomer or polymer.

The same preferences as described above for compounds of the formula (1) apply to the recurring units of the formula (1) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 2000/22026), spirobifluorenes (for example in accordance with EP 707020, EP 894107 or WO 2006/061181), para-phenylenes (for example in accordance with WO 1992/18552), carbazoles (for example in accordance with WO 2004/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with 3 WO 2007/068325) or phosphorescent metal complexes (for example in accordance with WO 2006/003000), and/or charge-transport units, in particular those based on triarylamines.

The polymers and oligomers according to the invention are generally prepared by polymerisation of one or more types of monomer, at least one monomer of which results in recurring units of the formula (1) in the polymer. Suitable polymerisation reactions are known to the person skilled in the art and are described in the literature. Particularly suitable and preferred polymerisation reactions which result in C—C or C—N links are the following:
  (A) SUZUKI polymerisation;
  (B) YAMAMOTO polymerisation;
  (C) STILLE polymerisation; and
  (D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

The present invention thus also relates to a process for the preparation of the polymers, oligomers and dendrimers according to the invention, which is characterised in that they are prepared by SUZUKI polymerisation, YAMAMOTO polymerisation, STILLE polymerisation or HARTWIG-BUCHWALD polymerisation. The dendrimers according to the invention can be prepared by processes known to the person skilled in the art or analogously thereto.

Suitable processes are described in the literature, such as, for example, in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 2002/067343 A1 and WO 2005/026144 A1.

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methylTHF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetol, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore furthermore relates to a formulation, in particular a solution, dispersion or emulsion, comprising at least one compound of the formula (1) or at least one polymer, oligomer or dendrimer containing at least one unit of the formula (1), and at least one solvent, preferably an organic solvent. The way in which solutions of this type can be prepared is known to the person skilled in the art and is described, for example, in WO 2002/072714, WO 2003/019694 and the literature cited therein.

The compounds of the formula (1) according to the invention are suitable for use in electronic devices, in particular in organic electroluminescent devices (OLEDs). Depending on the substitution, the compounds are employed in different functions and layers.

The invention therefore furthermore relates to the use of a compound of the formula (1) in an electronic device. The electronic device here is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and particularly preferably organic electroluminescent devices (OLEDs).

The invention furthermore relates to an electronic device comprising at least one compound of the formula (1). The electronic device is preferably selected from the devices indicated above. Particular preference is given to an organic electroluminescent device comprising anode, cathode and at least one emitting layer, characterised in that at least one organic layer comprises at least one compound of the formula (1).

Apart from cathode, anode and emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, interlayers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions. However, it should be pointed out that each of these layers does not necessarily have to be present and the choice of layers is always dependent on the compounds used and in particular also on whether the electroluminescent device is fluorescent or phosphorescent.

The sequence of the layers of the organic electroluminescent device is preferably the following:

anode-hole-injection layer-hole-transport layer-emitting layer-electron-transport layer-electron-injection layer-cathode.

It should again be pointed out here that not all the said layers have to be present, and/or that further layers may additionally be present.

The organic electroluminescent device according to the invention may comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers. Particular preference is given to three-layer systems, i.e. systems having three emitting layers, where at least one of these layers preferably comprises at least one compound of the formula (1) and where the three layers exhibit blue, green and orange or red emission (for the basic structure see, for example, WO 2005/011013). It should be noted that, for the generation of white light, an emitter compound used individually which emits in a broad wavelength range may also be suitable instead of a plurality of emitter compounds emitting in colour.

The compounds according to the invention may alternatively and/or additionally also be present in the hole-transport layer or in another layer.

It is preferred for the compound of the formula (1) to be employed in an emitting layer. In particular, the compound of the formula (1) is suitable for use as emitting material (emitter compound).

The compound according to the invention is particularly suitable for use as blue-emitting emitter compound. The electronic device concerned may comprise a single emitting layer comprising the compound according to the invention or it may comprise two or more emitting layers. The further emitting layers here may comprise one or more compounds according to the invention or alternatively other compounds.

If the compound according to the invention is employed as emitting material in an emitting layer, it is preferably employed in combination with one or more matrix materials.

The proportion of the compound according to the invention in the mixture of the emitting layer is in this case preferably between 0.1 and 50.0% by vol., particularly preferably between 0.5 and 20.0% by vol., very particularly preferably between 1.0 and 10.0% by vol. Correspondingly, the proportion of the matrix material or matrix materials is between 50.0 and 99.9% by vol., particularly preferably between 80.0 and 99.5% by vol., very particularly preferably between 90.0 and 99.0% by vol.

Preferred matrix materials for use in combination with the materials according to the invention as emitters are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Preferred matrix materials for use in combination with the compound of the formula (1) in the emitting layer are depicted in the following table.

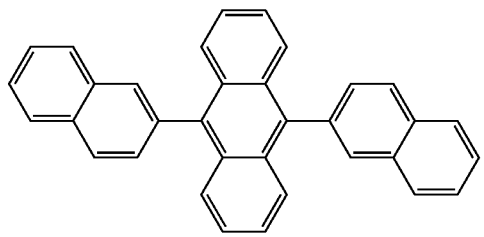 [SMILES: c1ccc2cc(-c3c4ccccc4c(-c4ccc5ccccc5c4)c4ccccc34)ccc2c1]

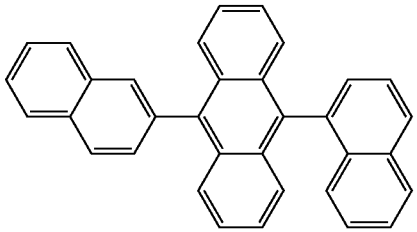 [SMILES: c1ccc2cc(-c3c4ccccc4c(-c4cccc5ccccc45)c4ccccc34)ccc2c1]

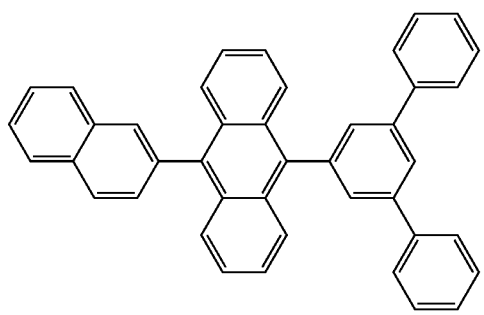 [SMILES: c1ccc(-c2cc(-c3ccccc3)cc(-c3c4ccccc4c(-c4ccc5ccccc5c4)c4ccccc34)c2)cc1]

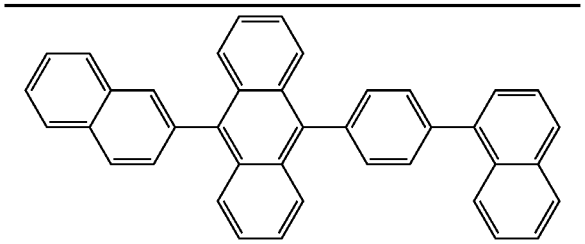

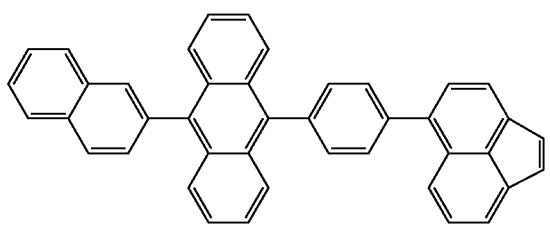

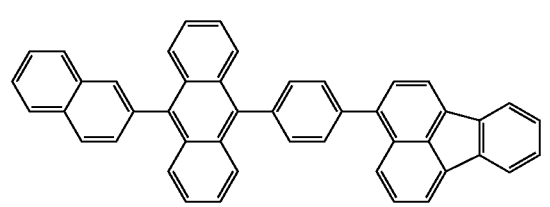

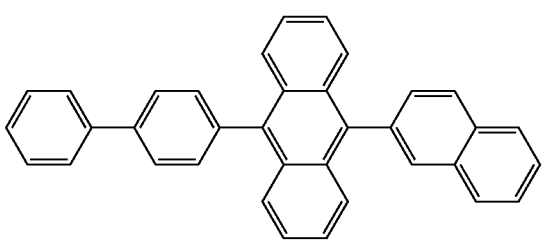 [SMILES: c1ccc(-c2ccc(-c3c4ccccc4c(-c4ccc5ccccc5c4)c4ccccc34)cc2)cc1]

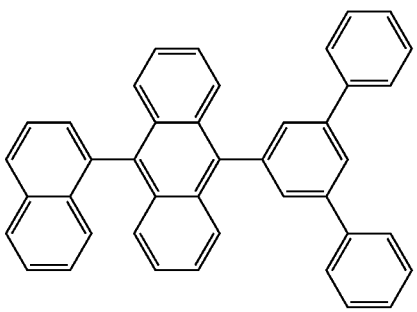 [SMILES: c1ccc(-c2cc(-c3ccccc3)cc(-c3c4ccccc4c(-c4cccc5ccccc45)c4ccccc34)c2)cc1]

97
-continued
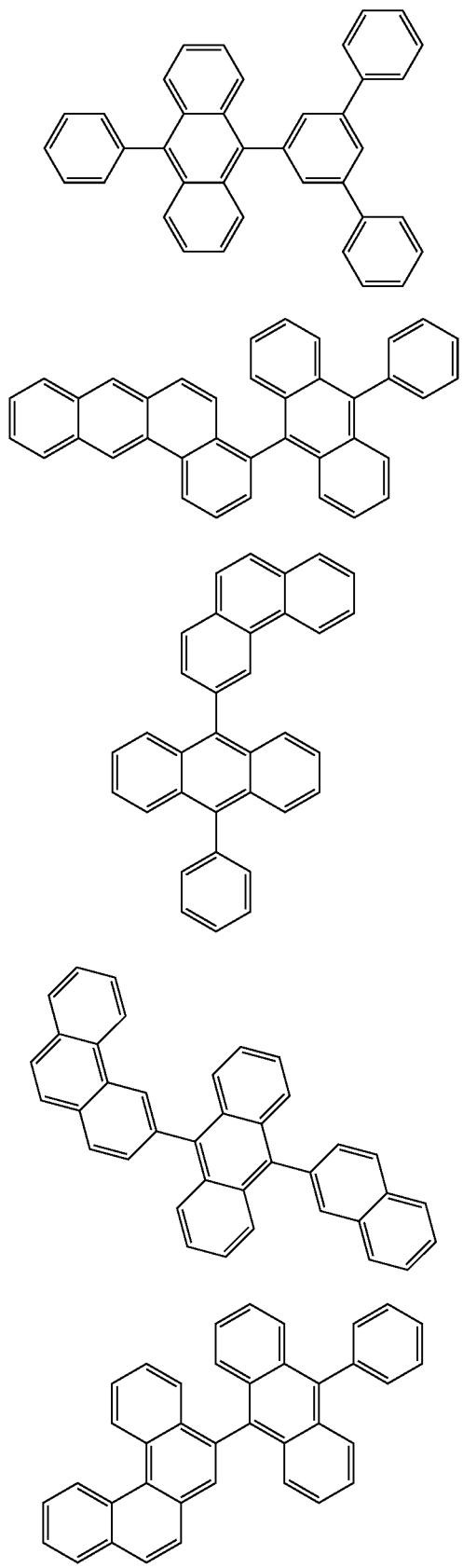
98
-continued
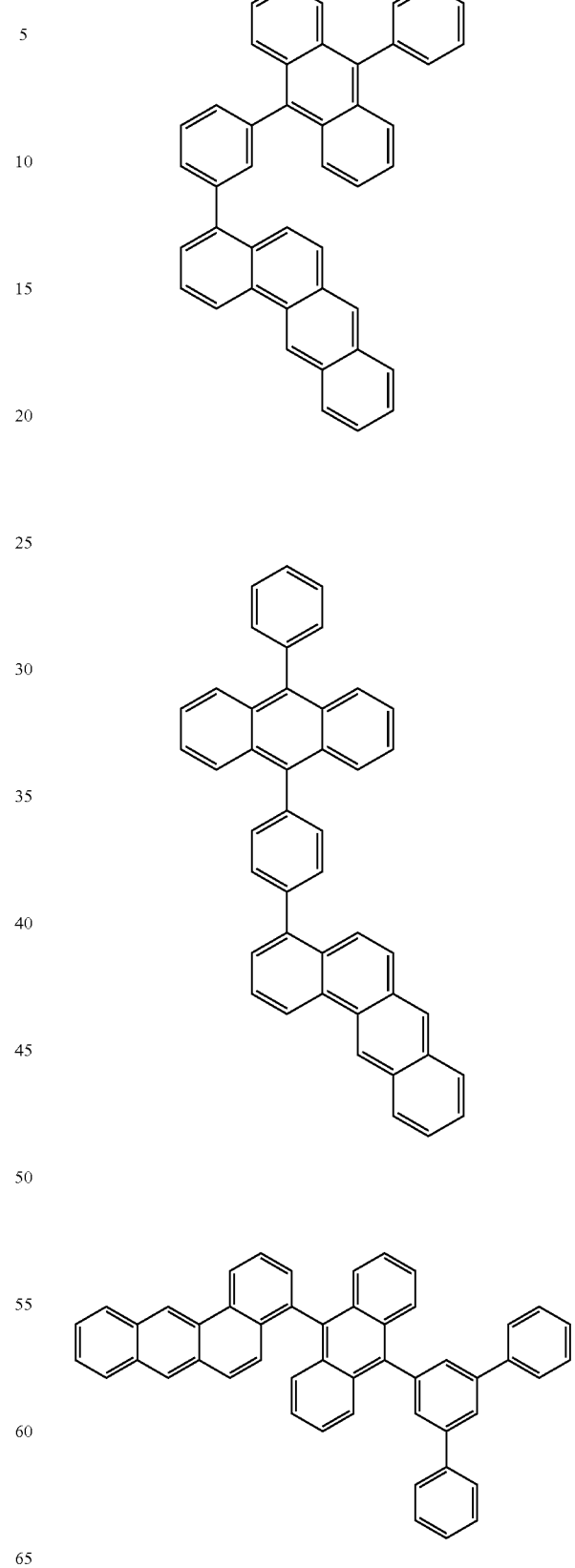

99
-continued
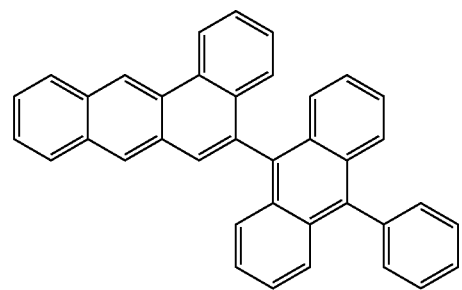 [SMILES: c1ccc(-c2c3ccccc3c(-c3cc4cc5ccccc5cc4c4ccccc34)c3ccccc23)cc1]
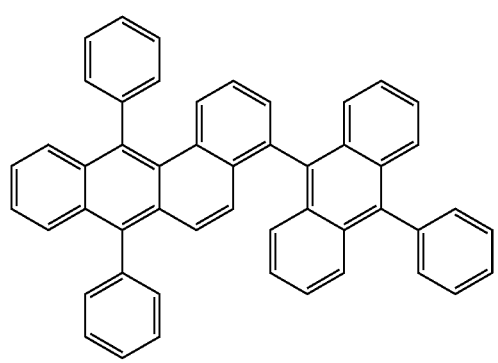 [SMILES: c1ccc(-c2c3ccccc3c(-c3cccc4c3ccc3c(-c5ccccc5)c5ccccc5c(-c5ccccc5)c34)c3ccccc23)cc1]
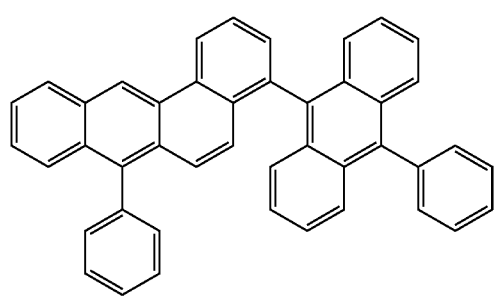 [SMILES: c1ccc(-c2c3ccccc3c(-c3cccc4c3ccc3c(-c5ccccc5)c5ccccc5cc34)c3ccccc23)cc1]
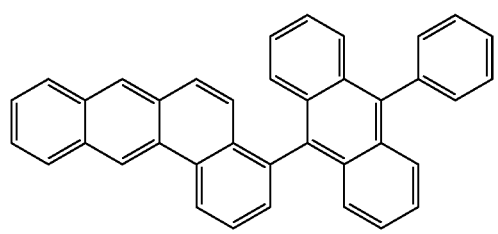 [SMILES: c1ccc(-c2c3ccccc3c(-c3cccc4c3ccc3cc5ccccc5cc34)c3ccccc23)cc1]
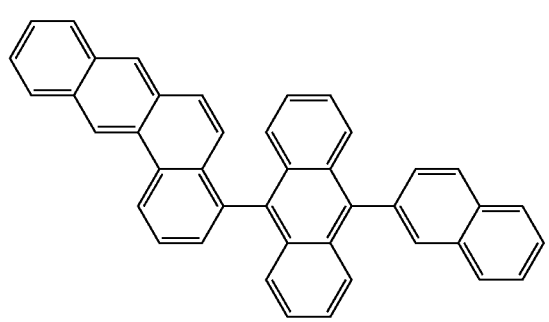 [SMILES: c1ccc2cc(-c3c4ccccc4c(-c4cccc5c4ccc4cc6ccccc6cc45)c4ccccc34)ccc2c1]
100
-continued
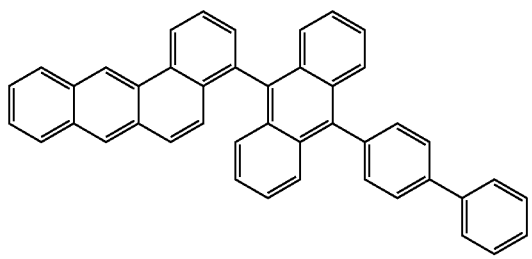 [SMILES: c1ccc(-c2ccc(-c3c4ccccc4c(-c4cccc5c4ccc4cc6ccccc6cc45)c4ccccc34)cc2)cc1]
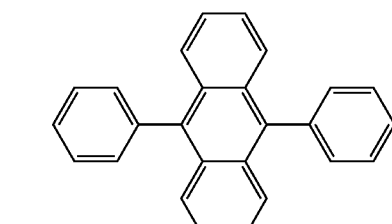
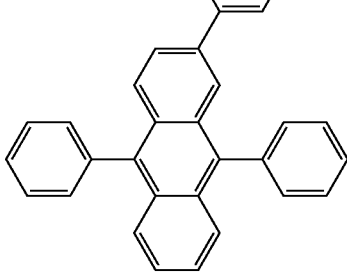
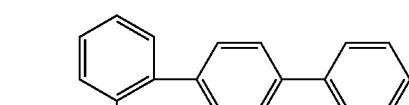
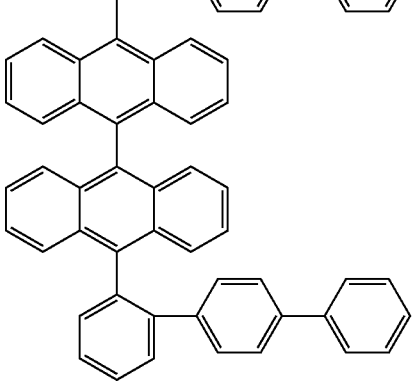
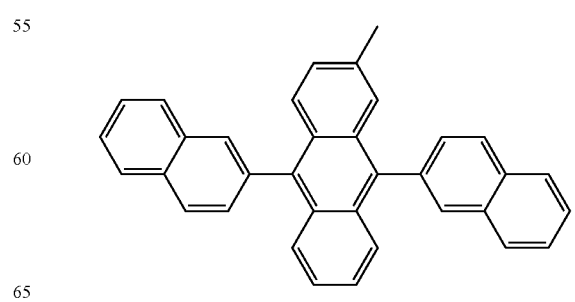

101
-continued
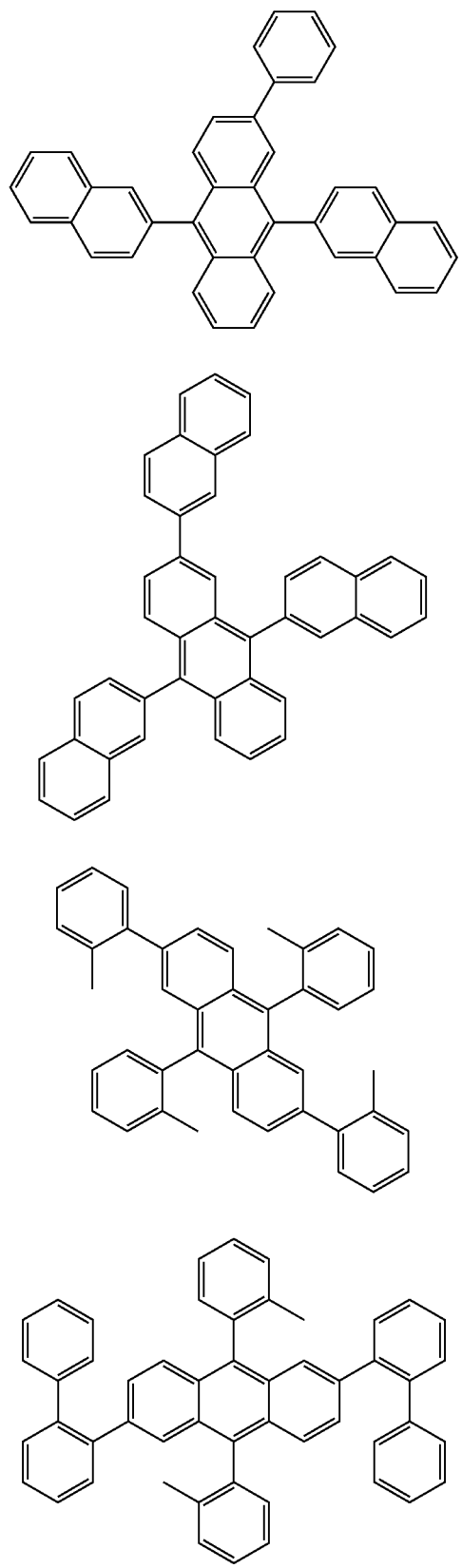
102
-continued
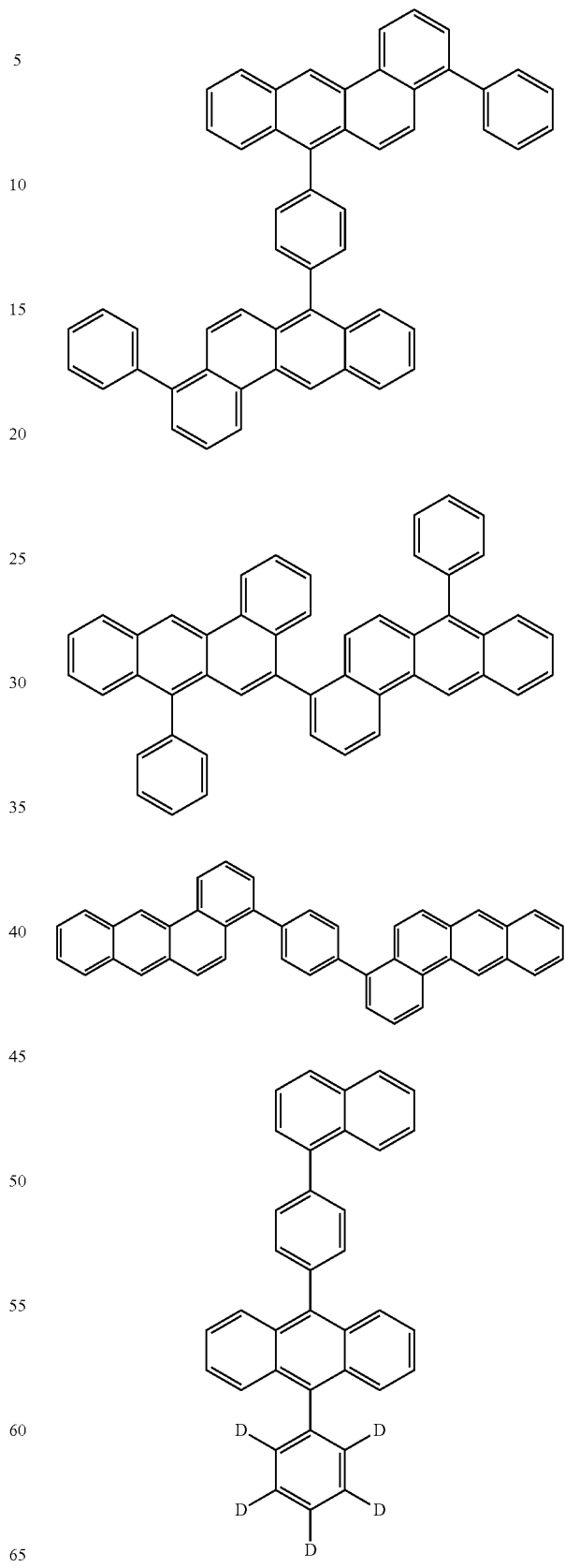

103
-continued
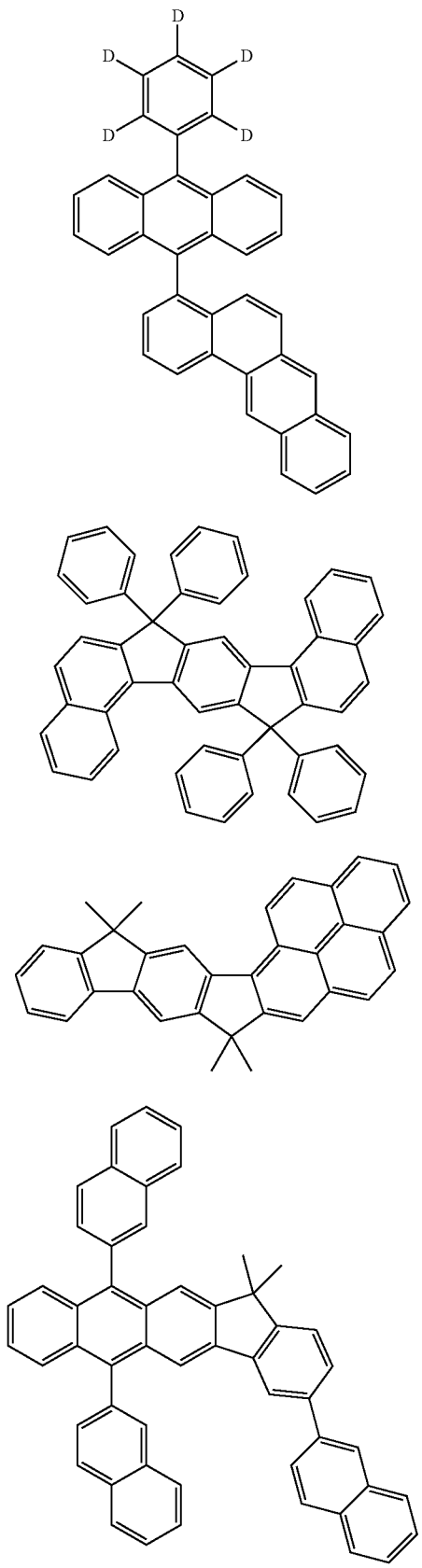
104
-continued
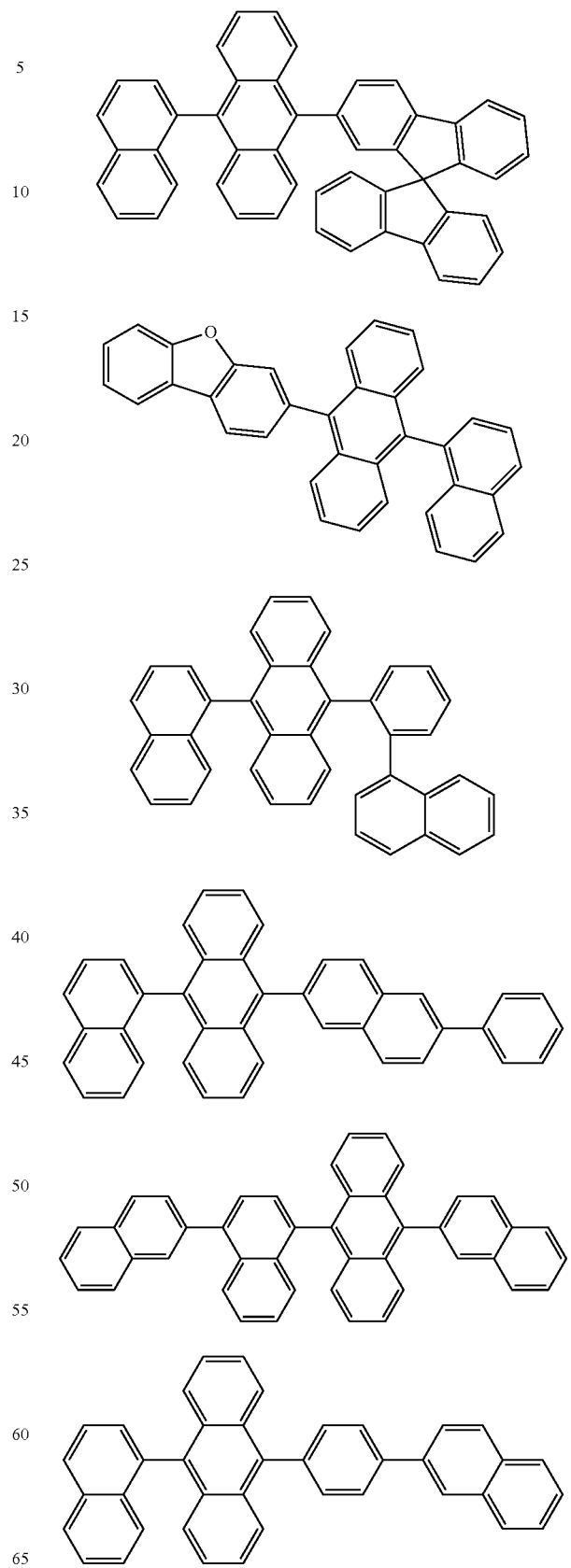

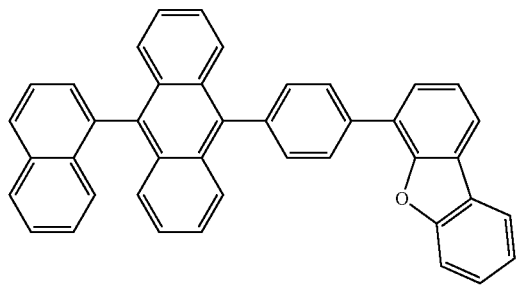 [SMILES: c1ccc2c(-c3c4ccccc4c(-c4ccc(-c5cccc6c5oc5ccccc56)cc4)c4ccccc34)cccc2c1]

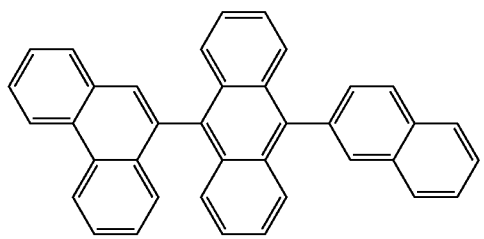 [SMILES: c1ccc2cc(-c3c4ccccc4c(-c4cc5ccccc5c5ccccc45)c4ccccc34)ccc2c1]

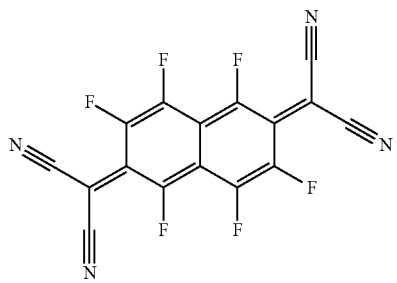
(D-1)

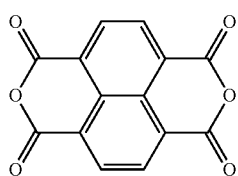
(D-2)

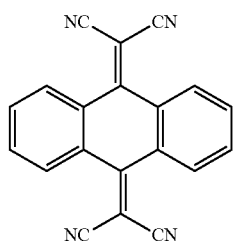
(D-3)

The compounds according to the invention can also be employed in other layers, for example as hole-transport materials in a hole-injection or hole-transport layer or electron-blocking layer or as matrix materials in an emitting layer, preferably as matrix materials for fluorescent emitters.

If the compound of the formula (1) is employed as hole-transport material in a hole-transport layer, a hole-injection layer or an electron-blocking layer, the compound can be employed as pure material, i.e. in a proportion of 100%, in the hole-transport layer, or it can be employed in combination with one or more further compounds. According to a preferred embodiment, the organic layer comprising the compound of the formula (1) then additionally comprises one or more p-dopants. The p-dopants employed in accordance with the present invention are preferably organic electron-acceptor compounds which are able to oxidise one or more of the other compounds of the mixture.

Particularly preferred embodiments of p-dopants are the compounds disclosed in WO 2011/073149, EP 1968131, EP 2276085, EP 2213662, EP 1722602, EP 2045848, DE 102007031220, U.S. Pat. Nos. 8,044,390, 8,057,712, WO 2009/003455, WO 2010/094378, WO 2011/120709, US 2010/0096600 and WO 2012/095143.

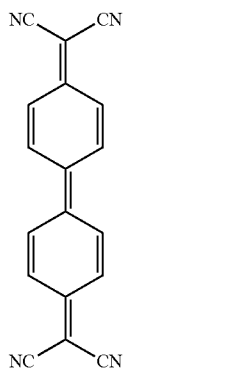
(D-4)

Particularly preferred as p-dopants are quinodimethane compounds, azaindenofluorendione, azaphenalene, azatriphenylene, $I_2$, metal halides, preferably transition metal halides, metal oxides, preferably metal oxides containing at least one transition metal or a metal of the 3rd main group and transition metal complexes, preferably complexes of Cu, Co, Ni, Pd and Pt with ligands containing at least one oxygen atom as binding site. Also preferred are transition metal oxides as dopants, preferably oxides of rhenium, molybdenum and tungsten, particularly preferably $Re_2O_7$, $MoO_3$, $WO_3$ and $ReO_3$.

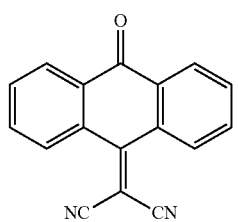
(D-5)

The p-dopants are preferably distributed substantially uniformly in the p-doped layers. This can be achieved for example by co-evaporation of the p-dopant and of the hole-transport material matrix.

Particularly preferred p-dopants are selected from the compounds (D-1) to (D-13):

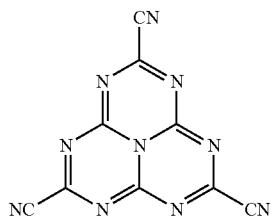
(D-6)

-continued (D-7) 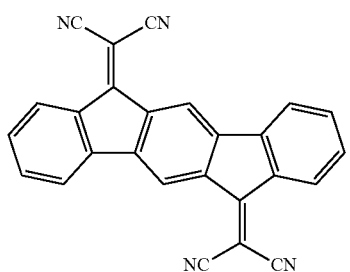

(D-8) 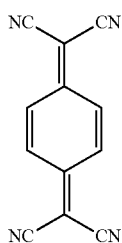

(D-9) 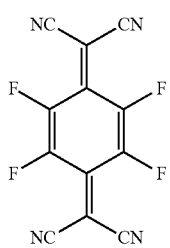

(D-10) 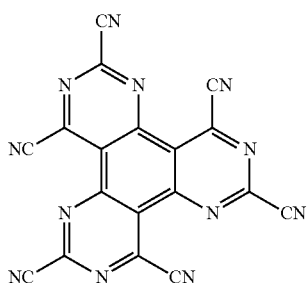

(D-11) 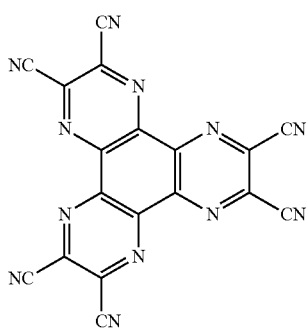

-continued (D-12) 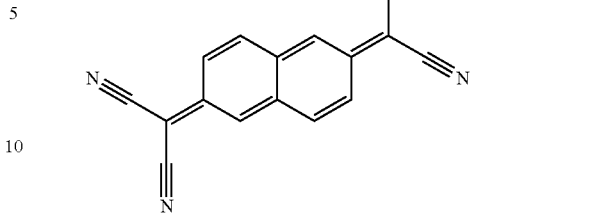

(D-13) 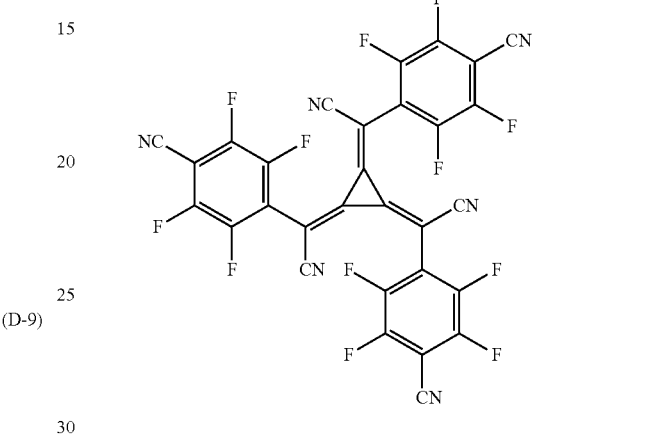

In an embodiment of the invention, the compound of the formula (1) or the preferred embodiments is used in a hole-transport or -injection layer in combination with a layer which comprises a hexaazatriphenylene derivative, in particular hexacyanohexaazatriphenylene (for example in accordance with EP 1175470). Thus, for example, preference is given to a combination which looks as follows: anode—hexaazatriphenylene derivative—hole-transport layer, where the hole-transport layer comprises one or more compounds of the formula (1) or the preferred embodiments. It is likewise possible in this structure to use a plurality of successive hole-transport layers, where at least one hole-transport layer comprises at least one compound of the formula (1) or the preferred embodiments. A further preferred combination looks as follows: anode—hole-transport layer—hexaazatriphenylene derivative—hole-transport layer, where at least one of the two hole-transport layers comprises one or more compounds of the formula (1) or the preferred embodiments. It is likewise possible in this structure to use a plurality of successive hole-transport layers instead of one hole-transport layer, where at least one hole-transport layer comprises at least one compound of the formula (1) or the preferred embodiments.

If the compound of the formula (1) is employed as matrix material in combination with a phosphorescent emitter in an emitting layer, the phosphorescent emitter is preferably selected from the classes and embodiments of phosphorescent emitters indicated below. Furthermore, one or more further matrix materials are preferably present in the emitting layer in this case.

So-called mixed-matrix systems of this type preferably comprise two or three different matrix materials, particularly preferably two different matrix materials. It is preferred here for one of the two materials to be a material having hole-transporting properties and for the other material to be a material having electron-transporting properties. The compound of the formula (1) is preferably the material having hole-transporting properties.

However, the desired electron-transporting and hole-transporting properties of the mixed-matrix components may also be combined mainly or completely in a single mixed-matrix component, where the further mixed-matrix component or components satisfy other functions. The two different matrix materials may be present here in a ratio of 1:50 to 1:1, preferably 1:20 to 1:1, particularly preferably 1:10 to 1:1 and very particularly preferably 1:4 to 1:1. Mixed-matrix systems are preferably employed in phosphorescent organic electroluminescent devices. Further details on mixed-matrix systems are contained, inter alia, in the application WO 2010/108579.

Particularly suitable matrix materials which can be used as matrix components of a mixed-matrix system in combination with the compounds according to the invention are selected from the preferred matrix materials for phosphorescent emitters indicated below or the preferred matrix materials for fluorescent emitters, depending on what type of emitter compound is employed in the mixed-matrix system.

Generally preferred classes of material for use as corresponding functional materials in the organic electroluminescent devices according to the invention are indicated below.

Suitable phosphorescent emitters are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present invention, all luminescent iridium, platinum or copper complexes are regarded as phosphorescent compounds.

Examples of the phosphorescent emitters described above are revealed by the applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used in accordance with the prior art for phosphorescent OLEDs and as are known to the person skilled in the art in the area of organic electroluminescent devices are suitable for use in the devices according to the invention. The person skilled in the art will also be able to employ further phosphorescent complexes without inventive step in combination with the compounds according to the invention in OLEDs.

Preferred fluorescent emitters, besides the compounds according to the invention, are selected from the class of the arylamines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position.

Preferred matrix materials for use with fluorescent emitters compounds are indicated above.

Preferred matrix materials for phosphorescent emitters are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109, WO 2011/000455 or WO 2013/041176, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with US 2009/0136779, WO 2010/050778, WO 2011/042107, WO 2011/088877 or WO 2012/143080, triphenylene derivatives, for example in accordance with WO 2012/048781, or lactams, for example in accordance with WO 2011/116865 or WO 2011/137951.

Besides the compounds according to the invention, suitable charge-transport materials, as can be used in the hole-injection or hole-transport layer or electron-blocking layer or in the electron-transport layer of the electronic device according to the invention, are, for example, the compounds disclosed in Y. Shirota et al., Chem. Rev. 2007, 107(4), 953-1010, or other materials as are employed in these layers in accordance with the prior art.

Materials which can be used for the electron-transport layer are all materials as are used in accordance with the prior art as electron-transport materials in the electron-transport layer. Particularly suitable are aluminium complexes, for example $Alq_3$, zirconium complexes, for example $Zrq_4$, lithium complexes, for example Liq, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Furthermore suitable materials are derivatives of the above-mentioned compounds, as disclosed in JP 2000/053957, WO 2003/060956, WO 2004/028217, WO 2004/080975 and WO 2010/072300.

Preferred hole-transport materials which can be used in a hole-transport, hole-injection or electron-blocking layer in the electroluminescent device according to the invention are indenofluorenamine derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic rings (for example in accordance with U.S. Pat. No. 5,061,569), the amine derivatives disclosed in WO 95/09147, monobenzoindenofluorenamines (for example in accordance with WO 08/006449), dibenzoindenofluorenamines (for example in accordance with WO 07/140847), spirobifluorenamines (for example in accordance with WO 2012/034627 or WO 2013/120577), fluorenamines (for example in accordance with the as yet unpublished applications EP 12005369.9, EP 12005370.7 and EP 12005371.5), spirodibenzopyranamines (for example in accordance with WO 2013/083216) and dihydroacridine derivatives (for example in accordance with WO 2012/150001). The compounds according to the invention can also be used as hole-transport materials.

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ag/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function.

The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive doped polymers.

The device is appropriately (depending on the application) structured, provided with contacts and finally sealed, since the lifetime of the devices according to the invention is shortened in the presence of water and/or air.

In a preferred embodiment, the organic electroluminescent device according to the invention is characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (1) are necessary for this purpose. High solubility can be achieved through suitable substitution of the compounds.

For the production of an organic electroluminescent device according to the invention, it is furthermore preferred to apply one or more layers from solution and one or more layers by a sublimation process.

In accordance with the invention, the electronic devices comprising one or more compounds according to the invention can be employed in displays, as light sources in lighting applications and as light sources in medical and/or cosmetic applications (for example light therapy).

WORKING EXAMPLES

A) Synthesis Examples

A-1) Compounds A

The syntheses were performed according to the following general scheme:

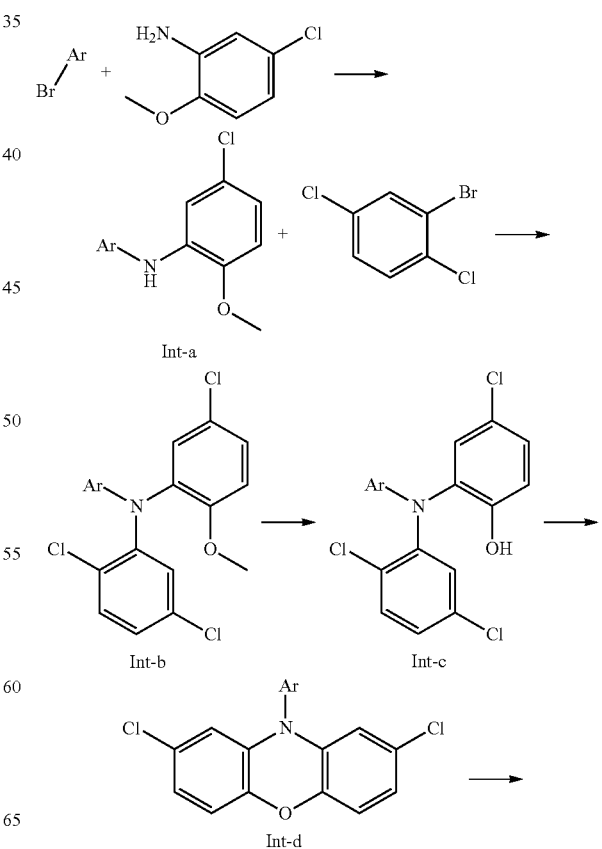

-continued

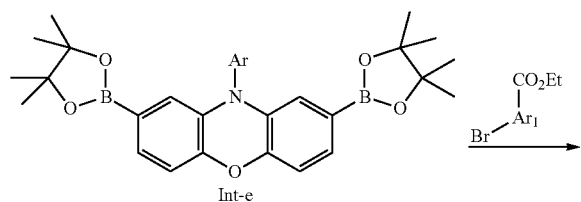
Int-e

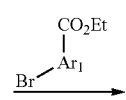

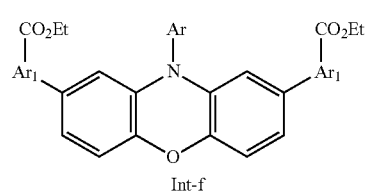
Int-f

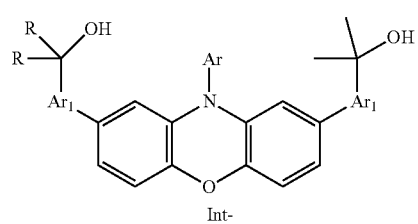
Int-

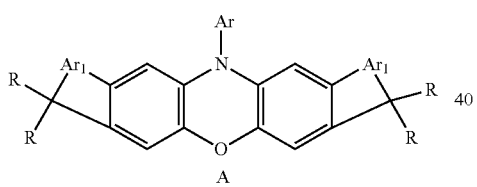
A

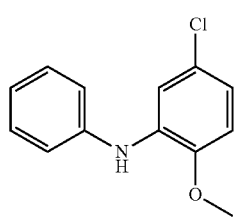
Int-a                                                Yield %

| Int-a1 | 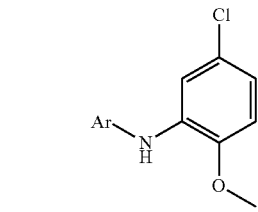 | 73 |

-continued

| | | Yield % |
|---|---|---|
| Int-a | 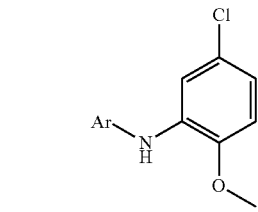 | |
| Int-a2 | 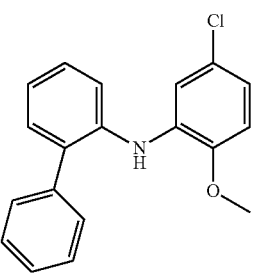 [SMILES: COc1ccc(Cl)cc1Nc1ccccc1-c1ccccc1] | 78 |
| Int-a3 | 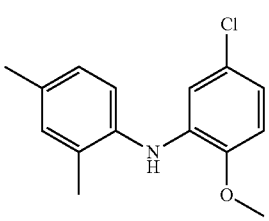 | 69 |
| Int-a4 | 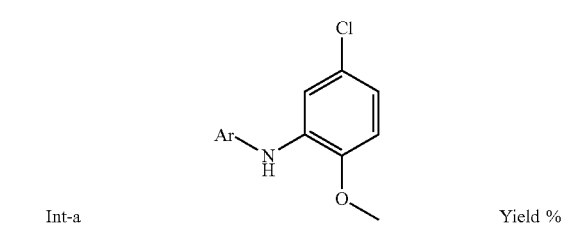 | 83 |

Compound Int-a1

2-chloro-5-methoxy-phenylamine (40.2 g, 0.25 mol), bromobenzene (39.3 g, 0.25 mol) and sodium tert-butoxide (36.1 g, 0.37 mol) are mixed together in 200 ml of toluene. The solution is then degassed and saturated with argon. Afterwards, [1,1'-bis (diphenylphosphino) ferrocene]dichloropalladium (II) (5.49 g, 0.1 mol) is added. The reaction mixture is then heated during 4 hours under reflux and subsequently mixed with water. The collected organic phases are then concentrated under vacuum and the remaining oil is purified on silica gel using heptane. The yield is 42.7 g (0.18 mol, 73% of the theory) and the product is a pink oil.

The compounds Int-a2 to Int-a4 are prepared analogously to Int-a1.

| | | Yield % |
|---|---|---|
| Int-b | Structure with A-N linked to (5-Cl, 2-OMe-phenyl) and (2-Cl, 5-Cl-phenyl) | |
| Int-b1 | Structure: phenyl-N(aryl)(aryl) | 34 |
| Int-b2 | Biphenyl-N(aryl)(aryl) | 45 |
| Int-b3 | 2-biphenyl-N(aryl)(aryl) | 38 |
| Int-b4 | 2,4-dimethylphenyl-N(aryl)(aryl) | 52 |

Compound Int-b1

Int-a1 (100 g, 0.43 mol), 1,4-dichloro-2-iodo-benzene (122.6 g, 0.45 mol) and sodium tert-butoxide (61.7 g, 0.64 mol) are mixed together in 900 ml of toluene. The mixture is degassed and saturated with argon. Thereafter, palladium (II) acetate (1.92 g, 0.008 mol) and tri-tert-butylphosphine (1 mol, I, 0.017 mol) are added. The reaction mixture is heated during 4 hours under reflux and subsequently mixed with water. The collected organic phases are then concentrated under vacuum and the black oil is subsequently subjected to several hot extractions through Alox. The resulting solid is recrystallized from heptane. The yield is 55.4 g (0.15 mol, 34% of the theory) and the product is a white solid.

The compounds Int-b2 to Int-b4 are prepared analogously to Int-b1.

| | | Yield % |
|---|---|---|
| Int-c | Structure with Ar-N linked to (5-Cl, 2-OH-phenyl) and (2-Cl, 5-Cl-phenyl) | |
| Int-c1 | phenyl derivative | 100 |
| Int-c2 | biphenyl derivative | 96 |
| Int-c3 | 2-biphenyl derivative | 98 |

| | Yield % |
|---|---|
| Int-c 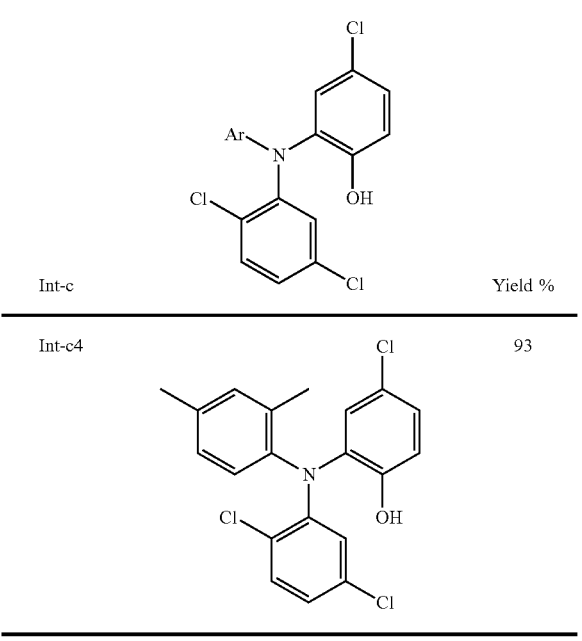 | |
| Int-c4 | 93 |

Compound Int-c1

Int-b1 (53 g, 0.14 mol) is first added to 500 ml anhydrous DCM. Tribromide (35.1 g, 0.14 mol) is then added to the mixture at an internal temperature of −70° C. The mixture is stirred 5 minutes at −70° C. and then the reaction takes place overnight at room temperature. The reaction is then stopped by adding 500 ml water. The collected organic phases are then concentrated under vacuum. A brownish oil remains. The yield is 51 g (0.14 mol, 100% of the theory).

The compounds Int-c2 to Int-c4 are prepared analogously to Int-c1.

| | Yield % |
|---|---|
| Int-d 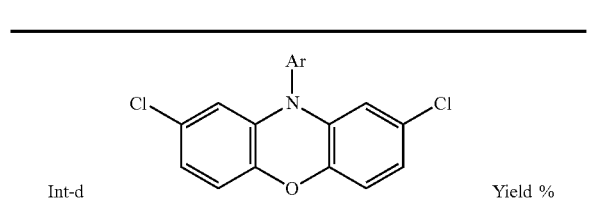 | |
| Int-d1 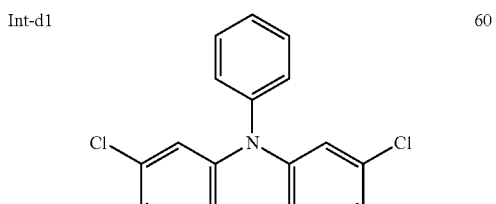 | 60 |
| Int-d2 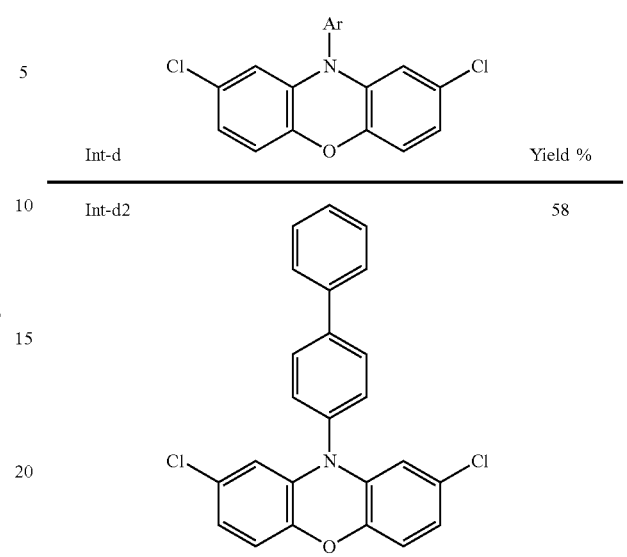 | 58 |
| Int-d3 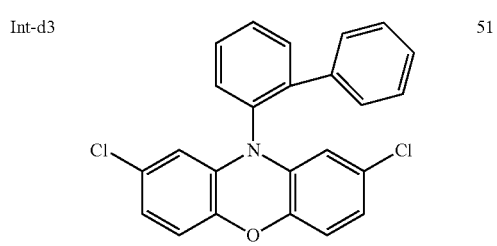 | 51 |
| Int-d4 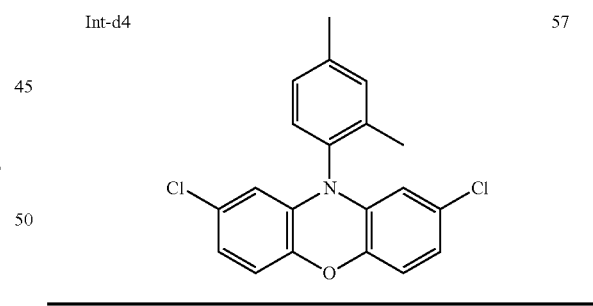 | 57 |

Compound Int-d1

Int-c1 (91.4 g; 0.25 mol), potassium carbonate (52 g; 0.5 mol) and 800 ml DMF are mixed in a flask and the suspension is boiled overnight under reflux. Subsequently, the reaction is cooled down to room temperature and mixed with toluene and water. The collected organic phases are concentrated under vacuum and the remaining solid is recrystallized from a mixture of toluene/heptane. The yield is 49.4 g (60%; 0.15 mol) and the product is a gray solid.

The compounds Int-d2 to Int-d4 are prepared analogously to Int-d1.

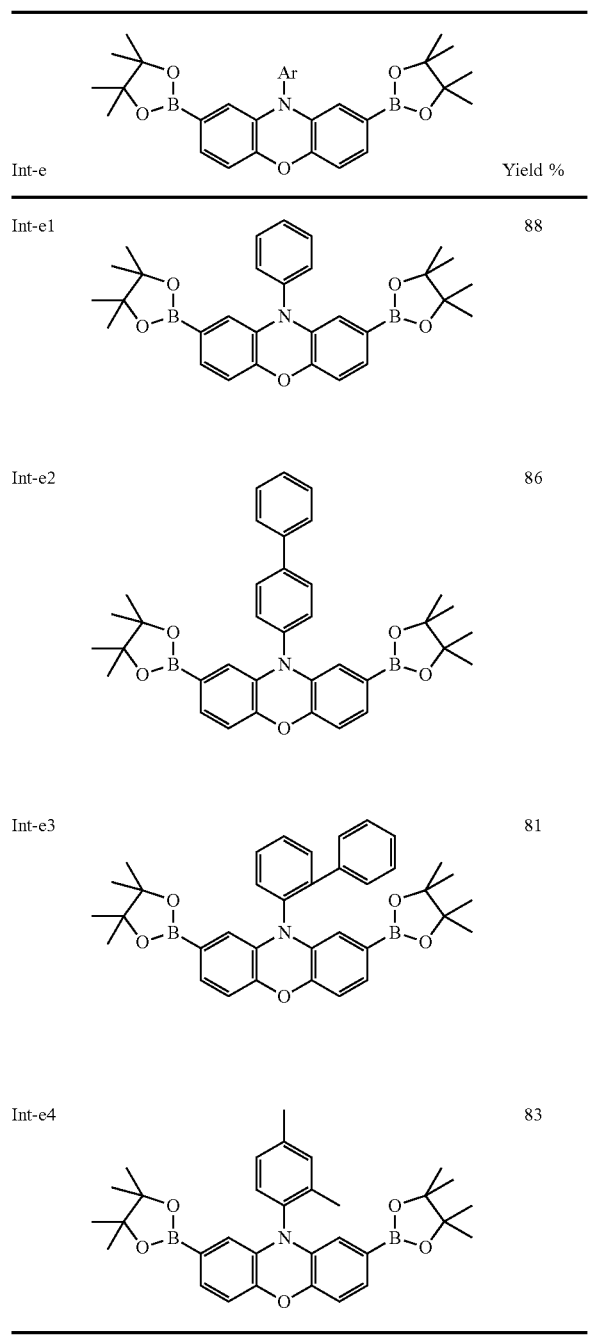

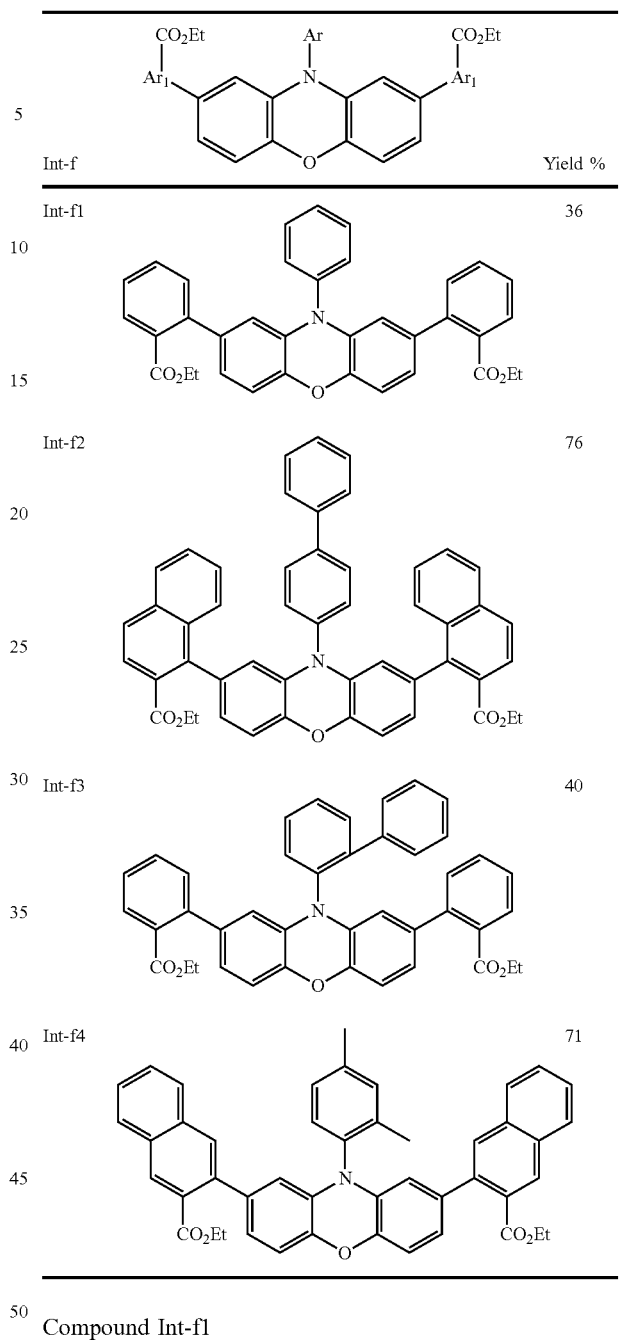

Compound Int-e1

Int-d1 (30.0 g; 91 mmol), bis-pinacolato-diborane (60.4 g; 238 mmol) and potassium acetate (35.9; 366 mmol) are suspended in 600 ml 1,4-dioxane. The solution is degassed and saturated with argon. Transdichloro(biscyclohexylphosphine) palladium(II) (8.1 g; 11 mmol) is then added to the reaction mixture and the reaction boiled overnight under reflux. The suspension is cooled down. The collected organic phases are then concentrated under vacuum and the remaining solid stirred under heat in ethanol. The yield is 46.7 g (0.08 mol, 88% of the theory) and the product is a gray solid.

The compounds Int-e2 to Int-e4 are prepared analogously to Int-e1.

Compound Int-f1

Int-e1 (12 g, 0.02 mol), ethyl 2-bromo-benzoate (11.8 g, 0.05 mol) and tripotassium phosphate monohydrate (21.9 g, 0.095 mol) are suspended in 130 ml toluene, 130 ml of 1,4-dioxane and 130 ml of water. The solution is degassed and saturated with argon. Subsequently, palladium (II) acetate (259 mg; 1.15 mmol) and tri-ortho-tolylphosphine (864 mg; 2.8 mmol) are added to the mixture and the reaction mixture is heated overnight under reflux. The suspension is cooled down to room temperature and the phases are separated. The organic phase is dried and the solvent is spun off. The remaining solid is recrystallized from toluene/heptane. The yield is 4.6 g (8.2 mmol, 36% of the theory) and the product is a gray solid.

The compounds Int-f2 to Int-f4 are prepared analogously to Int-f1.

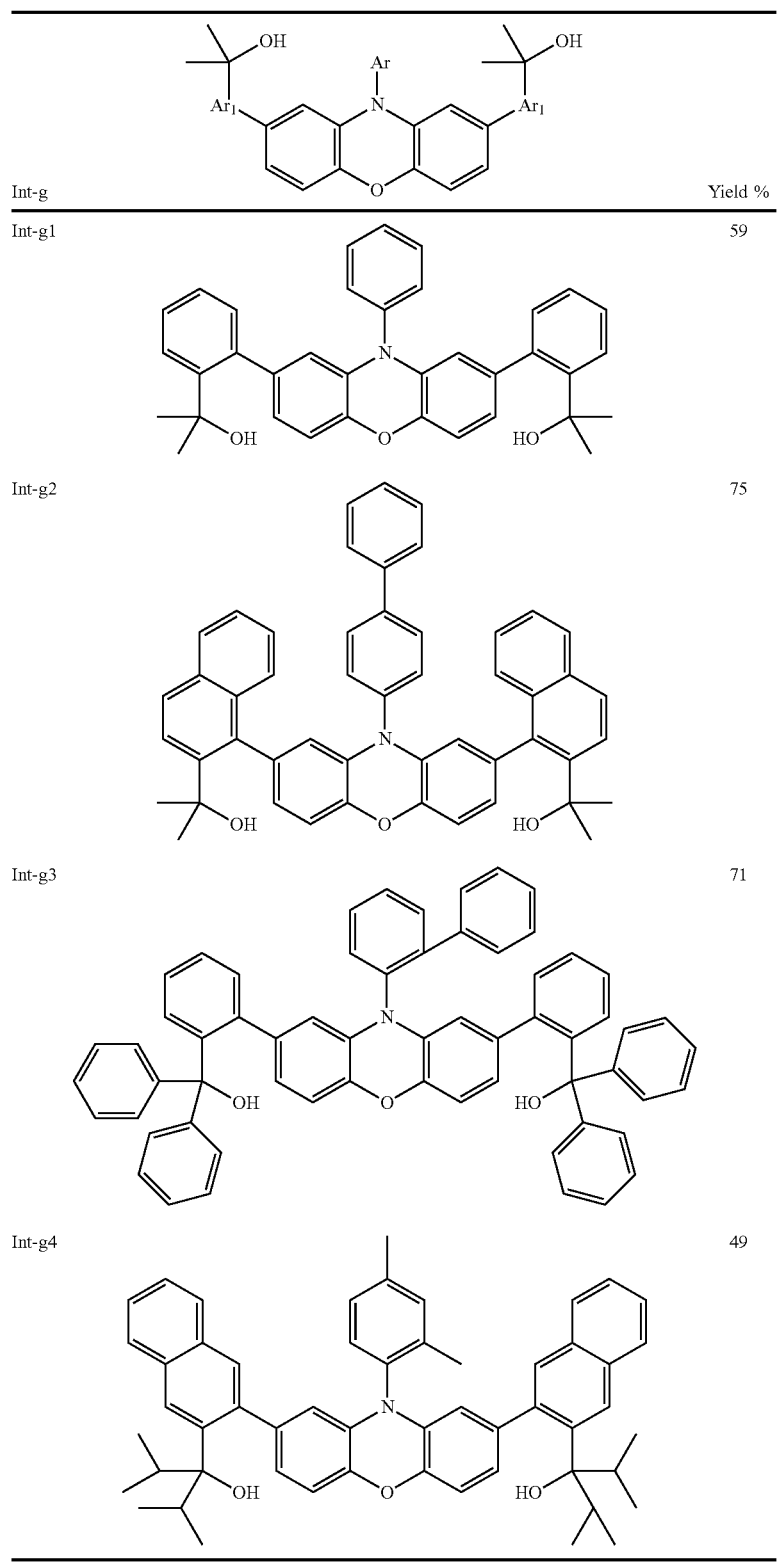

Compound Int-g1

4.99 g (20.25 mmol) of cerium (111) chloride are first added to 65 ml of anhydrous THF. Subsequently, 4.5 g (8.1 mmol) Int-f-1 is added to the reaction mixture, which is then stirred during 30 minutes. Then, 24.3 mL (72.9 mmol) of methyl magnesium chloride are added dropwise in THF (3 M) at 0° C. and the reaction mixture is stirred during 72 h. Subsequently, 100 mL of water are added in order to hydrolyze the reaction mixture. The organic phase is completed with toluene and washed with water. The combined aqueous phases are extracted with toluene three times and are concentrated to dryness under reduced pressure, and then recrystallized from toluene/heptane. The yield is 2.5 g (4.7 mmol; 59% of the theory) and the product is a beige solid.

The compounds Int-g2 to Int-g4 are prepared analogously to Int-g1.

during 2 hours and the reaction is then mixed with ethanol. Water is added so that a phase separation takes place. The organic phase is washed with water, dried and then the solvent is evaporated. The remaining residue is recrystal-

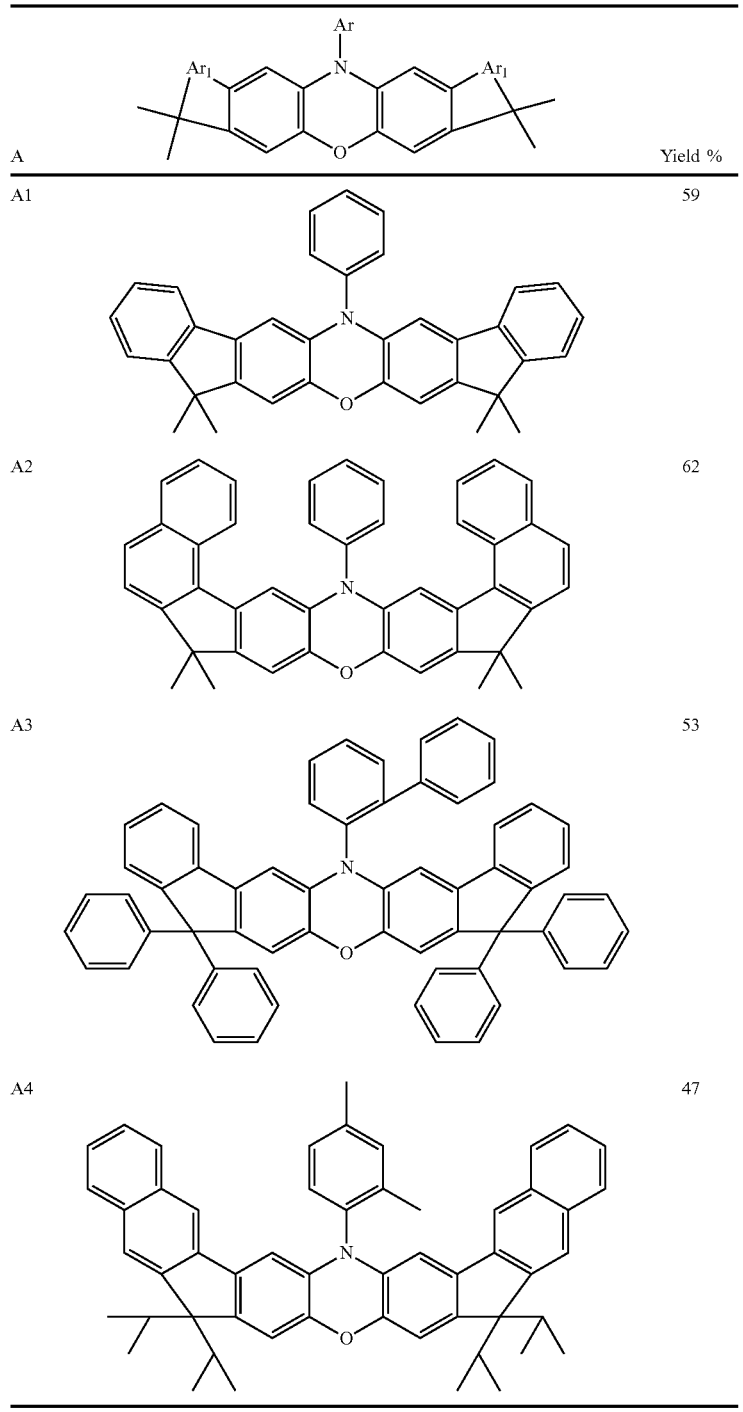

Compound A1

Polyphosphoric acid (3.25 g, 0.3 mol) and methane sulfonic acid (3.15 g, 0.3 mol) are introduced in a flask. Then, a suspension of Int-g1 (2.5 g, 4.7 mmol) in DCM is slowly added in the mixture, dropwise, whereas the mixture is cooled down with an ice bath. The mixture is further stirred lized several times from toluene/heptane. The yield is 1.0 g (1.88 mmol, 40% of the theory). The product is a light-yellow solid.

The compounds A2 to A4 are prepared analogously to A1.

A-2) Compounds B

The syntheses were performed according to the following general scheme:

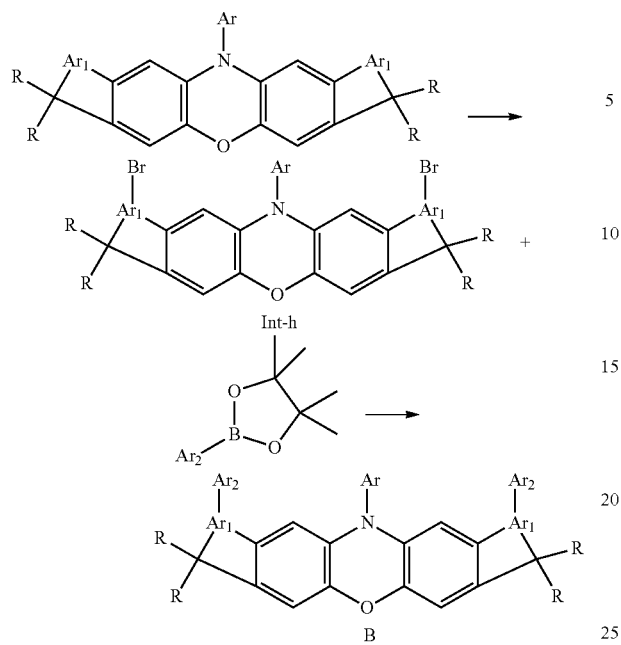

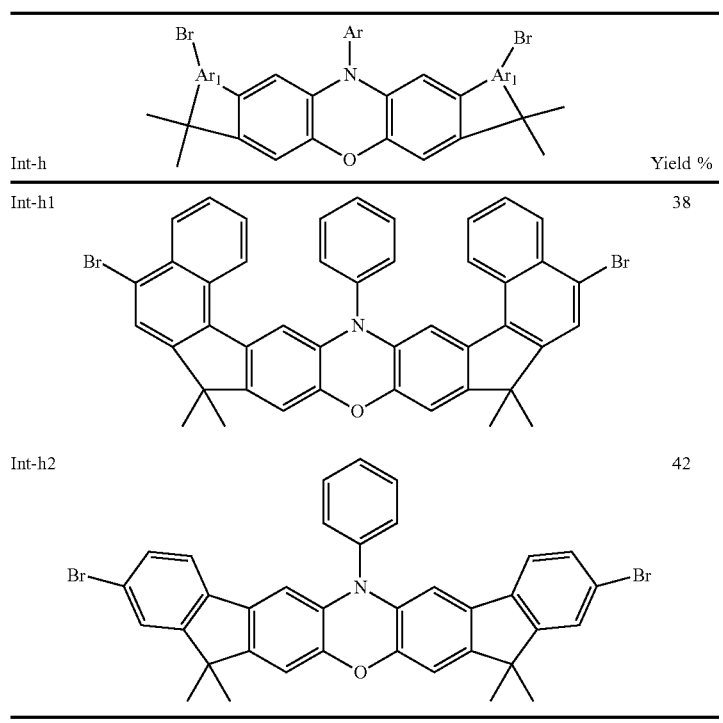

Compound Int-h1

A-2 (4 g; 6.8 mmol) and N-bromosuccinimide (2.47 g, 13.9 mmol) are dissolved in 100 mL DCM and stirred during 16 hours at room temperature. Then, the product is hydrolyzed with 100 mL of water. The organic phase is completed with DCM and washed twice with water. After concentration of the organic phase, the residue is recrystallized from toluene. The product is a yellow solid. The yield is 1.9 g (2.5 mmol; corresponding to 38% of the theory).

The compound Int-h2 is prepared analogously to Int-h1.

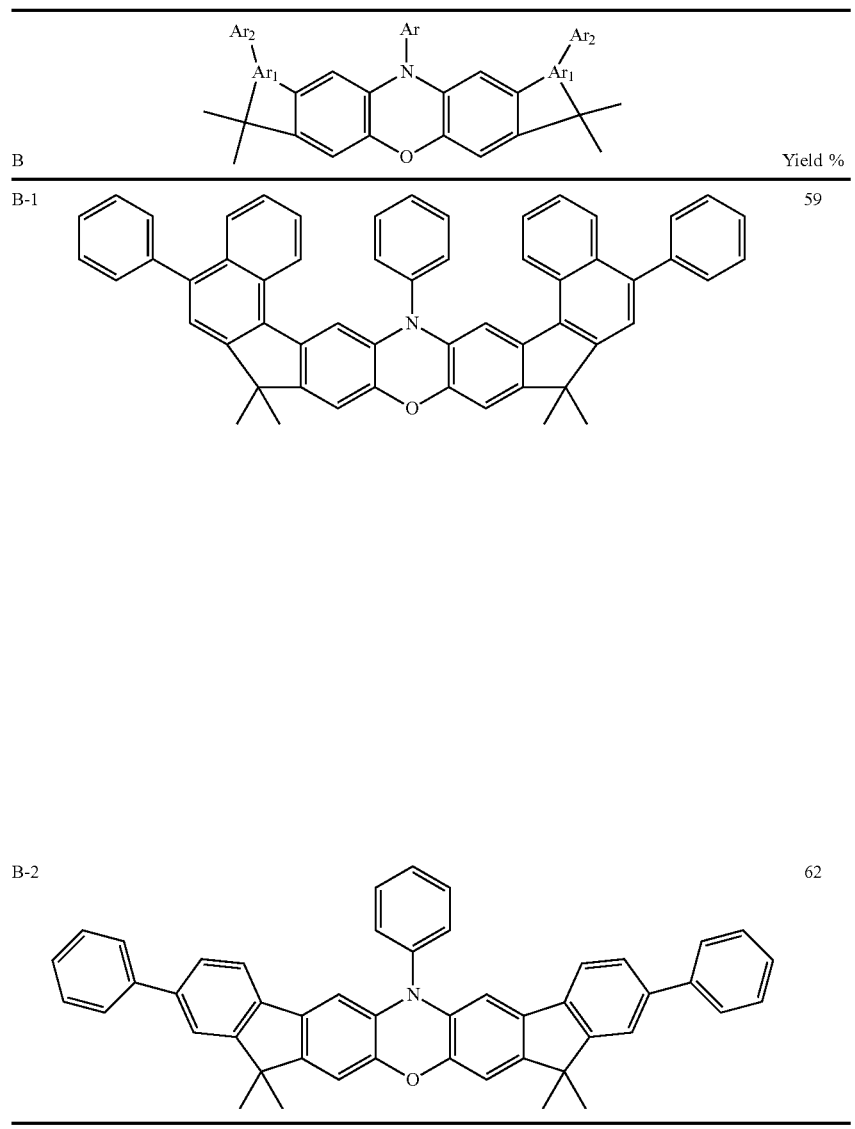

Compound B1

Int-h-1 (5 g; 6.7 mmol), phenylboronic acid (1.8 g, 14.7 mmol) and tripotassium phosphate monohydrate (2.9 g, 29.4 mmol) are suspended in 100 ml of toluene, 100 ml of 1,4-dioxane and 100 ml of water. The solution is degassed and saturated with argon. Subsequently, palladium (II) acetate (45 mg; 0.2 mmol) and tri-ortho-tolylphosphine (146 mg; 0.48 mmol) are added and the reaction mixture is heated overnight under reflux. The suspension is then cooled down to room temperature and the phases are separated. The organic phase is filtered through alumina, dried, and the solvent is spun off. The remaining solid is recrystallized from toluene/heptane. The yield is 2.9 g (3.9 mmol, 59% of the theory) and the product is a gray solid.

The compound B2 is prepared analogously to B1.

A-3) Compounds C

The syntheses were performed according to the following general scheme:

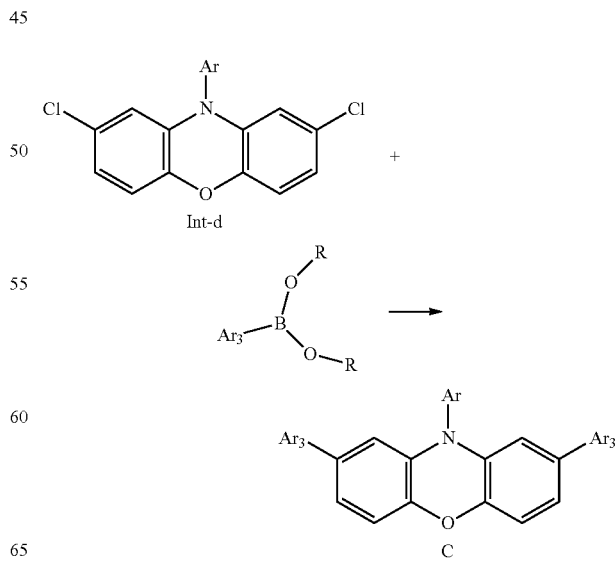

| C | 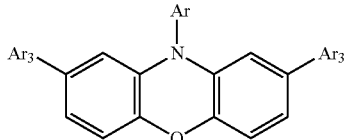 | Yield % |
|---|---|---|
| C1 | 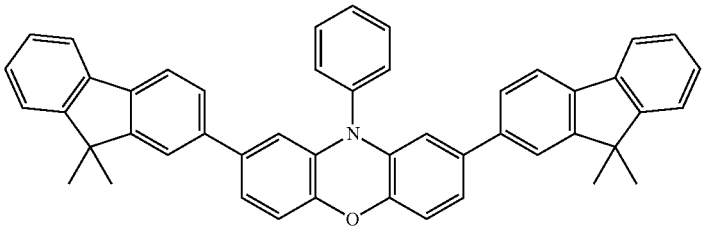 [SMILES: CC1(C)c2ccccc2-c2ccc(-c3ccc4c(c3)N(c3ccccc3)c3cc(-c5ccc6c(c5)C(C)(C)c5ccccc5-6)ccc3O4)cc21] | 44 |
| C2 | 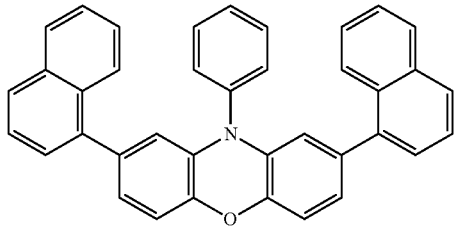 [SMILES: c1ccc(N2c3cc(-c4cccc5ccccc45)ccc3Oc3ccc(-c4cccc5ccccc45)cc32)cc1] | 43 |
| C3 | 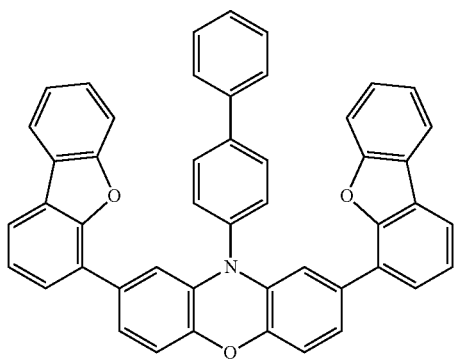 [SMILES: c1ccc(-c2ccc(N3c4cc(-c5cccc6c5oc5ccccc56)ccc4Oc4ccc(-c5cccc6c5oc5ccccc56)cc43)cc2)cc1] | 52 |
| C4 | 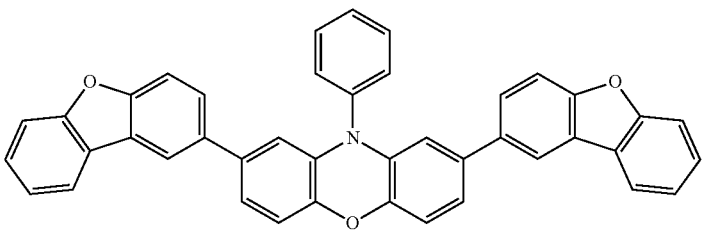 [SMILES: c1ccc(N2c3cc(-c4ccc5oc6ccccc6c5c4)ccc3Oc3ccc(-c4ccc5oc6ccccc6c5c4)cc32)cc1] | 27 |
| C5 | 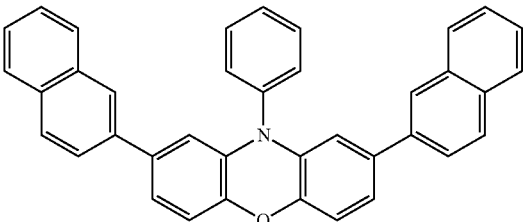 | 33 |

Compound C1

Int-d1 (0.99 g; 3 mmol), 2-(9,9-dimethylfluorene)-4,4,5,5-tetramethyldioxaborolane (2.38 g; 7 mmol) and cesium fluoride (1.86 g, 0:01 mmol) are suspended in 50 ml of 1,4-dioxane. The solution is degassed and saturated with argon. Subsequently, transdichloro(biscyclohexylphosphine) palladium (II) (23 mg; 0.32 mmol) is added to the reaction mixture, which is boiled overnight under reflux. The suspension is cooled down and then mixed with water. The collected organic phases are concentrated under vacuum and the remaining solid is repeatedly purified by hot extraction (toluene over Alox) and recrystallization. The yield is 0.694 g (1.08 mol, 44% of the theory) and the product is a yellow solid.

The compounds C2 to C4 are prepared analogously to C1.

A-4) Compounds D

The syntheses were performed according to the following general scheme:

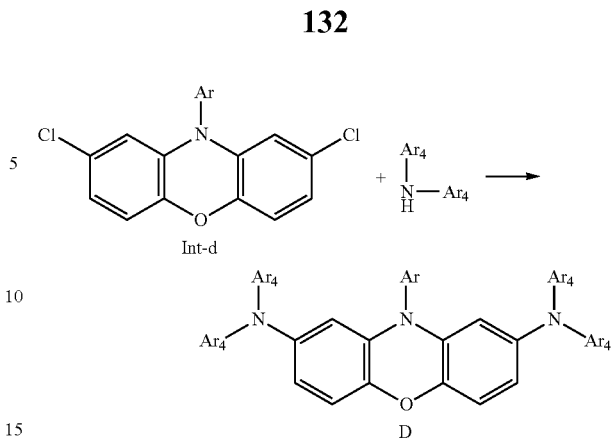

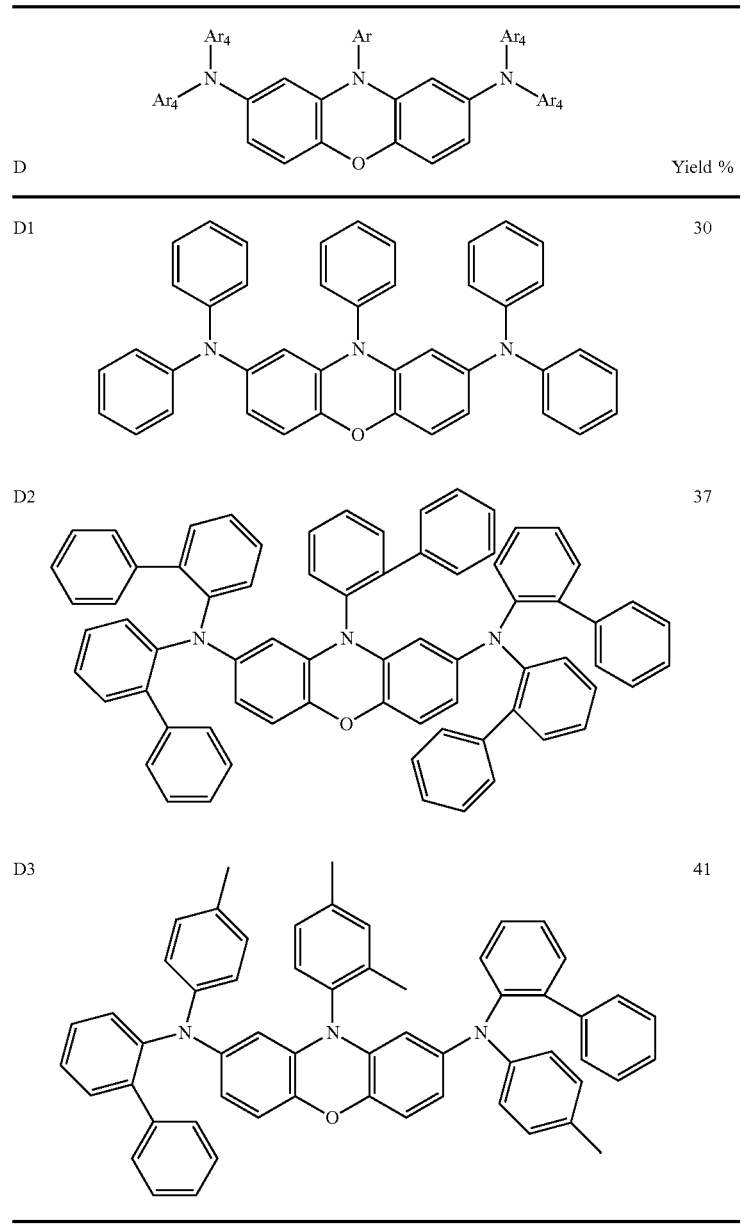

| | D | Yield % |
|---|---|---|
| D1 | | 30 |
| D2 | | 37 |
| D3 | | 41 |

Compound D1

Int-d1 (332 mg; 1 mmol), diphenylamine (376 mg 2.2 mmol) and sodium tert-butoxide (290 mg; 3 mmol) are suspended in 10 mL toluene. After addition of 90 mg (0.12 mmol) of trans-dichlorobis(tricyclohexylphosphine) palladium (II), the reaction mixture is then mixed under reflux during 16 h. After cooling to room temperature, the organic phase is completed with toluene and afterwards, the organic phase is extracted three times with water. The organic phase is subsequently concentrated and filtered through alumina. The product is obtained by recrystallization from toluene/heptane as a colorless solid. Yield: 180 mg (0.3 mmol, 30% of the theory.)

The compounds D2 to D3 are prepared analogously to D1.

A-5) Compounds E

The syntheses were performed according to the following general scheme:

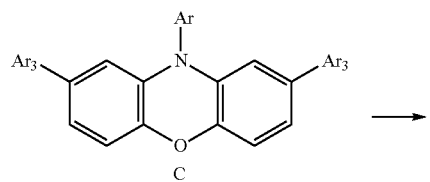

C

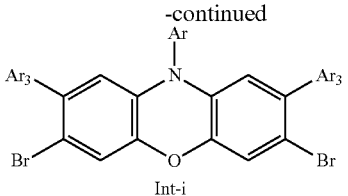

Int-i

-continued

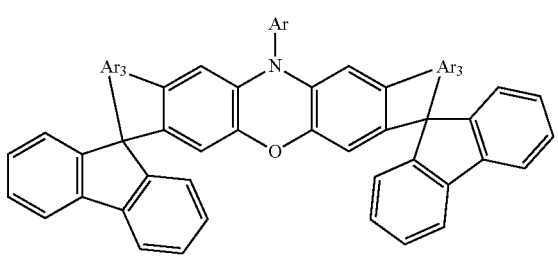

E

Compounds Int-i

Compounds Int-i are prepared analogously to compounds Int-h.

| Int-i | | Yield % |
|---|---|---|
| Int-i-1 | 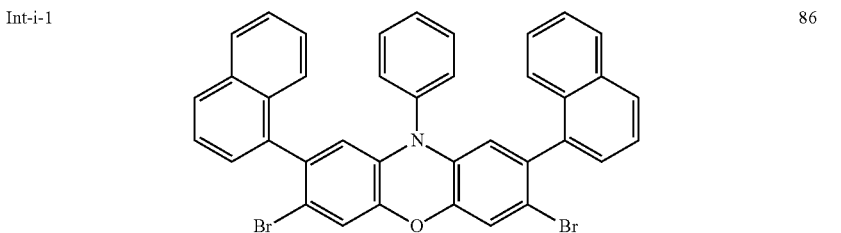 | 86 |
| Int-i-2 | 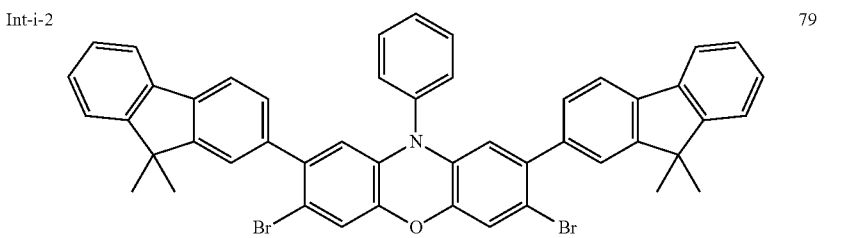 | 79 |

-continued
| Int-i | 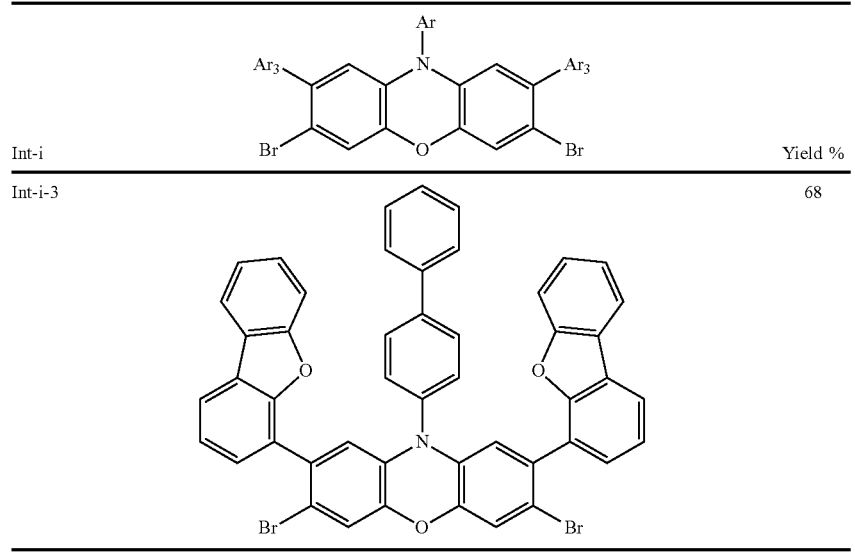 | Yield % |
|---|---|---|
| Int-i-3 | | 68 |
Compounds E
| E | 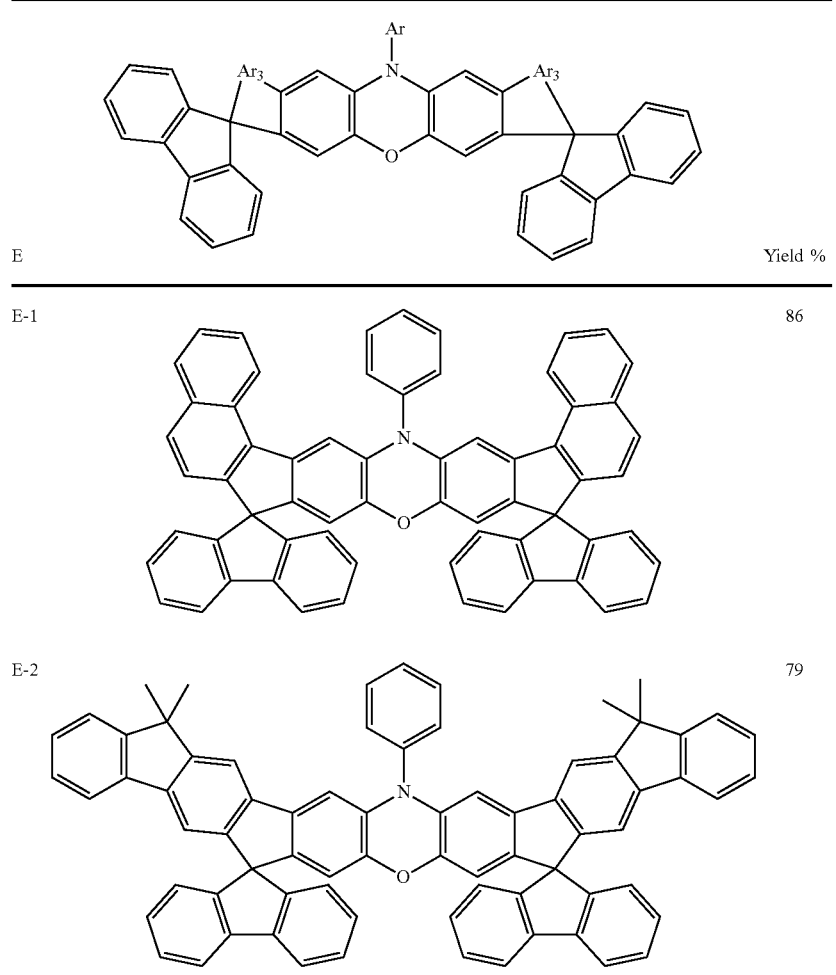 | Yield % |
|---|---|---|
| E-1 | | 86 |
| E-2 | | 79 |

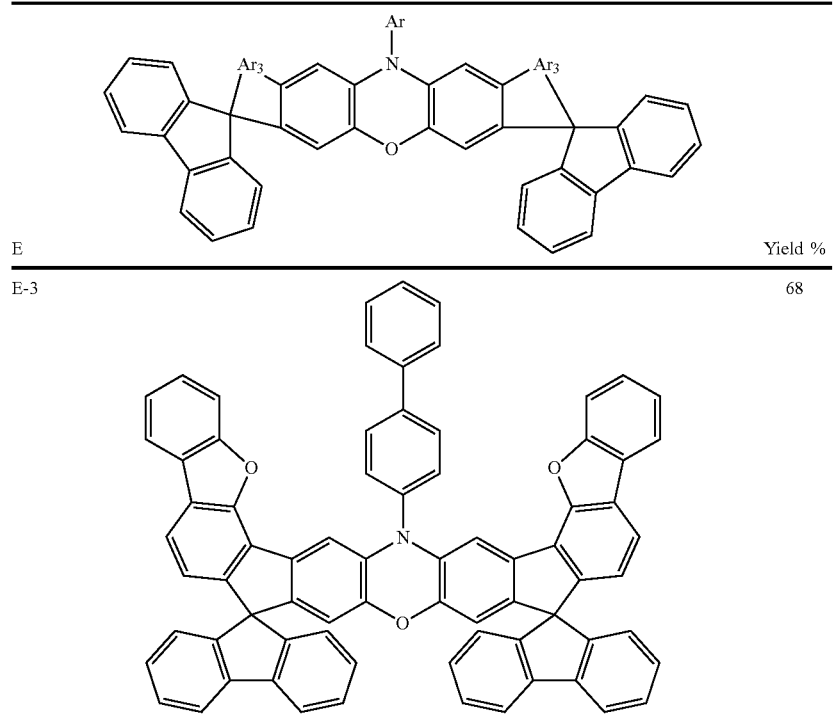

| E | Yield % |
|---|---|
| E-3 | 68 |

Compound E1

Int-i-1 (3.75 g; 5.4 mmol) is added to 80 ml of THF and cooled down to −78° C. Subsequently, at this temperature, a solution of 5.5 mL (13.75 mmol) n-BuLi (2.5 M in hexane) is added dropwise to the reaction mixture, which is further stirred at this temperature during two hours. Then, 2.15 g (13.8 mmol) of fluorene-9-one is added and the mixture is heated until room temperature within 16 hours. The reaction mixture is hydrolyzed with 50 mL of water and the organic phase is completed with toluene. The organic phase is washed several times with water and then concentrated. The solid obtained is dissolved in 200 mL toluene and mixed with 5 g Amberlyst 15. It is further mixed under reflux during 3 hours. After cooling to room temperature, the reaction mixture is filtered through alumina and concentrated under reduced pressure. Further purification is carried out by recrystallization from toluene/heptane. The yield is 3.1 g (3.7 mmol; 68.5% of the theory) and the product is a yellow solid. Yield: 3.1 g.

The compounds E2 to E3 are prepared analogously to E1.

B) Device Examples

Fabrication of OLED Devices

The manufacturing of the OLED devices is performed accordingly to WO 2004/05891 with adapted film thicknesses and layer sequences. The following examples V1 to E6 (see Table 1) show data of various OLED devices.

Substrate Pre-Treatment of Examples V1-E5:

Glass plates with structured ITO (50 nm, indium tin oxide) are coated with 20 nm PEDOT:PSS (Poly(3,4-ethylenedioxythiophene) poly(styrenesulfonate, CLEVIOS™ P VP AI 4083 from Heraeus Precious Metals GmbH Germany, spin-coated from a water-based solution) to form the substrates on which the OLED devices are fabricated.

The OLED devices have in principle the following layer structure:

Substrate,
ITO (50 nm),
Buffer (20 nm),
Hole injection layer (see table 1) (20 nm),
Hole transporting layer (HTL1) (see table 1),
Emissive layer (EML) (see table 1) (20 nm),
Electron transporting layer (ETL 50%, EIL 50%) (30 nm),
Electron injection layer (EIL) (3 nm),
Cathode.

The cathode is formed by an aluminium layer with a thickness of 100 nm. The detailed stack sequence is shown in Table 1. The materials used for the OLED fabrication are presented in Table 3.

All materials are applied by thermal vapour deposition in a vacuum chamber. The emission layer here always consists of at least one matrix material (host material=H) and an emitting dopant (emitter=D), which is mixed with the matrix material or matrix materials in a certain proportion by volume by co-evaporation. An expression such as H1:D1 (97%:3%) here means that material H1 is present in the layer in a proportion by volume of 97%, whereas D1 is present in the layer in a proportion of 3%. Analogously, the electron-transport layer may also consist of a mixture of two or more materials.

The OLED devices are characterised by standard methods. For this purpose, the electroluminescence spectra, the current efficiency (measured in cd/A) and the external quantum efficiency (EQE, measured in % at 1000 cd/m$^2$) are determined from current/voltage/luminance characteristic lines (IUL characteristic lines) assuming a Lambertian emission profile. The electroluminescence (EL) spectra are recorded at a luminous density of 1000 cd/m$^2$ and the CIE 1931 x an y coordinates are then calculated from the EL spectrum. EQE @ 1000 cd/m$^2$ is defined as the external quantum efficiency at luminous density of 1000 cd/m$^2$. For all experiments, the lifetime LT95 is determined. The lifetime LT95 @1000 cd/m² is defined as the time after which the initial luminous density of 1000 cd/m² has dropped by 5%. The device data of various OLED devices is summarized in Table 2. The examples V1 and V2 are comparative examples according to the state-of-the-art. The examples E1 to E6 show data of inventive OLED devices.

In the following section several examples are described in more detail to show the advantages of the inventive OLED devices.

Use of Inventive Compounds as Transporting Material in Fluorescent OLEDs

The inventive compounds are especially suitable as hole injecting and transporting materials in fluorescent blue emissive layers of OLED devices, represented by HIM2, HTM3, HTM4 and HTM5. Comparative examples for the state-of-the-art are represented by HIM1, HTM1 and HTM2.

Example E1 demonstrates the suitable application of the inventive compound as a hole injecting material, thereby yielding comparable external quantum efficiency but with an increased device lifetime compared to the state-of-the-art example V1.

The use of the inventive compounds as hole transporting material results in significantly improved OLED device data (see E2, E3 and E4) with respect to device lifetime compared to state-of-the-art example (V2). The comparison of V2 and E2 shows the improvement of the present invention by use if a symmetric substitution pattern, which yields significantly increased lifetime.

Use of Inventive Compounds as Emitting Material in Fluorescent OLEDs

The inventive compounds are expecially suitable as an emitter (dopant) material when blended into a fluorescent blue matrix to form the emissive layer of a fluorescent blue OLED device. The representative compounds of the invention are D1 and D2. Comparative example for the state-of-the-art is represented by VD2.

The use of the inventive compounds as an emitter (dopant) in a fluorescent blue OLED results in significantly improved device data (E5 and E6) compared to the state-of-the-art example (V2), both in terms of external quantum efficiency and lifetime.

TABLE 1

Stack sequence of OLED devices

| Examples | HIL (20 nm) | HTL (20 nm) | EML (20 nm) |
|---|---|---|---|
| V1 | HIL1:HIM1 | HTM1 | BH1 (95%):VD1 (5%) |
| E1 | HIL1:HIM2 | HTM1 | BH1 (95%):VD1 (5%) |
| V2 | HIL1:HIM1 | HTM2 | BH1 (97%):VD2 (3%) |
| E2 | HIL1:HIM1 | HTM3 | BH1 (97%):VD2 (3%) |
| E3 | HIL1:HIM1 | HTM4 | BH2 (97%):VD2 (3%) |
| E4 | HIL1:HIM1 | HTM5 | BH1 (97%):VD2 (3%) |
| E5 | HIL1:HIM1 | HTM2 | BH1 (97%):D1 (3%) |
| E6 | HIL1:HIM1 | HTM2 | BH1 (97%):D2 (3%) |

TABLE 2

OLED device data

| Examples | CIE x | CIE y | EQE [%] @ 1000 cd/m² | LT 95 [h] @ 1000 cd/m² |
|---|---|---|---|---|
| V1 | 0.14 | 0.16 | 7.9 | 100 |
| E1 | 0.13 | 0.16 | 8.2 | 140 |
| V2 | 0.14 | 0.19 | 6.1 | 20 |
| E2 | 0.14 | 0.19 | 6.0 | 40 |
| E3 | 0.14 | 0.18 | 6.1 | 50 |
| E4 | 0.14 | 0.18 | 6.3 | 50 |
| E5 | 0.14 | 0.19 | 7.0 | 40 |
| E6 | 0.13 | 0.16 | 6.9 | 50 |

TABLE 3

Chemical structure of OLED materials

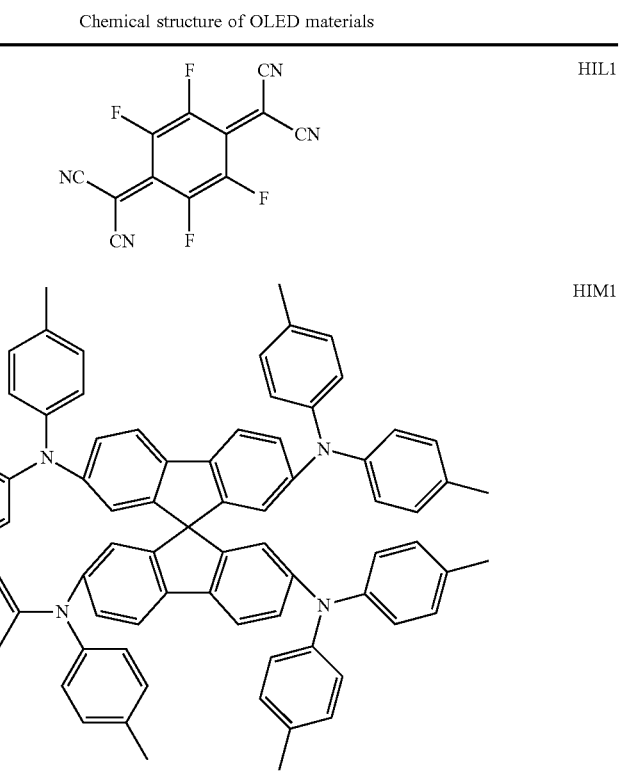

TABLE 3-continued
Chemical structure of OLED materials
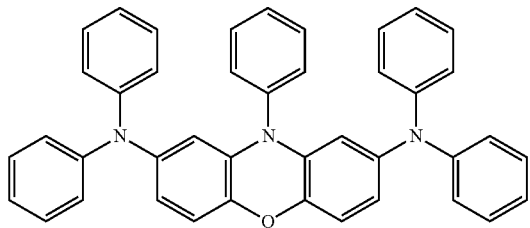 [SMILES: c1ccc(N(c2ccccc2)c2ccc3c(c2)N(c2ccccc2)c2cc(N(c4ccccc4)c4ccccc4)ccc2O3)cc1]
HIM2
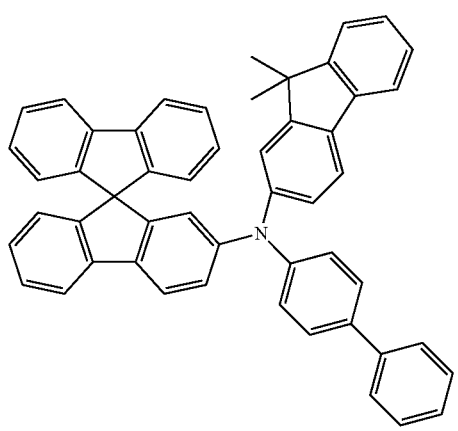 [SMILES: CC1(C)c2ccccc2-c2ccc(N(c3ccc(-c4ccccc4)cc3)c3ccc4c(c3)C3(c5ccccc5-c5ccccc53)c3ccccc3-4)cc21]
HTM1
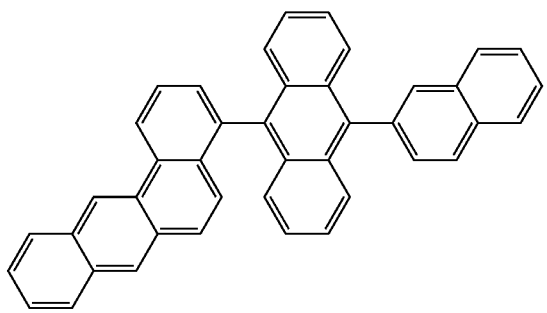 [SMILES: c1ccc2cc(-c3c4ccccc4c(-c4cccc5c4ccc4cc6ccccc6cc45)c4ccccc34)ccc2c1]
BH1
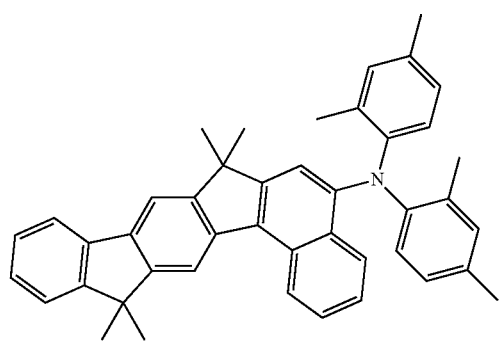 [SMILES: Cc1ccc(N(c2ccc(C)cc2C)c2cc3c(c4ccccc24)-c2cc4c(cc2C3(C)C)-c2ccccc2C4(C)C)c(C)c1]
VD-1

TABLE 3-continued
Chemical structure of OLED materials
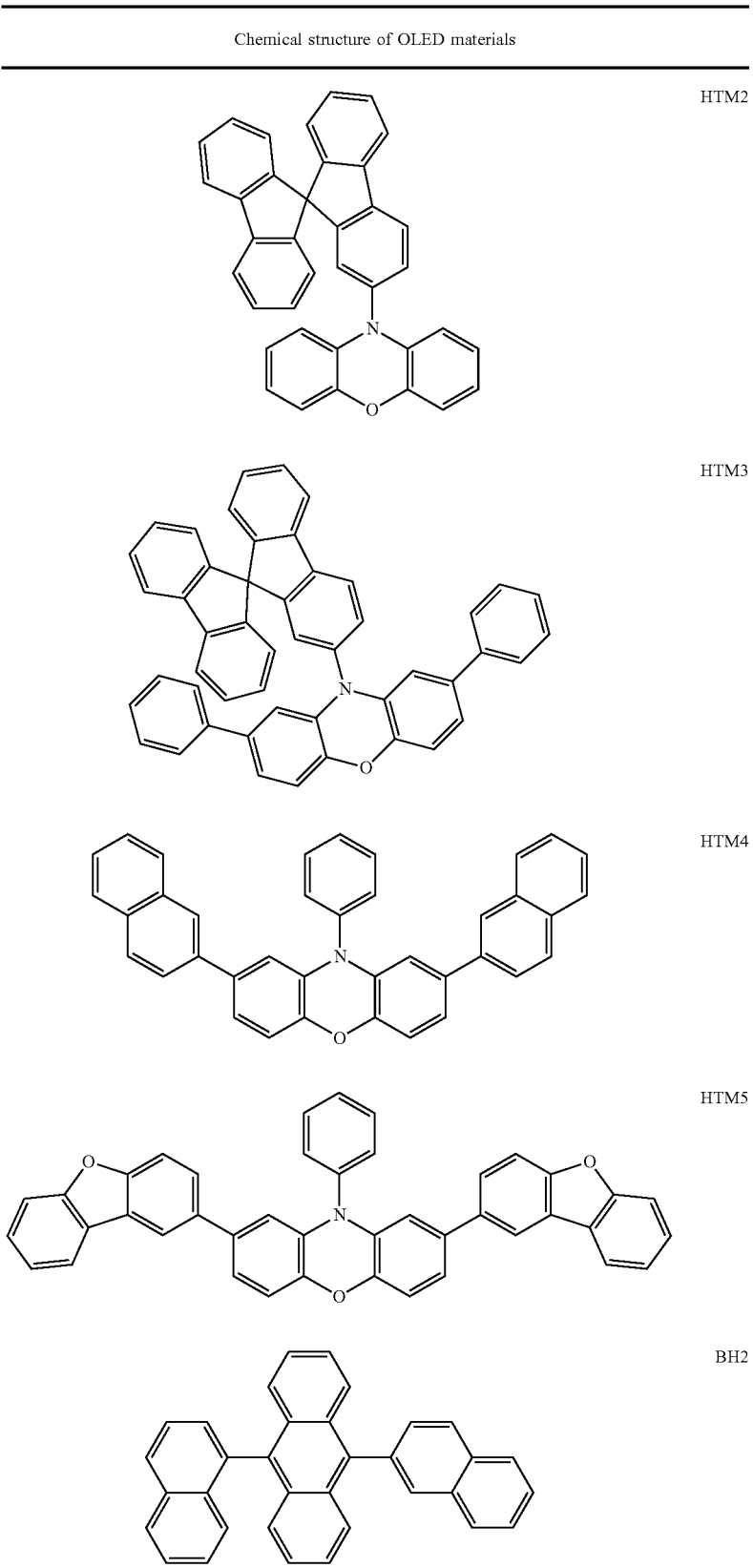
HTM2
HTM3
HTM4
HTM5
BH2

TABLE 3-continued
Chemical structure of OLED materials
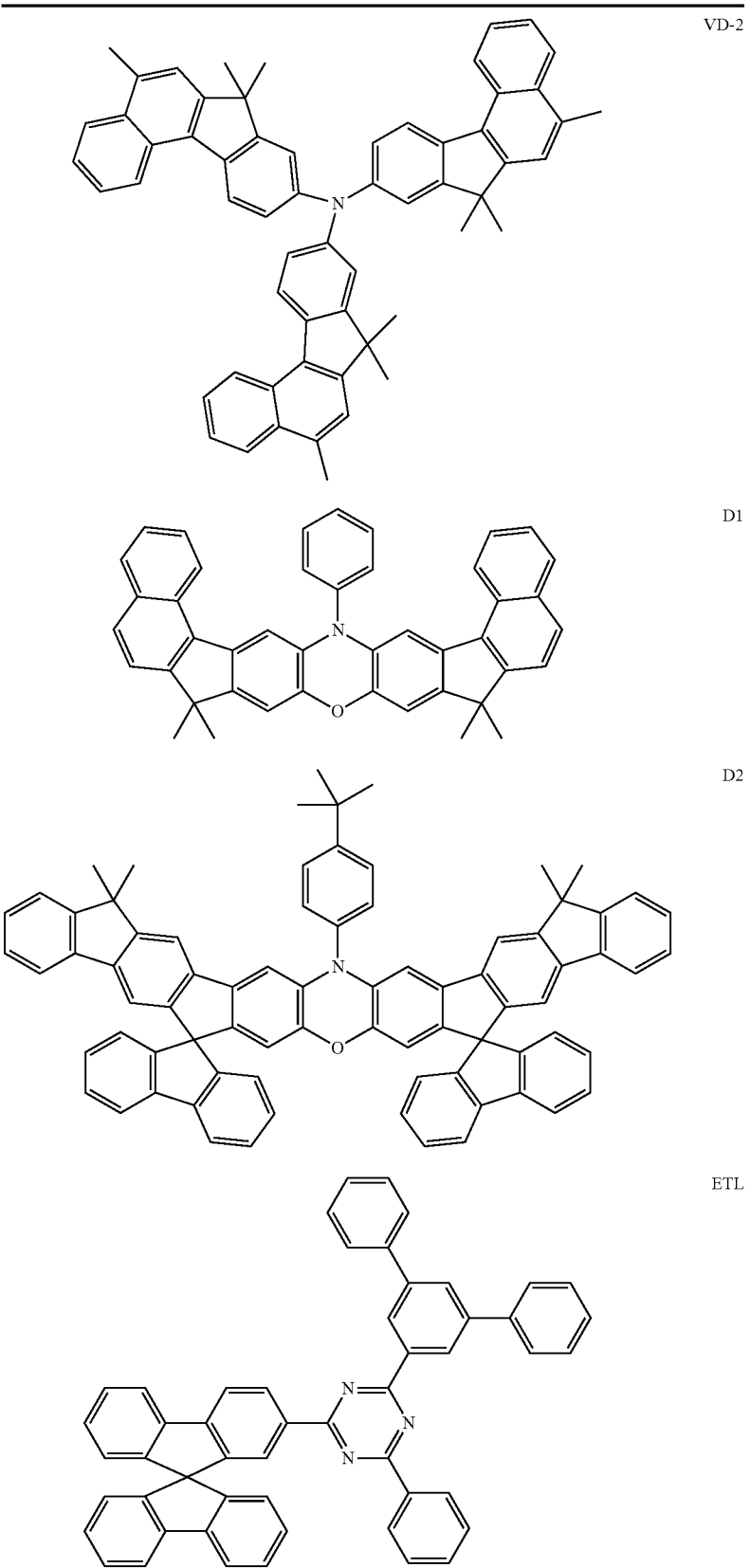
VD-2
D1
D2
ETL TABLE 3-continued Chemical structure of OLED materials

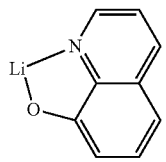

EIL

The invention claimed is:
1. A compound of formula (1):

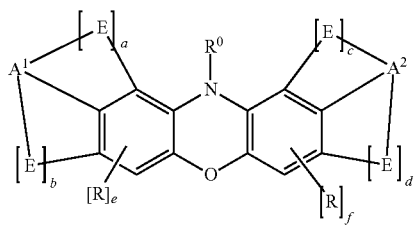

(1)

wherein
A$^1$ and A$^2$
are, on each occurrence, identically or differently, selected from the group consisting of Ar$^1$ and N(Ar$^2$)$_2$;
E is on each occurrence, identically or differently, a divalent bridge selected from the group consisting of B(R$^1$), C(R$^1$)$_2$, Si(R$^1$)$_2$, C=O, C=NR$^1$, C=C(R$^1$)$_2$, O, S, S=O, SO$_2$, N(R$^1$), P(R$^1$), and P(=O)R$^1$;
or
E is a group of formula (E-1):

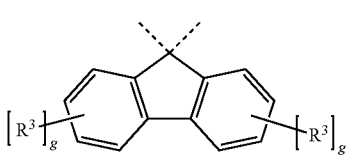

(E-1)

wherein
the dashed bonds denote the bonds to the phenoxazine structure and to A$^1$ or A$^2$;
Ar$^1$ and Ar$^2$
are, on each occurrence, identically or differently, selected from the group consisting of aromatic and heteroaromatic ring systems having 5 to 30 aromatic ring atoms, which are optionally substituted by one or more radicals R$^2$, wherein two groups Ar$^2$ are optionally linked to one another and optionally define a ring;
R, R$^0$, R$^1$, and R$^2$
are on each occurrence, identically or differently, H, D, F, Br, Cl, I, C(=O)R$^3$, CN, Si(R$^3$)$_3$, N(R$^3$)$_2$, P(=O)(R$^3$)$_2$, S(=O)R$^3$, S(=O)$_2$R$^3$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, wherein the above-mentioned groups are each optionally substituted by one or more radicals R$^3$ and wherein one or more CH$_2$ groups in the above-mentioned groups are optionally replaced by —R$^3$C=CR$^3$—, —C≡C—, Si(R$^3$)$_2$, C=O, C=NR$^3$, —C(=O)O—, —C(=O)NR$^3$—, NR$^3$, P(=O)(R$^3$), —O—, —S—, SO, or SO$_2$, an aromatic or heteroaromatic ring system having 5 to 30 aromatic ring atoms, which in each case is optionally substituted by one or more radicals R$^3$, or an aryloxy or heteroaryloxy group having 5 to 30 aromatic ring atoms, which is optionally substituted by one or more radicals R$^3$, wherein two radicals R$^1$, attached to the same C or Si atom are optionally linked to one another and optionally define an aliphatic or aromatic ring and wherein two adjacent radicals R$^2$ are optionally linked to one another and optionally define an aliphatic or aromatic ring;
R$^3$ is on each occurrence, identically or differently, H, D, F, Br, Cl, I, C(=O)R$^4$, CN, Si(R$^4$)$_3$, N(R$^4$)$_2$, P(=O)(R$^4$)$_2$, S(=O)R$^4$, S(=O)$_2$R$^3$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, wherein the above-mentioned groups are optionally substituted by one or more radicals R$^4$ and wherein one or more CH$_2$ groups in the above-mentioned groups are optionally replaced by —R$^4$C=CR$^4$—, —C≡C—, Si(R$^4$)$_2$, C=O, C=NR$^4$, —C(=O)O—, —C(=O)NR$^4$—, NR$^4$, P(=O)(R$^4$), —O—, —S—, SO, or SO$_2$, an aromatic or heteroaromatic ring system having 5 to 30 aromatic ring atoms, which in each case is optionally substituted by one or more radicals R$^4$, or an aryloxy or heteroaryloxy group having 5 to 30 aromatic ring atoms, which is optionally substituted by one or more radicals R$^4$, wherein two adjacent radicals R$^3$ are optionally linked to one another and optionally define an aliphatic or aromatic ring;
R$^4$ is on each occurrence, identically or differently, H or an aliphatic, aromatic and/or heteroaromatic hydrocarbon radical having 1 to 20 C atoms wherein one or more H atoms are optionally replaced by F; and wherein two adjacent radicals R$^4$ together optionally define a mono- or polycyclic aliphatic or aromatic ring system;
a, b, c, and d
are on each occurrence, identically or differently, selected from 0 or 1; wherein a=0, b=0, c=0, or d=0 denotes that the corresponding bridge is not present;
wherein
a+b=0, 1, or 2; and
c+d=0, 1, or 2;
wherein
a+b=0 when A$^1$ is N(Ar$^2$)$_2$; and
c+d=0 when A$^2$ is N(Ar$^2$)$_2$;

e is 0, 1, 2, or 3 and a+b+e≤3;
f is 0, 1, 2, or 3 and c+d+f≤3; and
g is 0, 1, 2, 3, or 4.

2. The compound of claim 1, wherein $A^1$ is $Ar^1$ and a+b=0 or 1 and/or $A^2$ is $Ar^1$ and c+d=0 or 1.

3. The compound of claim 1, wherein E is on each occurrence, identically or differently, a divalent bridge selected from the group consisting of $C(R^1)_2$, $Si(R^1)_2$, O, and S, or E is a group of formula (E-1).

4. The compound of claim 1, wherein both $A^1$ and $A^2$ are $Ar^1$ and a+b=0 or 1 and c+d=0 or 1.

5. The compound of claim 1, wherein the compound is selected from group consisting of compounds of formulae (2) through (7):

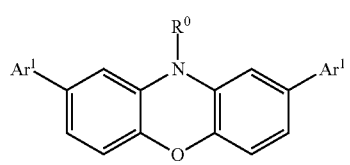

formula (2)

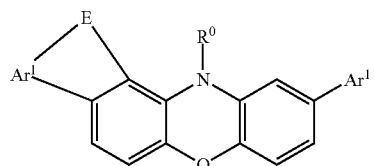

formula (3)

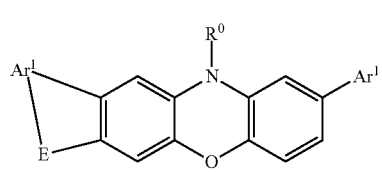

formula (4)

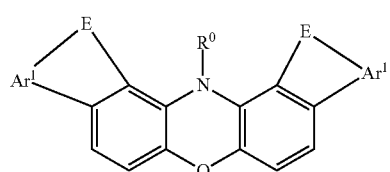

formula (5)

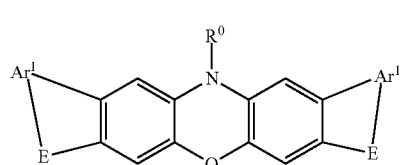

formula (6)

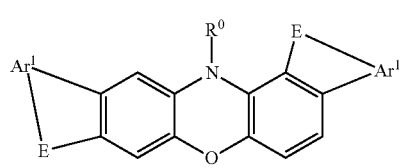

formula (7)

wherein
each free position of the two phenyl rings of the phenoxazine structure of the compounds of formulae (2) through (7) is optionally substituted by a radical R.

6. The compound of claim 1, wherein $Ar^1$ is selected, identically or differently, from the group consisting of aromatic and heteroaromatic ring systems having 5 to 14 aromatic ring atoms, which are optionally substituted by one or more radicals $R^2$.

7. The compound of claim 1, wherein the compound is selected from the group consisting of compounds of formulae (2a) through (7a):

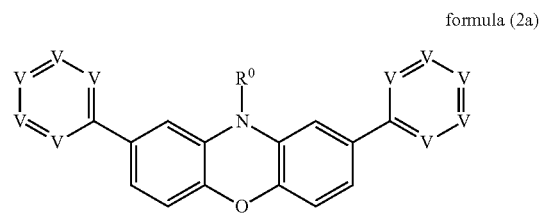

formula (2a)

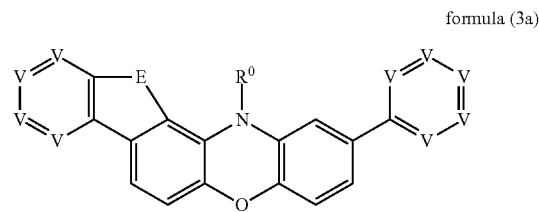

formula (3a)

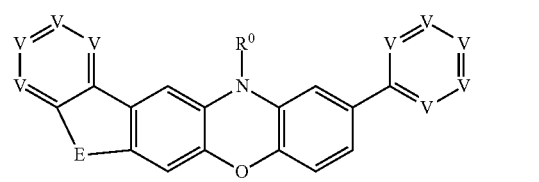

formula (4a)

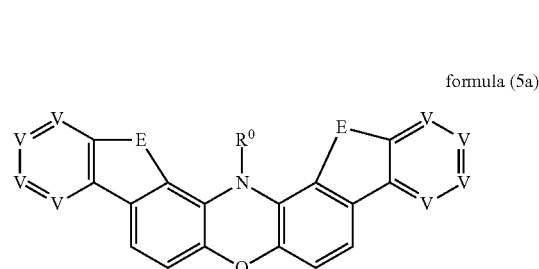

formula (5a)

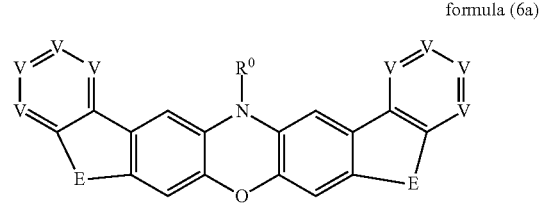

formula (6a)

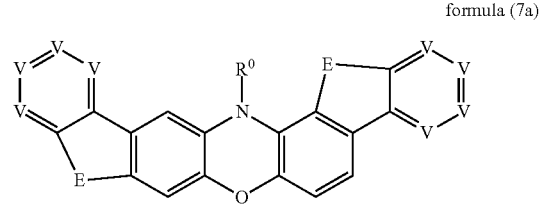

formula (7a)

wherein
V is, identically or differently, $CR^2$ or N or two adjacent groups V optionally are group of formula (8a) or (9a)

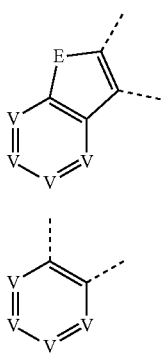

wherein the dashed bonds denote the linking of these units.

8. The compound of claim 7, wherein at least one 6-membered ring in the para position to the O atom of the central ring of the phenoxazine structure comprises two adjacent groups V which are a group of the formula (8a) or (9a).

9. The compound of claim 7, wherein at least one group V is $CR^2$, wherein $R^2$ is selected from the group consisting of $N(R^3)_2$ and aromatic or heteroaromatic ring systems having 5 to 30 aromatic ring atoms, which in each case is optionally substituted by one or more radicals $R^3$.

10. The compound of claim 1, wherein the compound is selected from the group consisting of compounds of formulae (20):

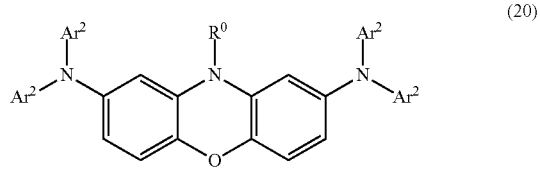

wherein
each free position of the two phenyl rings of the phenoxazine structure in formula (20) are optionally substituted by a radical R.

11. The compound of claim 1, wherein $Ar^e$ is selected, identically or differently, from the group consisting of an aryl and heteroaryl groups having 5 to 18 aromatic ring atoms, which are optionally substituted by one or more radicals $R^2$.

12. The compound of claim 1, wherein $R^0$ is on each occurrence, identically or differently, a straight-chain alkyl having 1 to 20 C atoms or a branched or cyclic alkyl having 3 to 20 C atoms, wherein the above-mentioned groups are optionally substituted by one or more radicals $R^3$ and wherein one or more $CH_2$ groups in the above-mentioned groups are optionally replaced by —$R^3C$=$CR^3$—, —C≡C—, —$NR^3$—, —O—, —S—, or an aromatic or heteroaromatic ring system having 5 to 14 aromatic ring atoms, which in each case is optionally substituted by one or more radicals $R^3$.

13. The compound of claim 1, wherein $R^0$ is an aromatic or heteroaromatic ring system having 5 to 14 aromatic ring atoms, which in each case is optionally substituted by one or more radicals $R^3$.

14. A process for preparing a compound of claim 1, comprising introducing aryl, heteroaryl, diarylamino groups as substituents para to the O atom of a phenoxazine derivative by means of one or more transition metal-catalysed coupling reactions.

15. An oligomer, polymer, or dendrimer comprising one or more compounds of claim 1, wherein the bond(s) to the polymer, oligomer, or dendrimer are optionally localised at any desired positions in formula (1) substituted by R or $R^2$.

16. A formulation comprising at least one compound of claim 1 and at least one solvent.

17. A formulation comprising at least one polymer, oligomer, or dendrimer of claim 15 and at least one solvent.

18. An electronic device comprising at least one compound of claim 1.

19. An electronic device comprising at least one polymer, oligomer, or dendrimer of claim 15.

20. The electronic device of claim 18, wherein the electronic device is selected from the group consisting of organic integrated circuits, organic field-effect transistors, organic thin-film transistors, organic light-emitting transistors, organic solar cells, organic optical detectors, organic photoreceptors, organic field-quench devices, light-emitting electrochemical cells, organic laser diodes, and organic electroluminescent devices.

21. The electronic device of claim 19, wherein the electronic device is selected from the group consisting of organic integrated circuits, organic field-effect transistors, organic thin-film transistors, organic light-emitting transistors, organic solar cells, organic optical detectors, organic photoreceptors, organic field-quench devices, light-emitting electrochemical cells, organic laser diodes, and organic electroluminescent devices.

22. The electronic device of claim 18, wherein the electronic device is selected from the group consisting of organic electroluminescent devices, wherein the compound is employed in one or more of the following functions:
as a blue emitter in an emitting layer;
as a hole-transport material in a hole-transport or hole-injection layer;
as a matrix material in an emitting layer;
as an electron-blocking material; and/or
as an exciton-blocking material.

23. The electronic device of claim 19, wherein the electronic device is selected from the group consisting of organic electroluminescent devices, wherein the polymer, oligomer, or dendrimer is employed in one or more of the following functions:
as a blue emitter in an emitting layer;
as a hole-transport material in a hole-transport or hole-injection layer;
as a matrix material in an emitting layer;
as an electron-blocking material; and/or
as an exciton-blocking material.

* * * * *